US007455973B2

(12) United States Patent
Fischer et al.

(10) Patent No.: US 7,455,973 B2
(45) Date of Patent: Nov. 25, 2008

(54) METHODS AND COMPOSITIONS FOR THE DETECTION OF CERVICAL DISEASE

(75) Inventors: Timothy J. Fischer, Raleigh, NC (US); Douglas P. Malinowski, Hillsborough, NC (US); Adriann J. Taylor, Durham, NC (US); Margaret R. Parker, Raleigh, NC (US)

(73) Assignee: TriPath Imaging, Inc., Burlington, NC (US)

( * ) Notice: Subject to any disclaimer, the term of this patent is extended or adjusted under 35 U.S.C. 154(b) by 0 days.

(21) Appl. No.: 11/506,012

(22) Filed: Aug. 17, 2006

(65) Prior Publication Data

US 2006/0286595 A1 Dec. 21, 2006

Related U.S. Application Data

(62) Division of application No. 11/087,227, filed on Mar. 23, 2005, now Pat. No. 7,157,233.

(60) Provisional application No. 60/556,495, filed on Mar. 24, 2004.

(51) Int. Cl.
*C12Q 1/68* (2006.01)
(52) U.S. Cl. .......................... 435/6; 435/69.1
(58) Field of Classification Search .................. 435/6, 435/69.1
See application file for complete search history.

(56) References Cited

U.S. PATENT DOCUMENTS

| | | | |
|---|---|---|---|
| 5,244,787 | A | 9/1993 | Key et al. |
| 5,858,683 | A | 1/1999 | Keesee et al. |
| 6,303,323 | B1 | 10/2001 | Laskey et al. |
| 2002/0106685 | A1 | 8/2002 | Henning et al. |
| 2003/0087270 | A1 | 5/2003 | Schlegel et al. |
| 2003/0152993 | A1 | 8/2003 | Doeberitz et al. |
| 2003/0219726 | A1 | 11/2003 | Doorbar |
| 2004/0202996 | A1 | 10/2004 | Williams et al. |

FOREIGN PATENT DOCUMENTS

| | | |
|---|---|---|
| WO | WO 99/21014 | 4/1999 |
| WO | WO 02/101075 A1 | 12/2002 |
| WO | WO 2004/013632 A1 | 2/2004 |

OTHER PUBLICATIONS

Sano et al, American Journal of Pathology, Dec. 1998, vol. 153, No. 6, pp. 1741-1748.*
Baldwin, P., et al. "Translation Approaches to Improving Cervical Screening," *Nature Reviews, Cancer*, 2003, pp. 217-226, vol. 3.
Bibbo, M., et al., "Procedure for Immunocytochemical Detection of $P^{16INK4A}$ Antigen in Thin-Layer, Liquid-Based Specimens," *Acta Cytologica*, 2002, pp. 25-29, vol. 46(1).
Bibbo, M., et al., "$p^{16INK4A}$ As an Adjunct Test in Liquid-Based Cytology,"*Analytical and Quantitative Cytology and Histology*, 2003, pp. 8-11, vol. 25(1).
Bourtsos, E.P., and C.D. Sturgis, "ASC-H Cervicovaginal Cytology's Newest Atypia, A Synopsis of Literature, Recommendations, Ongoing Studies, and Community Practice Experience,".
Brake, T., et al.., "Comparative Analysis of Cervical Cancer in Women and in a Human Papillomavirus-Transgenic Mouse Model: Identification of *Minichromosome Maintenance Protein 7* as an Informative Biomarker for Human Cervical Cancer," *Cancer Research*, 2003, pp. 8173-8180, vol. 63.
Chatrath, P., et al., "Aberrant Expression of Minichromosome Maintenance Protein-2 and Ki67 in Laryngeal Squamous Epitherlial Lesions," *British Journal of Cancer*, 2003, pp. 1048-1054, vol. 89.
Davies, R.J., et al., "Analysis of Minichromosome Maintenance Proteins as a Novel Method of Detection of Colorectal Cancer in Stool," *The Lancet*, 2002, pp. 1917-1919, vol. 359(9321).
Elit, L.M., "Pitfalls in the Diagnosis of Cervical Intraepithelial Neoplasia I," *Journal of Lower Genital Tract Disease*, 2004, pp. 181-187, vol. 8(3).
Freeman, A., et al., "Minichromosome Maintenance Proteins as Biological Markers of Dysplasia and Malignancy[1] ," *Clinical Cancer Research*, 1999, pp. 2121-2132, vol. 5.
Gonzalez, M.A., et al., "Minichromosome Maintenance Protein 2 Is a Strong Independent Prognostic Marker in Breast Cancer," *Journal of Clinical Onocology*, 2003, pp. 1-8, vol. 21(23).
Hunt, D.P.J., et al., "Early Recurrence of Benign Meningioma Correlates With Expression of Mini-Chromosome Maintenance-2 Protein," *British Journal of Neurosurgery*, 2002, pp. 10-15, vol. 16(1).
Ishimi, Y., et al., "Enhanced Expression of Mcm Proteins in Cancer Cells Derived from Uterine Cervix," *Eur. J. Biochem.*, 2003, pp. 1089-1101, vol. 270.
Laskey, R., "Initiation of DNA Replication in Normal and Neoplastic Cells," 5th *Congress of the European Haematology Association—Educational Book, Session 11—Cell Cycle*, 2000, pp. 152-155.
Malinowski, D.P., "Molecular Diagnostic Assays for Cervical Neoplasia: Emerging Markers for the Detection of High-Grade Cervical Disease," *BioTechniques*, 2005, pp. 1-8, vol. 38(3).

(Continued)

*Primary Examiner*—Ali R. Salimi
(74) *Attorney, Agent, or Firm*—Alston & Bird LLP

(57) ABSTRACT

Methods and compositions for identifying high-grade cervical disease in a patient sample are provided. The methods of the invention comprise detecting overexpression of at least one biomarker in a body sample, wherein the biomarker is selectively overexpressed in high-grade cervical disease. In particular claims, the body sample is a cervical smear or monolayer of cervical cells. The biomarkers of the invention include genes and proteins that are involved in cell cycle regulation, signal transduction, and DNA replication and transcription. In particular claims, the biomarker is an S-phase gene. In some aspects of the invention, overexpression of a biomarker of interest is detected at the protein level using biomarker-specific antibodies or at the nucleic acid level using nucleic acid hybridization techniques. Kits for practicing the methods of the invention are further provided.

8 Claims, 9 Drawing Sheets

OTHER PUBLICATIONS

Murphy, N., et al., "p16$^{INK4A}$ as A Marker for Cervical Dyskaryosis: CIN and cGIN in Cervical Biopsies and ThinPrep™ Smears," *J. Clin. Pathol.*, 2003, pp. 56-63, vol. 56.

Neih, S., et al., "Expression of p16$^{INK4A}$ in Papanicolaou Smears Containing Atypical Squamous Cells of Undetermined Significance From the Uterine Cervix," *Gynecologic Onocology*, 2003, pp. 201-208, vol. 91.

Saqi, A., et al., Overexpression of p16$^{INK4A}$ in Liquid-Based Specimens (SurePath™) as Marker of Cervical Dysplasia and Neoplasia, *Diagnostic Cytopathology*, 2002, pp. 365-370, vol. 27(6).

Scott, I.S., et al., A Novel Immunohistochemical Method to Estimate Cell-Cycle Phase Distribution in Archival Tissue: Implications for the Prediction of Outcome in Colorectal Cancer, *Journal of Pathology*, 2003, pp. 187-197, vol. 201.

Whitfield, M.L., "Identification of Genes Periodically Expressed in the Human Cell Cycle and Their Expression in Tumors," *Molecular Biology of the Cell*, 2002, pp. 1977-2000, vol. 13.

Williams, G.H., et al., "Improved Cervical Smear Assessment Using Antibodies Against Proteins That Regulate DNA Replication," *Proc. Natl. Acad. Sci.* USA, 1998, pp. 14932-14937, vol. 95.

* cited by examiner

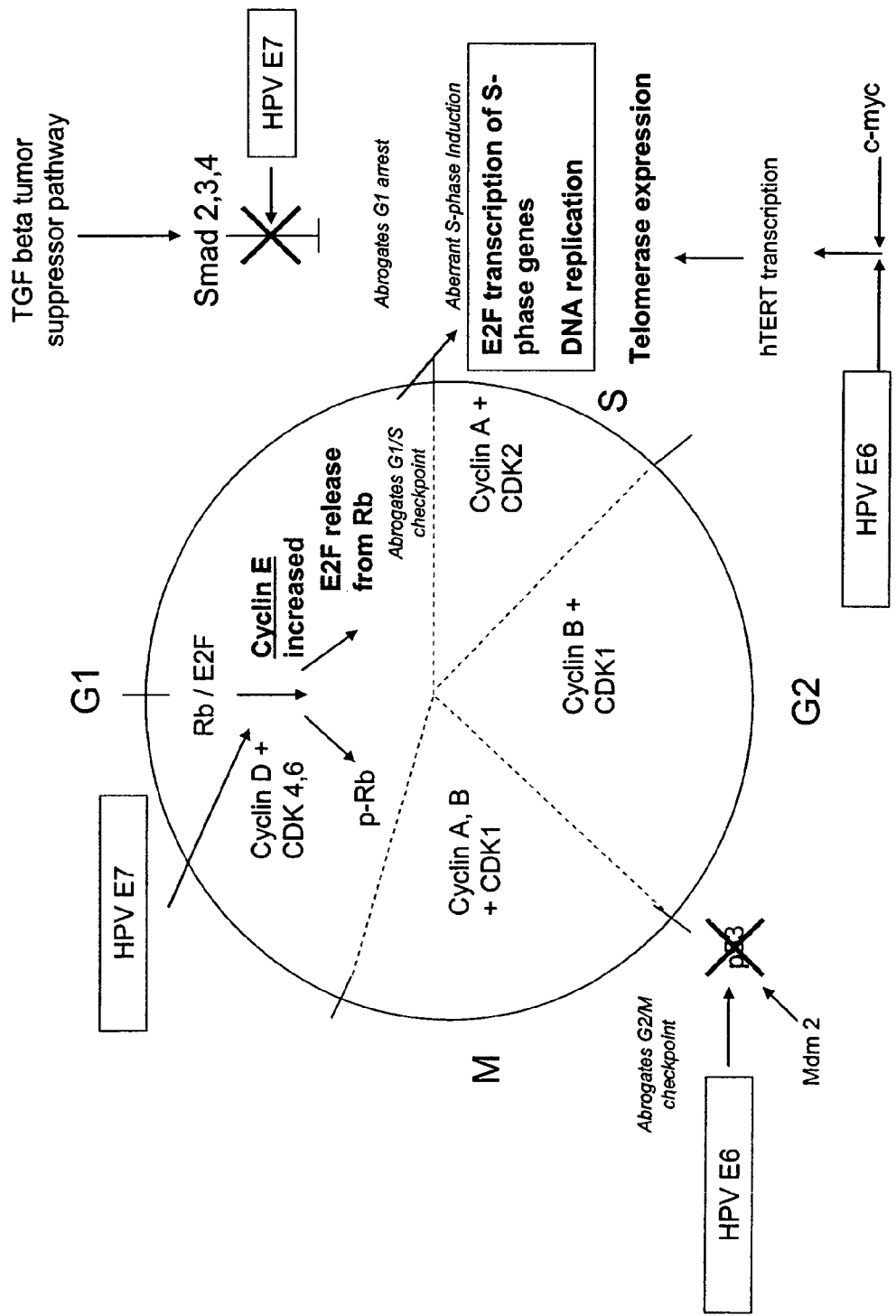
FIG. 1: Proliferation and Cell Cycle De-regulation in Cervical Dysplasia

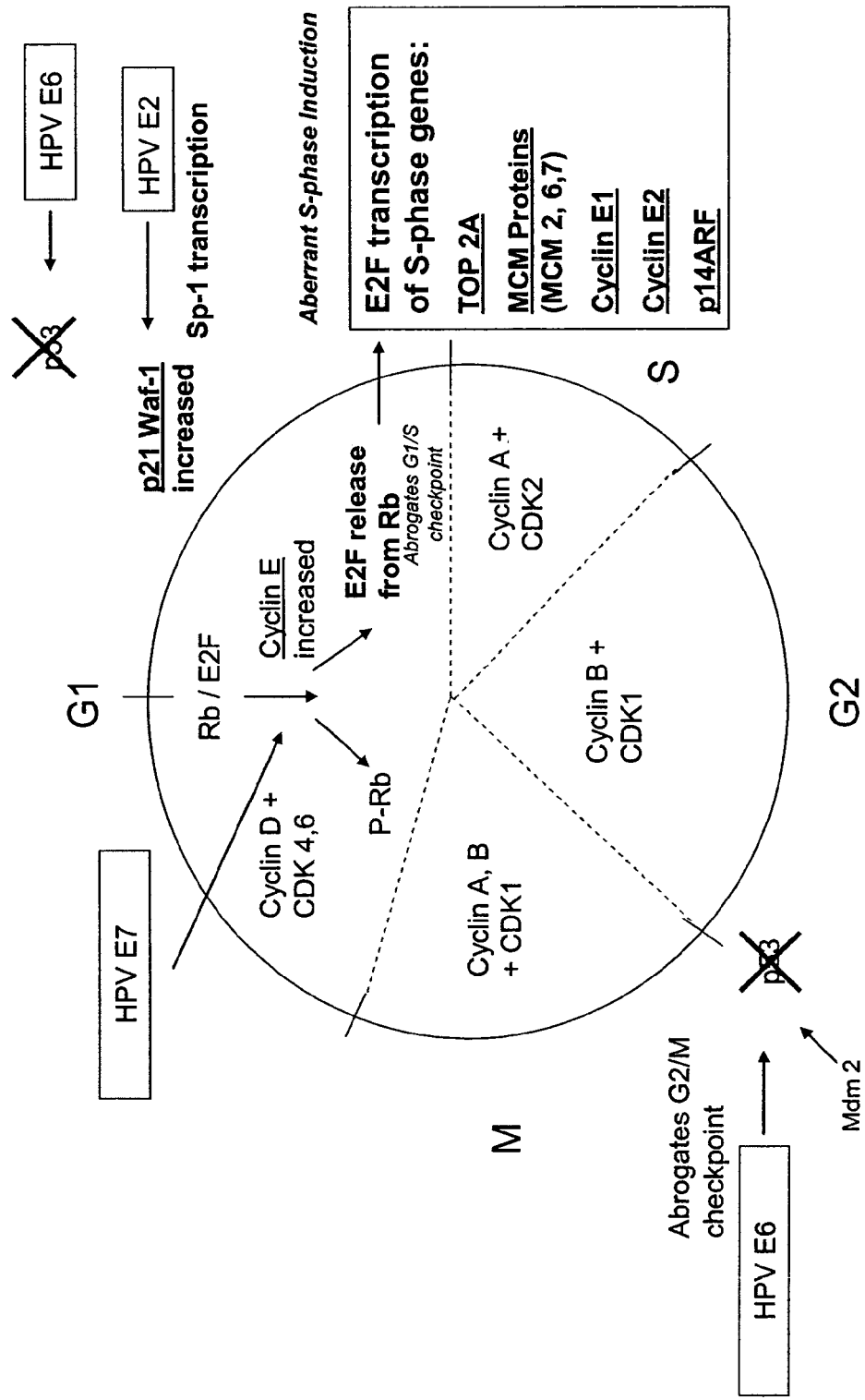
FIG. 2: Aberrant S-Phase Induction in Cervical Neoplasia

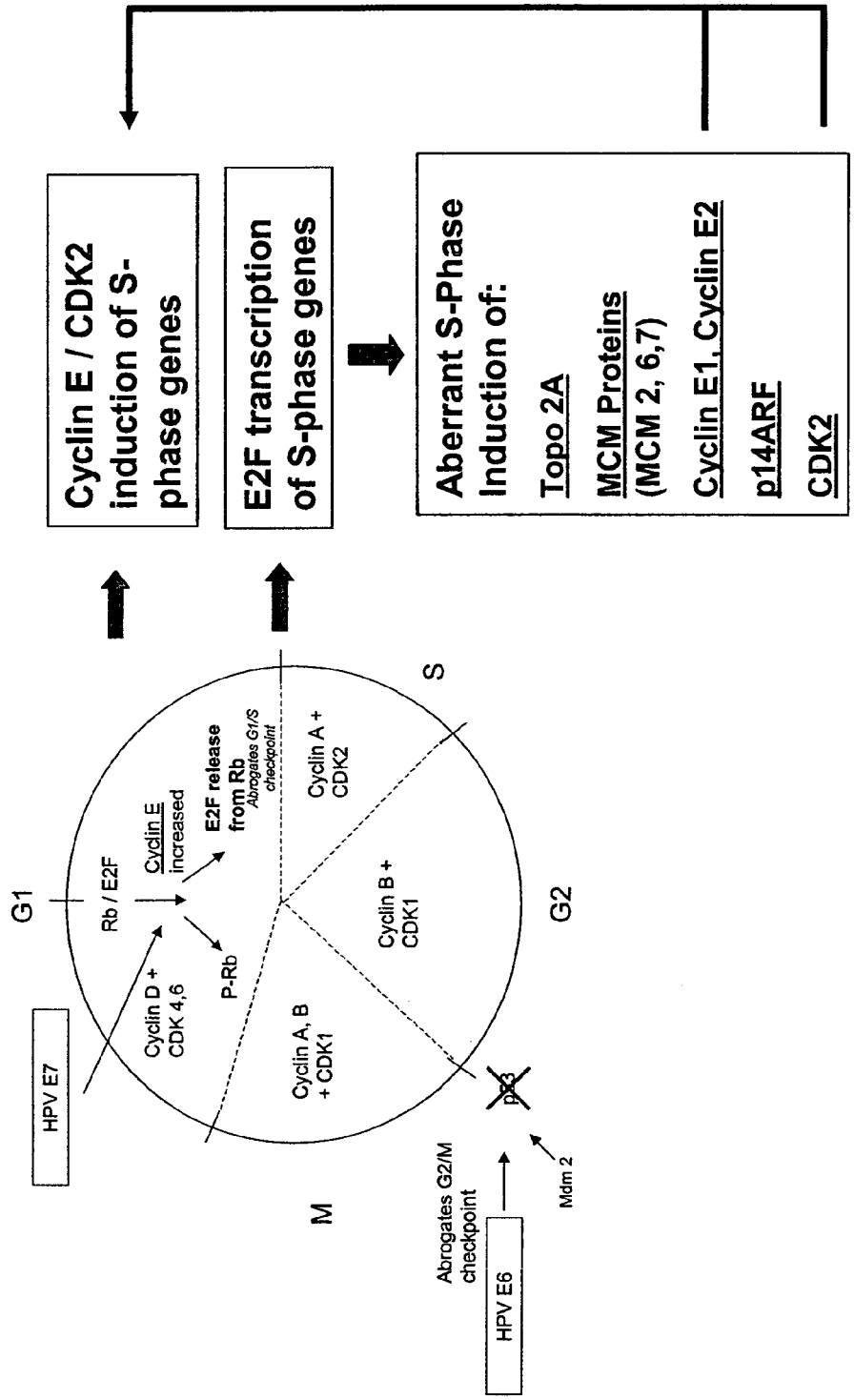
FIG. 3: Aberrant S-Phase Induction in Cervical Neoplasia

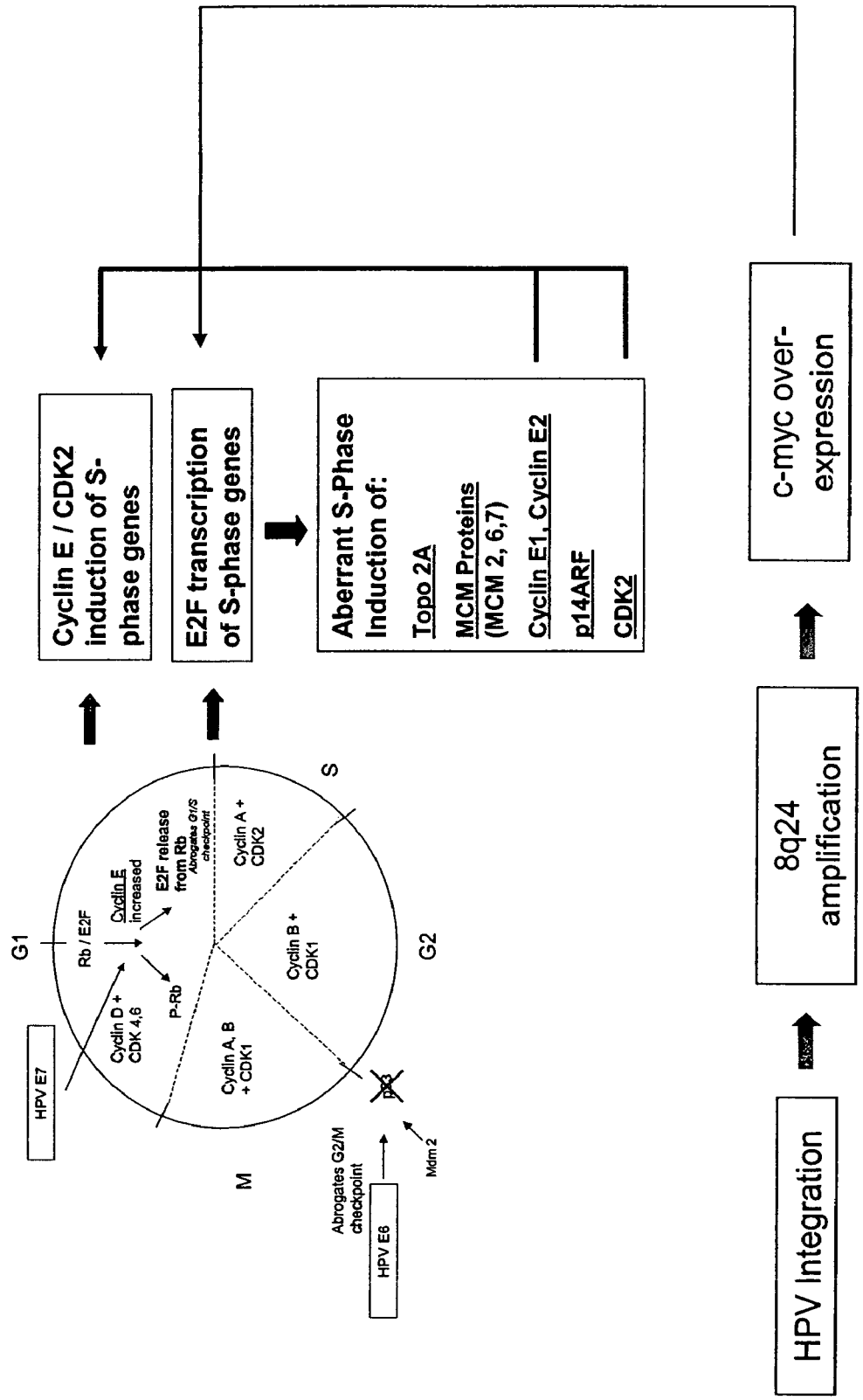
FIG. 4: Aberrant S-Phase Induction in Cervical Neoplasia

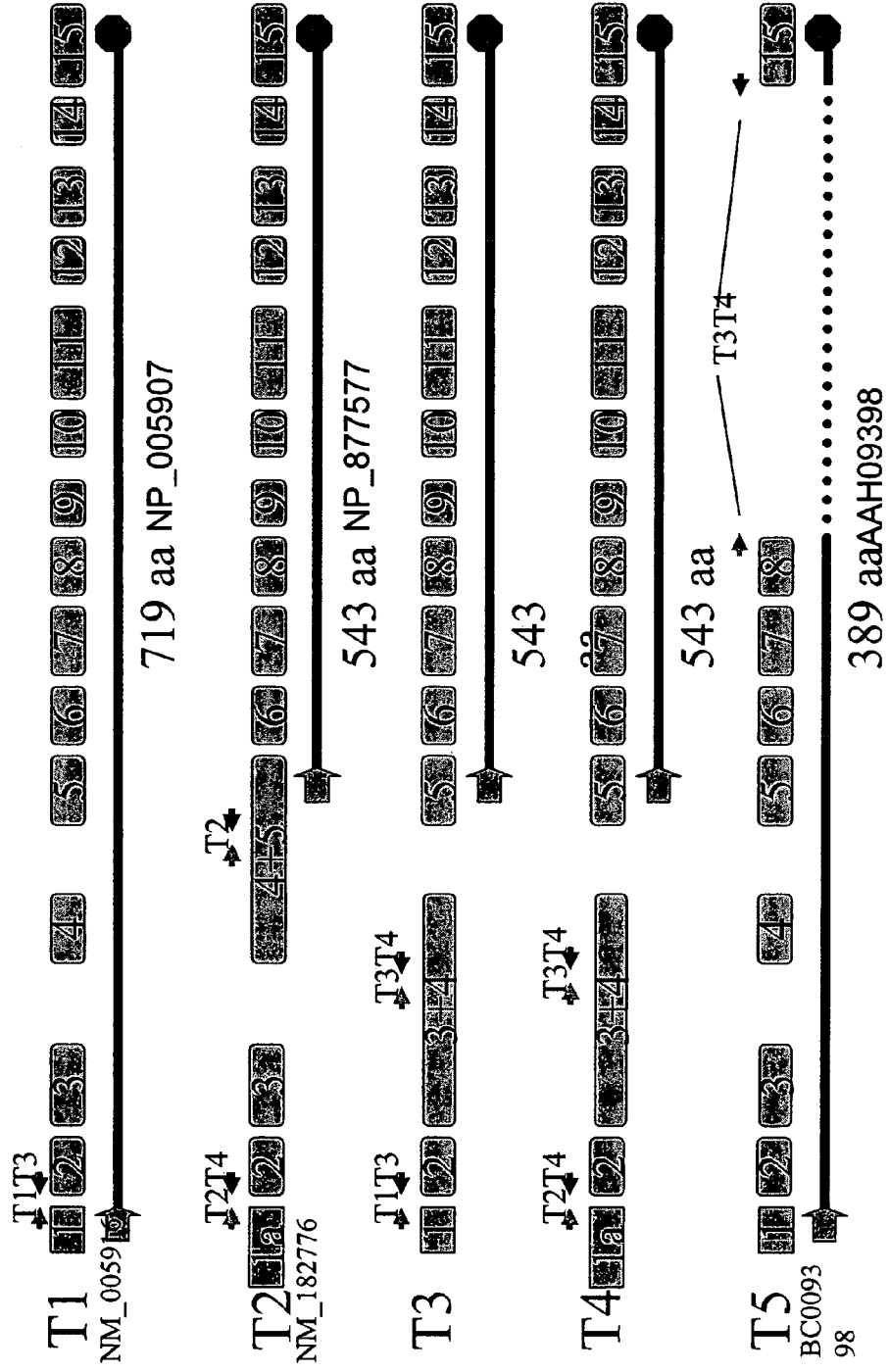

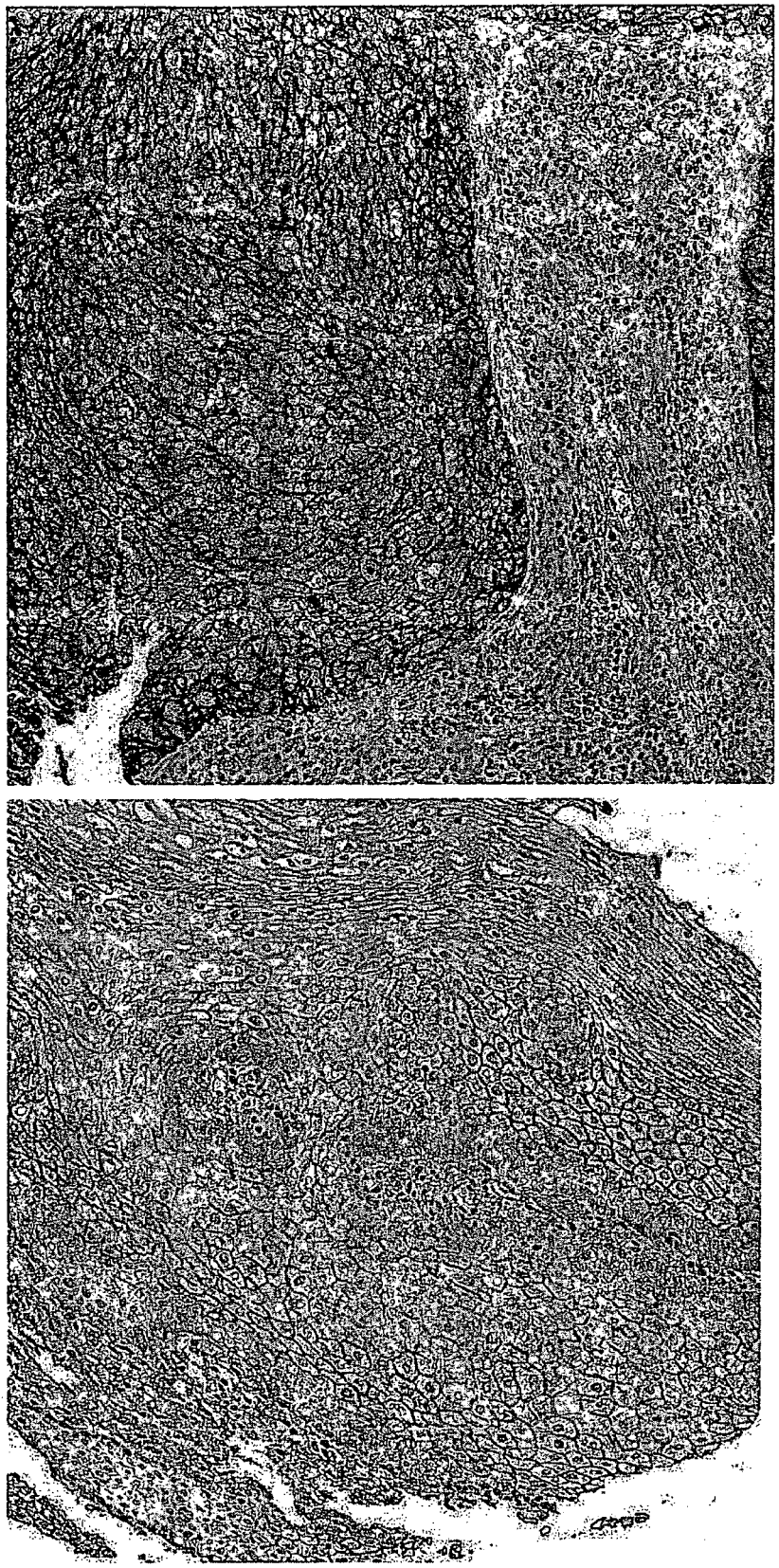
FIG. 6: Claudin I expression in cervical tissue samples (IHC)

FIG. 7: Claudin I expression in tissue (IHC) and cytology (ICC) samples
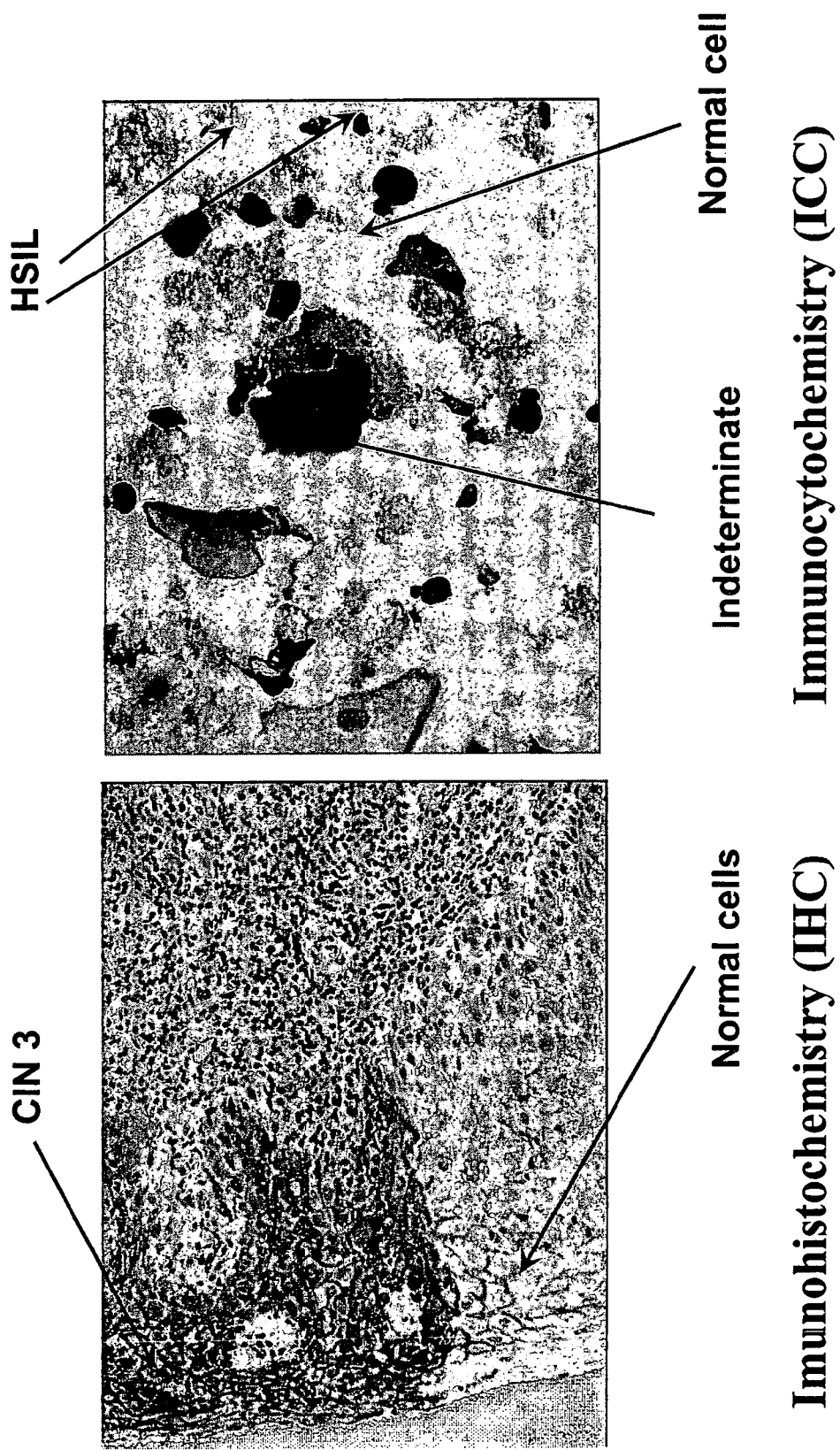

FIG. 8: ICC Assay with High-Grade Cervical Disease Sample

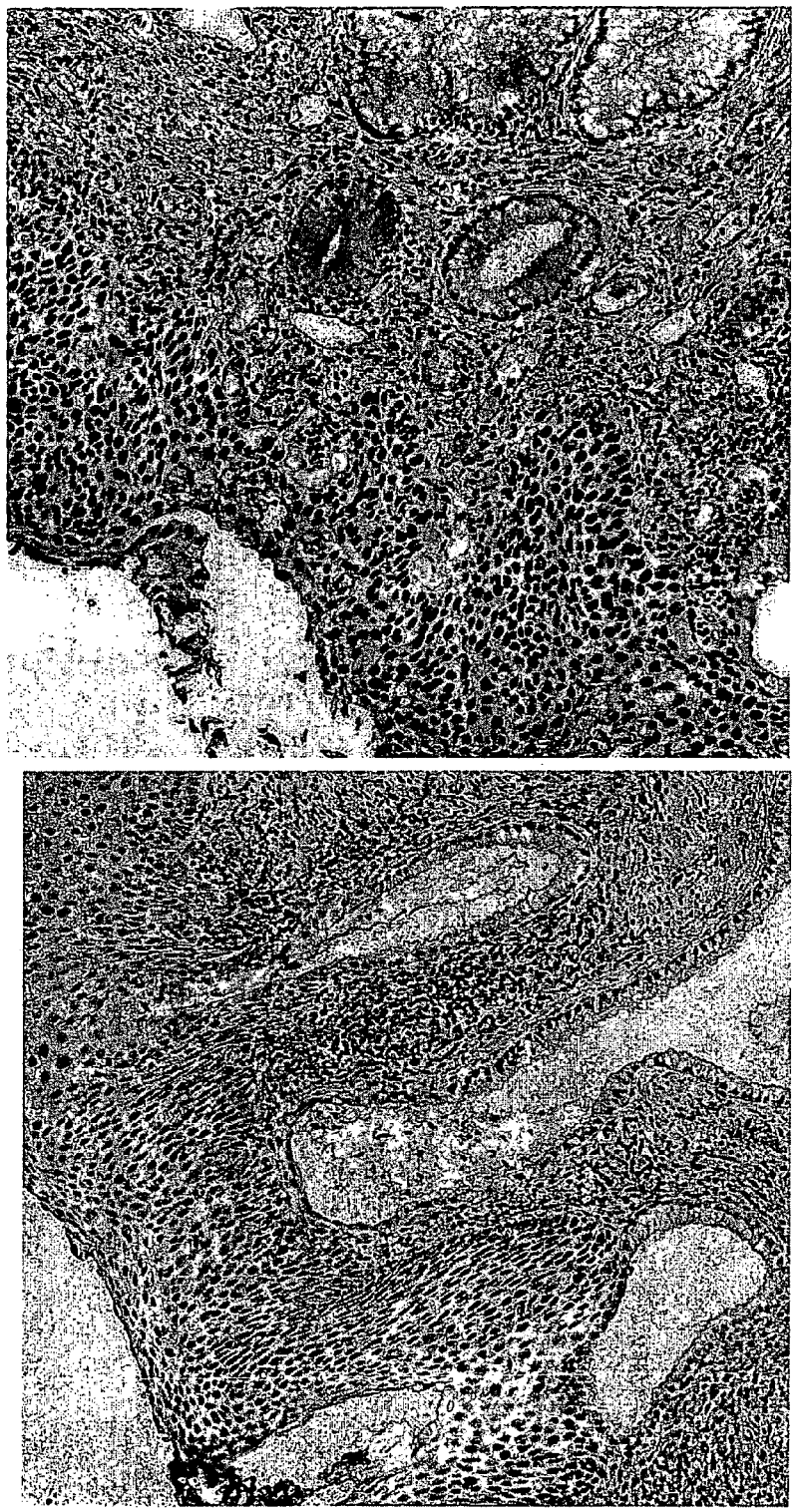
FIG. 9: Differential staining patterns in cervical tissue samples (IHC) using different MCM6 antibodies
Optimal Mab Staining
Antibody made In house
Suboptimal Mab Staining
Antibody from Transduction Labs

SEQUENCE LISTING

<160> NUMBER OF SEQ ID NOS: 90

<210> SEQ ID NO 1
<211> LENGTH: 1958
<212> TYPE: DNA
<213> ORGANISM: Homo sapiens

<400> SEQUENCE: 1

```
agcagccggc gcggccgcca gcgcggtgta gggggcaggc gcggatcccg ccaccgccgc      60
gcgctcggcc cgccgactcc cggcgccgcc gccgccactg ccgtcgccgc cgccgcctgc     120
cgggactgga gcgcgccgtc cgccgcggac aagaccctgg cctcaggccg gagcagcccc     180
atcatgccga gggagcgcag ggagcgggat gcgaaggagc gggacaccat gaaggaggac     240
ggcggcgcgg agttctcggc tcgctccagg aagaggaagg caaacgtgac cgttttttg      300
caggatccag atgaagaaat ggccaaaatc gacaggacgg cgagggacca gtgtgggagc     360
cagccttggg acaataatgc agtctgtgca gacccctgct ccctgatccc cacacctgac     420
aaagaagatg atgaccgggt ttacccaaac tcaacgtgca agcctcggat tattgcacca     480
tccagaggct ccccgctgcc tgtactgagc tgggcaaata gagaggaagt ctggaaaatc     540
atgttaaaca aggaaaagac atacttaagg gatcagcact ttcttgagca acaccctctt     600
ctgcagccaa aaatgcgagc aattcttctg gattggttaa tggaggtgtg tgaagtctat     660
aaacttcaca gggagacctt ttacttggca caagatttct ttgaccggta tatggcgaca     720
caagaaaatg ttgtaaaaac tcttttacag cttattggga tttcatcttt atttattgca     780
gccaaacttg aggaaatcta tcctccaaag ttgcaccagt ttgcgtatgt gacagatgga     840
gcttgttcag gagatgaaat tctcaccatg gaattaatga ttatgaaggc ccttaagtgg     900
cgtttaagtc ccctgactat tgtgtcctgg ctgaatgtat acatgcaggt tgcatatcta     960
aatgacttac atgaagtgct actgccgcag tatccccagc aaatctttat acagattgca    1020
gagctgttgg atctctgtgt cctggatgtt gactgccttg aatttcctta tggtatactt    1080
gctgcttcgg ccttgtatca tttctcgtca tctgaattga tgcaaaaggt ttcagggtat    1140
cagtggtgcg acatagagaa ctgtgtcaag tggatggttc catttgccat ggttataagg    1200
gagacgggga gctcaaaact gaagcacttc aggggcgtcg ctgatgaaga tgcacacaac    1260
atacagaccc acagagacag cttggatttg ctggacaaag cccgagcaaa gaaagccatg    1320
ttgtctgaac aaaatagggc ttctcctctc cccagtgggc tcctcacccc gccacagagc    1380
ggtaagaagc agagcagcgg gccggaaatg gcgtgaccac cccatccttc tccaccaaag    1440
```

```
acagttgcgc gcctgctcca cgttctcttc tgtctgttgc agcggaggcg tgcgtttgct   1500
tttacagata tctgaatgga agagtgtttc ttccacaaca gaagtatttc tgtggatggc   1560
atcaaacagg gcaaagtgtt ttttattgaa tgcttatagg tttttttttaa ataagtgggt   1620 caagtacacc agccacctcc agacaccagt gcgtgctccc gatgctgcta tggaaggtgc   1680
tacttgacct aagggactcc cacaacaaca aaagcttgaa gctgtggagg gccacggtgg   1740
cgtggctctc ctcgcaggtg ttctgggctc cgttgtacca agtggagcag gtggttgcgg   1800
gcaagcgttg tgcagagccc atagccagct gggcagggg ctgccctctc cacattatca   1860
gttgacagtg tacaatgcct tgatgaact gttttgtaag tgctgctata tctatccatt   1920
ttttaataaa gataatactg tttttgagac aaaaaaaa                           1958
```

```
<210> SEQ ID NO 2
<211> LENGTH: 410
<212> TYPE: PRT
<213> ORGANISM: Homo sapiens

<400> SEQUENCE: 2

Met Pro Arg Glu Arg Arg Glu Arg Asp Ala Lys Glu Arg Asp Thr Met
 1               5                  10                  15

Lys Glu Asp Gly Gly Ala Glu Phe Ser Ala Arg Ser Arg Lys Arg Lys
                20                  25                  30

Ala Asn Val Thr Val Phe Leu Gln Asp Pro Asp Glu Glu Met Ala Lys
            35                  40                  45

Ile Asp Arg Thr Ala Arg Asp Gln Cys Gly Ser Gln Pro Trp Asp Asn
    50                  55                  60

Asn Ala Val Cys Ala Asp Pro Cys Ser Leu Ile Pro Thr Pro Asp Lys
65                  70                  75                  80

Glu Asp Asp Asp Arg Val Tyr Pro Asn Ser Thr Cys Lys Pro Arg Ile
                85                  90                  95

Ile Ala Pro Ser Arg Gly Ser Pro Leu Pro Val Leu Ser Trp Ala Asn
            100                 105                 110

Arg Glu Glu Val Trp Lys Ile Met Leu Asn Lys Glu Lys Thr Tyr Leu
        115                 120                 125

Arg Asp Gln His Phe Leu Glu Gln His Pro Leu Leu Gln Pro Lys Met
    130                 135                 140

Arg Ala Ile Leu Leu Asp Trp Leu Met Glu Val Cys Glu Val Tyr Lys
145                 150                 155                 160

Leu His Arg Glu Thr Phe Tyr Leu Ala Gln Asp Phe Phe Asp Arg Tyr
                165                 170                 175

Met Ala Thr Gln Glu Asn Val Val Lys Thr Leu Leu Gln Leu Ile Gly
            180                 185                 190

Ile Ser Ser Leu Phe Ile Ala Ala Lys Leu Glu Glu Ile Tyr Pro Pro
        195                 200                 205

Lys Leu His Gln Phe Ala Tyr Val Thr Asp Gly Ala Cys Ser Gly Asp
    210                 215                 220

Glu Ile Leu Thr Met Glu Leu Met Ile Met Lys Ala Leu Lys Trp Arg
225                 230                 235                 240

Leu Ser Pro Leu Thr Ile Val Ser Trp Leu Asn Val Tyr Met Gln Val
                245                 250                 255

Ala Tyr Leu Asn Asp Leu His Glu Val Leu Leu Pro Gln Tyr Pro Gln
            260                 265                 270

Gln Ile Phe Ile Gln Ile Ala Glu Leu Leu Asp Leu Cys Val Leu Asp
```

```
                275                 280                 285
Val Asp Cys Leu Glu Phe Pro Tyr Gly Ile Leu Ala Ala Ser Ala Leu
    290                 295                 300

Tyr His Phe Ser Ser Ser Glu Leu Met Gln Lys Val Ser Gly Tyr Gln
305                 310                 315                 320

Trp Cys Asp Ile Glu Asn Cys Val Lys Trp Met Val Pro Phe Ala Met
                325                 330                 335

Val Ile Arg Glu Thr Gly Ser Ser Lys Leu Lys His Phe Arg Gly Val
            340                 345                 350

Ala Asp Glu Asp Ala His Asn Ile Gln Thr His Arg Asp Ser Leu Asp
        355                 360                 365

Leu Leu Asp Lys Ala Arg Ala Lys Lys Ala Met Leu Ser Glu Gln Asn
    370                 375                 380

Arg Ala Ser Pro Leu Pro Ser Gly Leu Leu Thr Pro Pro Gln Ser Gly
385                 390                 395                 400

Lys Lys Gln Ser Ser Gly Pro Glu Met Ala
                405                 410

<210> SEQ ID NO 3
<211> LENGTH: 1787
<212> TYPE: DNA
<213> ORGANISM: Homo sapiens

<400> SEQUENCE: 3
gtgctcaccc ggcccggtgc cacccgggtc cacagggatg cgaaggagcg ggacaccatg      60
aaggaggacg gcggcgcgga gttctcggct cgctccagga agaggaaggc aaacgtgacc     120 gttttttgc aggatccaga tgaagaaatg gccaaaatcg acaggacggc gagggaccag      180
tgtgggagcc agccttggga caataatgca gtctgtgcag acccctgctc cctgatcccc     240
acacctgaca agaagatga tgaccgggtt acccaaaact caacgtgcaa gcctcggatt      300
attgcaccat ccagaggctc cccgctgcct gtactgagct gggcaaatag agaggaagtc     360
tggaaaatca tgttaaacaa ggaaaagaca tacttaaggg atcagcactt tcttgagcaa     420
caccctcttc tgcagccaaa aatgcgagca attcttctgg attggttaat ggaggtgtgt     480
gaagtctata aacttcacag ggagaccttt tacttggcac aagatttctt tgaccggtat     540
atggcgacac aagaaaatgt tgtaaaaact cttttacagc ttattgggat ttcatcttta     600
tttattgcag ccaaacttga ggaaatctat cctccaaagt tgcaccagtt tgcgtatgtg     660
acagatggag cttgttcagg agatgaaatt ctcaccatgg aattaatgat tatgaaggcc     720
cttaagtggc gtttaagtcc cctgactatt gtgtcctggc tgaatgtata catgcaggtt     780
gcatatctaa atgacttaca tgaagtgcta ctgccgcagt atccccagca atctttata     840 cagattgcag agctgttgga tctctgtgtc ctggatgttg actgccttga atttccttat     900
ggtatacttg ctgcttcggc cttgtatcat ttctcgtcat ctgaattgat gcaaaaggtt     960
tcagggtatc agtggtgcga catagagaac tgtgtcaagt ggatggttcc atttgccatg    1020
gttataaggg agacggggag ctcaaaactg aagcacttca gggcgtcgc tgatgaagat    1080 gcacacaaca tacagaccca cagagacagc ttggatttgc tggacaaagc ccgagcaaag    1140
aaagccatgt tgtctgaaca aaatagggct ctcctctcc ccagtgggct cctcaccccg     1200
ccacagagcg gtaagaagca gagcagcggg ccggaaatgg cgtgaccacc ccatccttct    1260
ccaccaaaga cagttgcgcg cctgctccac gttctcttct gtctgttgca gcggaggcgt    1320
gcgtttgctt ttacagatat ctgaatggaa gagtgtttct tccacaacag aagtatttct    1380
```

-continued

```
gtggatggca tcaaacaggg caaagtgttt tttattgaat gcttataggt ttttttttaaa    1440 taagtgggtc aagtacacca gccacctcca gacaccagtg cgtgctcccg atgctgctat    1500
ggaaggtgct acttgaccta agggactccc acaacaacaa aagcttgaag ctgtggaggg    1560
ccacggtggc gtggctctcc tcgcaggtgt tctgggctcc gttgtaccaa gtggagcagg    1620
tggttgcggg caagcgttgt gcagagccca tagccagctg gcagggggc tgccctctcc     1680 acattatcag ttgacagtgt acaatgcctt tgatgaactg ttttgtaagt gctgctatat    1740
ctatccattt tttaataaag ataatactgt ttttgagaca aaaaaaa                  1787
```

<210> SEQ ID NO 4
<211> LENGTH: 395
<212> TYPE: PRT
<213> ORGANISM: Homo sapiens

<400> SEQUENCE: 4

```
Met Lys Glu Asp Gly Gly Ala Glu Phe Ser Ala Arg Ser Arg Lys Arg
  1               5                  10                  15

Lys Ala Asn Val Thr Val Phe Leu Gln Asp Pro Asp Glu Glu Met Ala
                 20                  25                  30

Lys Ile Asp Arg Thr Ala Arg Asp Gln Cys Gly Ser Gln Pro Trp Asp
             35                  40                  45

Asn Asn Ala Val Cys Ala Asp Pro Cys Ser Leu Ile Pro Thr Pro Asp
         50                  55                  60

Lys Glu Asp Asp Asp Arg Val Tyr Pro Asn Ser Thr Cys Lys Pro Arg
 65                  70                  75                  80

Ile Ile Ala Pro Ser Arg Gly Ser Pro Leu Pro Val Leu Ser Trp Ala
                 85                  90                  95

Asn Arg Glu Glu Val Trp Lys Ile Met Leu Asn Lys Glu Lys Thr Tyr
            100                 105                 110

Leu Arg Asp Gln His Phe Leu Glu Gln His Pro Leu Leu Gln Pro Lys
        115                 120                 125

Met Arg Ala Ile Leu Leu Asp Trp Leu Met Glu Val Cys Glu Val Tyr
    130                 135                 140

Lys Leu His Arg Glu Thr Phe Tyr Leu Ala Gln Asp Phe Phe Asp Arg
145                 150                 155                 160

Tyr Met Ala Thr Gln Glu Asn Val Val Lys Thr Leu Leu Gln Leu Ile
                165                 170                 175

Gly Ile Ser Ser Leu Phe Ile Ala Ala Lys Leu Glu Glu Ile Tyr Pro
            180                 185                 190

Pro Lys Leu His Gln Phe Ala Tyr Val Thr Asp Gly Ala Cys Ser Gly
        195                 200                 205

Asp Glu Ile Leu Thr Met Glu Leu Met Ile Met Lys Ala Leu Lys Trp
    210                 215                 220

Arg Leu Ser Pro Leu Thr Ile Val Ser Trp Leu Asn Val Tyr Met Gln
225                 230                 235                 240

Val Ala Tyr Leu Asn Asp Leu His Glu Val Leu Leu Pro Gln Tyr Pro
                245                 250                 255

Gln Gln Ile Phe Ile Gln Ile Ala Glu Leu Leu Asp Leu Cys Val Leu
            260                 265                 270

Asp Val Asp Cys Leu Glu Phe Pro Tyr Gly Ile Leu Ala Ala Ser Ala
        275                 280                 285

Leu Tyr His Phe Ser Ser Ser Glu Leu Met Gln Lys Val Ser Gly Tyr
    290                 295                 300
```

```
Gln Trp Cys Asp Ile Glu Asn Cys Val Lys Trp Met Val Pro Phe Ala
305                 310                 315                 320

Met Val Ile Arg Glu Thr Gly Ser Ser Lys Leu Lys His Phe Arg Gly
            325                 330                 335

Val Ala Asp Glu Asp Ala His Asn Ile Gln Thr His Arg Asp Ser Leu
        340                 345                 350

Asp Leu Leu Asp Lys Ala Arg Ala Lys Lys Ala Met Leu Ser Glu Gln
    355                 360                 365

Asn Arg Ala Ser Pro Leu Pro Ser Gly Leu Leu Thr Pro Pro Gln Ser
370                 375                 380

Gly Lys Lys Gln Ser Ser Gly Pro Glu Met Ala
385                 390                 395

<210> SEQ ID NO 5
<211> LENGTH: 2748
<212> TYPE: DNA
<213> ORGANISM: Homo sapiens

<400> SEQUENCE: 5
agcgggtgcg gggcgggacc ggcccggcct atatattggg ttggcgccgg cgccagctga     60
gccgagcggt agctggtctg gcgaggtttt atacacctga agaagagaaa tgtcaagacg    120
aagtagccgt ttacaagcta agcagcagcc ccagcccagc cagacggaat ccccccaaga    180
agcccagata tccaggcca agaagaggaa aactacccag gatgtcaaaa aagaagaga     240 ggaggtcacc aagaaacatc agtatgaaat taggaattgt tggccacctg tattatctgg    300
ggggatcagt ccttgcatta tcattgaaac acctcacaaa gaaataggaa caagtgattt    360
ctccagattt acaaattaca gatttaaaaa tcttttatt aatccttcac ctttgcctga    420
tttaagctgg ggatgttcaa agaagtctg gctaaacatg ttaaaaaagg agagcagata    480
tgttcatgac aaacattttg aagttctgca ttctgacttg aaccacagaa tgaggtccat    540
acttctagac tggcttttag aggtatgtga agtatacaca cttcataggg aaacatttta    600
tcttgcacaa gacttttttg atagatttat gttgacacaa aaggatataa ataaaaatat    660
gcttcaactc attggaatta cctcattatt cattgcttcc aaacttgagg aaatctatgc    720
tcctaaactc caagagtttg cttacgtcac tgatggtgct gcagtgaag aggatatctt    780 aaggatggaa ctcattatat taaaggcttt aaaatgggaa cttt gtcctg taacaatcat    840 ctcctggcta aatctctttc tccaagttga tgctcttaaa gatgctccta agttcttct    900 acctcagtat tctcaggaaa cattcattca aatagctcag ctttagatc tgtgtattct    960 agccattgat tcattagagt tccagtacag aatactgact gctgctgcct tgtgccattt   1020
tacctccatt gaagtggtta agaaagcctc aggtttggag tgggacagta tttcagaatg   1080
tgtagattgg atggtacctt ttgtcaatgt agtaaaaagt actagtccag tgaagctgaa   1140 gactttaag aagattccta tggaagacag acataatatc cagacacata caaactattt   1200
ggctatgctg gaggaagtaa attacataaa caccttcaga aaaggggac agttgtcacc   1260 agtgtgcaat ggaggcatta tgacaccacc gaagagcact gaaaaaccac caggaaaaca   1320
ctaaagaaga taactaagca aacagttgg aattcaccaa gattgggtag aactggtatc   1380
actgaactac taaagtttta cagaaagtag tgctgtgatt gattgcccta gccaattcac   1440
aagttacact gccattctga tttaaaaact tacaattggc actaaagaat acatttaatt   1500
atttcctatg ttagctgtta aagaaacagc aggacttgtt tacaaagatg tcttcattcc   1560
```

-continued

```
caaggttact ggatagaagc caaccacagt ctataccata gcaatgtttt tcctttaatc   1620
cagtgttact gtgtttatct tgataaacta ggaattttgt cactggagtt ttggactgga   1680
taagtgctac cttaaagggt atactaagtg atacagtact ttgaatctag ttgttagatt   1740
ctcaaaattc ctacactctt gactagtgca atttggttct tgaaaattaa atttaaactt   1800
gtttacaaag gtttagtttt gtaataaggt gactaattta tctatagctg ctatagcaag   1860
ctattataaa acttgaattt ctacaaatgg tgaaatttaa tgttttttaa actagtttat   1920
ttgccttgcc ataacacatt ttttaactaa taaggcttag atgaacatgg tgttcaacct   1980
gtgctctaaa cagtgggagt accaaagaaa ttataaacaa gataaatgct gtggctcctt   2040
cctaactggg gctttcttga catgtaggtt gcttggtaat aaccttttg tatatcacaa    2100 tttgggtgaa aaacttaagt acccttttcaa actatttata tgaggaagtc actttactac  2160
tctaagatat ccctaaggaa ttttttttt taatttagtg tgactaaggc tttatttatg    2220
tttgtgaaac tgttaaggtc ctttctaaat tcctccattg tgagataagg acagtgtcaa   2280
agtgataaag cttaacactt gacctaaact tctattttct taaggaagaa gagtattaaa   2340
tatatactga ctcctagaaa tctatttatt aaaaaaagac atgaaaactt gctgtacata   2400
ggctagctat ttctaaatat tttaaattag cttttctaaa aaaaaaatcc agcctcataa   2460
agtagattag aaaactagat tgctagttta ttttgttatc agatatgtga atctcttctc   2520
cctttgaaga aactatacat ttattgttac ggtatgaagt cttctgtata gtttgttttt   2580 aaactaaat ttgtttcagt attttgtctg aaaagaaaac accactaatt gtgtacatat    2640
gtattatata aacttaacct tttaatactg tttatttta gcccattgtt taaaaaataa    2700
aagttaaaaa aatttaactg cttaaaagta aaaaaaaaa aaaaaaaa                 2748
```

<210> SEQ ID NO 6
<211> LENGTH: 404
<212> TYPE: PRT
<213> ORGANISM: Homo sapiens

<400> SEQUENCE: 6

```
Met Ser Arg Arg Ser Ser Arg Leu Gln Ala Lys Gln Gln Pro Gln Pro
1               5                   10                  15

Ser Gln Thr Glu Ser Pro Gln Glu Ala Gln Ile Ile Gln Ala Lys Lys
            20                  25                  30

Arg Lys Thr Thr Gln Asp Val Lys Lys Arg Arg Glu Glu Val Thr Lys
        35                  40                  45

Lys His Gln Tyr Glu Ile Arg Asn Cys Trp Pro Val Leu Ser Gly
    50                  55                  60

Gly Ile Ser Pro Cys Ile Ile Glu Thr Pro His Lys Glu Ile Gly
65                  70                  75                  80

Thr Ser Asp Phe Ser Arg Phe Thr Asn Tyr Arg Phe Lys Asn Leu Phe
                85                  90                  95

Ile Asn Pro Ser Pro Leu Pro Asp Leu Ser Trp Gly Cys Ser Lys Glu
            100                 105                 110

Val Trp Leu Asn Met Leu Lys Lys Glu Ser Arg Tyr Val His Asp Lys
        115                 120                 125

His Phe Glu Val Leu His Ser Asp Leu Glu Pro Gln Met Arg Ser Ile
    130                 135                 140

Leu Leu Asp Trp Leu Leu Glu Val Cys Glu Val Tyr Thr Leu His Arg
145                 150                 155                 160

Glu Thr Phe Tyr Leu Ala Gln Asp Phe Phe Asp Arg Phe Met Leu Thr
```

```
                    165                 170                 175
Gln Lys Asp Ile Asn Lys Asn Met Leu Gln Leu Ile Gly Ile Thr Ser
                180                 185                 190

Leu Phe Ile Ala Ser Lys Leu Glu Glu Ile Tyr Ala Pro Lys Leu Gln
            195                 200                 205

Glu Phe Ala Tyr Val Thr Asp Gly Ala Cys Ser Glu Glu Asp Ile Leu
        210                 215                 220

Arg Met Glu Leu Ile Ile Leu Lys Ala Leu Lys Trp Glu Leu Cys Pro
225                 230                 235                 240

Val Thr Ile Ile Ser Trp Leu Asn Leu Phe Leu Gln Val Asp Ala Leu
                245                 250                 255

Lys Asp Ala Pro Lys Val Leu Leu Pro Gln Tyr Ser Gln Glu Thr Phe
            260                 265                 270

Ile Gln Ile Ala Gln Leu Leu Asp Leu Cys Ile Leu Ala Ile Asp Ser
        275                 280                 285

Leu Glu Phe Gln Tyr Arg Ile Leu Thr Ala Ala Leu Cys His Phe
    290                 295                 300

Thr Ser Ile Glu Val Val Lys Lys Ala Ser Gly Leu Glu Trp Asp Ser
305                 310                 315                 320

Ile Ser Glu Cys Val Asp Trp Met Val Pro Phe Val Asn Val Lys
                325                 330                 335

Ser Thr Ser Pro Val Lys Leu Lys Thr Phe Lys Lys Ile Pro Met Glu
            340                 345                 350

Asp Arg His Asn Ile Gln Thr His Thr Asn Tyr Leu Ala Met Leu Glu
        355                 360                 365

Glu Val Asn Tyr Ile Asn Thr Phe Arg Lys Gly Gly Gln Leu Ser Pro
    370                 375                 380

Val Cys Asn Gly Gly Ile Met Thr Pro Pro Lys Ser Thr Glu Lys Pro
385                 390                 395                 400

Pro Gly Lys His

<210> SEQ ID NO 7
<211> LENGTH: 2613
<212> TYPE: DNA
<213> ORGANISM: Homo sapiens

<400> SEQUENCE: 7
agcgggtgcg gggcgggacc ggcccggcct atatattggg ttggcgccgg cgccagctga    60
gccgagcggt agctggtctg gcgaggtttt atacacctga agaagagaa tgtcaagacg     120 aagtagccgt ttacaagcta agcagcagcc ccagcccagc cagacggaat ccccccaaga   180
agcccagata tccaggcca agaagaggaa aactacccag gatgtcaaaa aagaagaga    240 ggaggtcacc aagaaacatc agtatgaaat taggaattgt tggccacctg tattatctgg   300
ggggatcagt ccttgcatta tcattgaaac acctcacaaa gaaataggaa caagtgattt   360
ctccagattt acaaattaca gatttaaaaa tcttttttatt aatccttcac ctttgcctga   420
tttaagctgg ggatgttcaa agaagtctg gctaaacatg ttaaaaaagg agagcagata    480
tgttcatgac aaacattttg aagttctgca ttctgacttg gaaccacaga tgaggtccat   540
acttctagac tggcttttag aggtatgtga agtatacaca cttcataggg aaacatttta    600
tcttgcttac gtcactgatg gtgcttgcag tgaagaggat atcttaagga tggaactcat    660
tatattaaag gctttaaaat gggaactttg tcctgtaaca atcatctcct ggctaaatct    720 cttctccaa gttgatgctc ttaaagatgc tcctaaagtt cttctacctc agtattctca     780
```

```
ggaaacattc attcaaatag ctcagctttt agatctgtgt attctagcca ttgattcatt      840
agagttccag tacagaatac tgactgctgc tgccttgtgc catttacct ccattgaagt        900 ggttaagaaa gcctcaggtt tggagtggga cagtatttca gaatgtgtag attggatggt      960
accttttgtc aatgtagtaa aaagtactag tccagtgaag ctgaagactt taagaagat      1020 tcctatggaa gacagacata atatccagac acatacaaac tatttggcta tgctggagga    1080
agtaaattac ataaacacct tcagaaaagg gggacagttg tcaccagtgt gcaatggagg    1140
cattatgaca ccaccgaaga gcactgaaaa accaccagga aaacactaaa gaagataact    1200
aagcaaacaa gttggaattc accaagattg ggtagaactg gtatcactga actactaaag    1260
ttttacagaa agtagtgctg tgattgattg ccctagccaa ttcacaagtt acactgccat    1320
tctgatttta aaacttacaa ttggcactaa agaatacatt taattatttc ctatgttagc    1380
tgttaaagaa acagcaggac ttgtttacaa agatgtcttc attcccaagg ttactgata    1440 gaagccaacc acagtctata ccatagcaat gttttccctt aatccagtg ttactgtgtt     1500 tatcttgata aactaggaat tttgtcactg gagttttgga ctggataagt gctaccttaa    1560
agggtatact aagtgataca gtactttgaa tctagttgtt agattctcaa aattcctaca    1620
ctcttgacta gtgcaatttg gttcttgaaa attaaattta aacttgttta caaaggttta    1680
gttttgtaat aaggtgacta atttatctat agctgctata gcaagctatt ataaaacttg    1740
aatttctaca aatggtgaaa tttaatgttt tttaaactag tttatttgcc ttgccataac    1800
acatttttta actaataagg cttagatgaa catggtgttc aacctgtgct ctaaacagtg    1860
ggagtaccaa agaaattata aacaagataa atgctgtggc tccttcctaa ctggggcttt    1920
cttgacatgt aggttgcttg gtaataacct ttttgtatat cacaatttgg gtgaaaaact    1980 taagtacccct ttcaaactat ttatatgagg aagtcacttt actactctaa gatatcccta   2040
aggaattttt ttttttaatt tagtgtgact aaggctttat ttatgtttgt gaaactgtta    2100
aggtcctttc taaattcctc cattgtgaga taaggacagt gtcaaagtga taagcttaa     2160 cacttgacct aaacttctat tttcttaagg aagaagagta ttaaatatat actgactcct    2220
agaaatctat ttattaaaaa aagacatgaa aacttgctgt acataggcta gctatttcta    2280
aatattttaa attagctttt ctaaaaaaaa atccagcct cataaagtag attagaaaac     2340
tagattgcta gtttatttg ttatcagata tgtgaatctc ttctcccttt gaagaaacta      2400
tacatttatt gttacggtat gaagtcttct gtatagtttg tttttaaact aatatttgtt    2460
tcagtatttt gtctgaaaag aaaacaccac taattgtgta catatgtatt atataaactt    2520
aaccttttaa tactgtttat ttttagccca ttgtttaaaa aataaaagtt aaaaaaattt    2580
aactgcttaa aagtaaaaaa aaaaaaaaaa aaa                                  2613

<210> SEQ ID NO 8
<211> LENGTH: 359
<212> TYPE: PRT
<213> ORGANISM: Homo sapiens

<400> SEQUENCE: 8

Met Ser Arg Arg Ser Ser Arg Leu Gln Ala Lys Gln Gln Pro Gln Pro
 1               5                  10                  15

Ser Gln Thr Glu Ser Pro Gln Glu Ala Gln Ile Ile Gln Ala Lys Lys
            20                  25                  30

Arg Lys Thr Thr Gln Asp Val Lys Lys Arg Arg Glu Glu Val Thr Lys
        35                  40                  45
```

```
Lys His Gln Tyr Glu Ile Arg Asn Cys Trp Pro Pro Val Leu Ser Gly
     50                  55                  60
Gly Ile Ser Pro Cys Ile Ile Glu Thr Pro His Lys Glu Ile Gly
65                  70                  75                  80
Thr Ser Asp Phe Ser Arg Phe Thr Asn Tyr Arg Phe Lys Asn Leu Phe
                85                  90                  95
Ile Asn Pro Ser Pro Leu Pro Asp Leu Ser Trp Gly Cys Ser Lys Glu
            100                 105                 110
Val Trp Leu Asn Met Leu Lys Lys Glu Ser Arg Tyr Val His Asp Lys
        115                 120                 125
His Phe Glu Val Leu His Ser Asp Leu Glu Pro Gln Met Arg Ser Ile
    130                 135                 140
Leu Leu Asp Trp Leu Leu Glu Val Cys Glu Val Tyr Thr Leu His Arg
145                 150                 155                 160
Glu Thr Phe Tyr Leu Ala Tyr Val Thr Asp Gly Ala Cys Ser Glu Glu
                165                 170                 175
Asp Ile Leu Arg Met Glu Leu Ile Ile Leu Lys Ala Leu Lys Trp Glu
            180                 185                 190
Leu Cys Pro Val Thr Ile Ile Ser Trp Leu Asn Leu Phe Leu Gln Val
        195                 200                 205
Asp Ala Leu Lys Asp Ala Pro Lys Val Leu Leu Pro Gln Tyr Ser Gln
    210                 215                 220
Glu Thr Phe Ile Gln Ile Ala Gln Leu Leu Asp Leu Cys Ile Leu Ala
225                 230                 235                 240
Ile Asp Ser Leu Glu Phe Gln Tyr Arg Ile Leu Thr Ala Ala Ala Leu
                245                 250                 255
Cys His Phe Thr Ser Ile Glu Val Val Lys Lys Ala Ser Gly Leu Glu
            260                 265                 270
Trp Asp Ser Ile Ser Glu Cys Val Asp Trp Met Val Pro Phe Val Asn
        275                 280                 285
Val Val Lys Ser Thr Ser Pro Val Lys Leu Lys Thr Phe Lys Lys Ile
    290                 295                 300
Pro Met Glu Asp Arg His Asn Ile Gln Thr His Thr Asn Tyr Leu Ala
305                 310                 315                 320
Met Leu Glu Glu Val Asn Tyr Ile Asn Thr Phe Arg Lys Gly Gly Gln
                325                 330                 335
Leu Ser Pro Val Cys Asn Gly Ile Met Thr Pro Pro Lys Ser Thr
            340                 345                 350
Glu Lys Pro Pro Gly Lys His
        355

<210> SEQ ID NO 9
<211> LENGTH: 2536
<212> TYPE: DNA
<213> ORGANISM: Homo sapiens

<400> SEQUENCE: 9
agcgggtgcg gggcgggacc ggcccggcct atatattggg ttggcgccgg cgccagctga        60
gccgagcggt agctggtctg gcgaggtttt atacacctga agaagagaaa tgtcaagacg       120
aagtagccgt ttacaagcta agcagcagcc ccagcccagc cagacggaat ccccccaaga       180
agcccagata atccaggcca agaagaggaa aactacccag gatgtcaaaa gaagtctggc       240
taaacatgtt aaaaaaggag agcagatatg ttcatgacaa acattttgaa gttctgcatt       300
```

```
ctgacttgga accacagatg aggtccatac ttctagactg gcttttagag gtatgtgaag    360
tatacacact tcatagggaa acattttatc ttgcacaaga cttttttgat agatttatgt    420
tgacacaaaa ggatataaat aaaaatatgc ttcaactcat tggaattacc tcattattca    480
ttgcttccaa acttgaggaa atctatgctc ctaaactcca agagtttgct tacgtcactg    540
atggtgcttg cagtgaagag gatatcttaa ggatggaact cattatatta aaggctttaa    600
aatgggaact ttgtcctgta acaatcatct cctggctaaa tctctttctc caagttgatg    660
ctcttaaaga tgctcctaaa gttcttctac ctcagtattc tcaggaaaca ttcattcaaa    720
tagctcagct tttagatctg tgtattctag ccattgattc attagagttc cagtacagaa    780
tactgactgc tgctgccttg tgccatttta cctccattga agtggttaag aaagcctcag    840
gtttggagtg ggacagtatt tcagaatgtg tagattggat ggtaccttt gtcaatgtag     900
taaaaagtac tagtccagtg aagctgaaga cttttaagaa gattcctatg gaagacagac    960
ataatatcca gacacataca aactatttgg ctatgctgga ggaagtaaat tacataaaca   1020
ccttcagaaa aggggagag ttgtcaccag tgtgcaatgg aggcattatg acaccaccga    1080
agagcactga aaaaccacca ggaaaacact aagaagata actaagcaaa caagttggaa    1140
ttcaccaaga ttgggtagaa ctggtatcac tgaactacta agttttaca gaaagtagtg     1200
ctgtgattga ttgccctagc caattcacaa gttacactgc cattctgatt ttaaaactta   1260
caattggcac taaagaatac atttaattat ttcctatgtt agctgttaaa gaaacagcag    1320
gacttgttta caaagatgtc ttcattccca aggttactgg atagaagcca accacagtct    1380
ataccatagc aatgtttttc ctttaatcca gtgttactgt gtttatcttg ataaactagg    1440
aattttgtca ctggagtttt ggactggata agtgctacct taaagggtat actaagtgat    1500
acagtacttt gaatctagtt gttagattct caaaattcct acactcttga ctagtgcaat    1560
ttggttcttg aaaattaaat ttaaacttgt ttacaaaggt ttagttttgt aataaggtga   1620
ctaatttatc tatagctgct atagcaagct attataaaac ttgaatttct acaaatggtg    1680
aaatttaatg ttttttaaac tagtttattt gccttgccat aacacatttt ttaactaata    1740
aggcttagat gaacatggtg ttcaacctgt gctctaaaca gtgggagtac caaagaaatt    1800
ataaacaaga taaatgctgt ggctccttcc taactggggc tttcttgaca tgtaggttgc    1860
ttggtaataa ccttttttgta tatcacaatt tgggtgaaaa acttaagtac cctttcaaac   1920
tatttatatg aggaagtcac tttactactc taagatatcc ctaaggaatt ttttttttta    1980
atttagtgtg actaaggctt tatttatgtt tgtgaaactg ttaaggtcct ttctaaattc    2040
ctccattgtg agataaggac agtgtcaaag tgataaagct taacacttga cctaaacttc    2100
tatttcttta aggaagaaga gtattaaata tatactgact cctagaaatc tatttattaa    2160
aaaaagacat gaaacttgc tgtacatagg ctagctattt ctaaatattt taaattagct     2220
tttctaaaaa aaaaatccag cctcataaag tagattagaa aactgactttg ctagtttatt   2280
ttgttatcag atatgtgaat ctcttctccc tttgaagaaa ctatacattt attgttacgg    2340
tatgaagtct tctgtatagt ttgttttta actaatattt gtttcagtat tttgtctgaa     2400
aagaaaacac cactaattgt gtacatatgt attatataaa cttaaccttt taatactgtt   2460
tattttagc ccattgttta aaaataaaa gttaaaaaaa tttaactgct taaagtaaa      2520
aaaaaaaaaa aaaaaa                                                   2536

<210> SEQ ID NO 10
<211> LENGTH: 296
```

```
<212> TYPE: PRT
<213> ORGANISM: Homo sapiens

<400> SEQUENCE: 10

Met Ser Lys Glu Val Trp Leu Asn Met Leu Lys Lys Glu Ser Arg Tyr
 1               5                  10                  15

Val His Asp Lys His Phe Glu Val Leu His Ser Asp Leu Glu Pro Gln
            20                  25                  30

Met Arg Ser Ile Leu Leu Asp Trp Leu Leu Glu Val Cys Glu Val Tyr
        35                  40                  45

Thr Leu His Arg Glu Thr Phe Tyr Leu Ala Gln Asp Phe Phe Asp Arg
    50                  55                  60

Phe Met Leu Thr Gln Lys Asp Ile Asn Lys Asn Met Leu Gln Leu Ile
65                  70                  75                  80

Gly Ile Thr Ser Leu Phe Ile Ala Ser Lys Leu Glu Glu Ile Tyr Ala
                85                  90                  95

Pro Lys Leu Gln Glu Phe Ala Tyr Val Thr Asp Gly Ala Cys Ser Glu
            100                 105                 110

Glu Asp Ile Leu Arg Met Glu Leu Ile Ile Leu Lys Ala Leu Lys Trp
        115                 120                 125

Glu Leu Cys Pro Val Thr Ile Ile Ser Trp Leu Asn Leu Phe Leu Gln
    130                 135                 140

Val Asp Ala Leu Lys Asp Ala Pro Lys Val Leu Leu Pro Gln Tyr Ser
145                 150                 155                 160

Gln Glu Thr Phe Ile Gln Ile Ala Gln Leu Leu Asp Leu Cys Ile Leu
                165                 170                 175

Ala Ile Asp Ser Leu Glu Phe Gln Tyr Arg Ile Leu Thr Ala Ala Ala
            180                 185                 190

Leu Cys His Phe Thr Ser Ile Glu Val Val Lys Lys Ala Ser Gly Leu
        195                 200                 205

Glu Trp Asp Ser Ile Ser Glu Cys Val Asp Trp Met Val Pro Phe Val
    210                 215                 220

Asn Val Val Lys Ser Thr Ser Pro Val Lys Leu Lys Thr Phe Lys Lys
225                 230                 235                 240

Ile Pro Met Glu Asp Arg His Asn Ile Gln Thr His Thr Asn Tyr Leu
                245                 250                 255

Ala Met Leu Glu Glu Val Asn Tyr Ile Asn Thr Phe Arg Lys Gly Gly
            260                 265                 270

Gln Leu Ser Pro Val Cys Asn Gly Gly Ile Met Thr Pro Pro Lys Ser
        275                 280                 285

Thr Glu Lys Pro Pro Gly Lys His
    290                 295

<210> SEQ ID NO 11
<211> LENGTH: 3453
<212> TYPE: DNA
<213> ORGANISM: Homo sapiens

<400> SEQUENCE: 11 actttctcgcg cgaaacctgg ttgttgctgt agtggcggag aggatcgtgg tactgctatg      60
gcggaatcat cggaatcctt caccatggca tccagcccgg cccagcgtcg gcgaggcaat     120
gatcctctca cctccagccc tggccgaagc tcccggcgta ctgatgccct cacctccagc     180
cctggccgtg accttccacc atttgaggat gagtccgagg ggctcctagg cacagagggg     240
cccctggagg aagaagagga tgagaggag ctcattggag atggcatgga aagggactac     300
```

-continued

| | |
|---|---|
| cgcgccatcc cagagctgga cgcctatgag gccgagggac tggctctgga tgatgaggac | 360 |
| gtagaggagc tgacggccag tcagagggag gcagcagagc gggccatgcg cagcgtgac | 420 |
| cgggaggctg gccggggcct gggccgcatg cgccgtgggc tcctgtatga cagcgatgag | 480 |
| gaggacgagg agcgccctgc ccgcaagcgc cgccaggtgg agcgggccac ggaggacggc | 540 |
| gaggaggacg aggagatgat cgagagcatc gagaacctgg aggatctcaa aggccactct | 600 |
| gtgcgcgagt gggtgagcat ggcgggcccc cggctggaga tccaccaccg cttcaagaac | 660 |
| ttcctgcgca ctcacgtcga cagccacggc acaacgtct tcaaggagcg catcagcgac | 720 |
| atgtgcaaag agaaccgtga gagcctggtg gtgaactatg aggacttggc agccagggag | 780 |
| cacgtgctgg cctacttcct gcctgaggca ccggcggagc tgctgcagat ctttgatgag | 840 |
| gctgccctgg aggtggtact ggccatgtac cccaagtacg accgcatcac caaccacatc | 900 |
| catgtccgca tctcccacct gcctctggtg gaggagctgc gctcgctgag gcagctgcat | 960 |
| ctgaaccagc tgatccgcac cagtggggtg gtgaccagct gcactggcgt cctgccccag | 1020 |
| ctcagcatgg tcaagtacaa ctgcaacaag tgcaatttcg tcctgggtcc tttctgccag | 1080 |
| tcccagaacc aggaggtgaa accaggctcc tgtcctgagt gccagtcggc cggcccctttt | 1140 |
| gaggtcaaca tggaggagac catctatcag aactaccagc gtatccgaat ccaggagagt | 1200 |
| ccaggcaaag tggcggctgg ccggctgccc cgctccaagg acgccattct cctgcagat | 1260 |
| ctggtgaca gctgcaagcc aggagacgag atagagctga ctggcatcta tcacaacaac | 1320 |
| tatgatggct ccctcaacac tgccaatggc ttccctgtct tgccactgt catcctagcc | 1380 |
| aaccacgtgg ccaagaagga caacaaggtt gctgtagggg aactgaccga tgaagatgtg | 1440 |
| aagatgatca ctagcctctc caaggatcag cagatcggag agaagatctt tgccagcatt | 1500 |
| gctccttcca tctatggtca tgaagacatc aagagaggcc tggctctggc cctgttcgga | 1560 |
| ggggagccca aaaacccagg tggcaagcac aaggtacgtg tgatatcaa cgtgctcttg | 1620 |
| tgcggagacc ctggcacagc gaagtcgcag tttctcaagt atattgagaa agtgtccagc | 1680 |
| cgagccatct tcaccactgg ccaggggcg tcggctgtgg gcctcacggc gtatgtccag | 1740 |
| cggcaccctg tcagcaggga gtggaccttg gaggctgggg ccctggttct ggctgaccga | 1800 |
| ggagtgtgtc tcattgatga atttgacaag atgaatgacc aggacagaac cagcatccat | 1860 |
| gaggccatgg agcaacagag catctccatc tcgaaggctg gcatcgtcac ctccctgcag | 1920 |
| gctcgctgca cggtcattgc tgccgccaac cccataggag ggcgctacga cccctcgctg | 1980 |
| actttctctg agaacgtgga cctcacagag cccatcatct cacgctttga catcctgtgt | 2040 |
| gtggtgaggg acaccgtgga cccagtccag gacgagatgc tggcccgctt cgtggtgggc | 2100 |
| agccacgtca gacaccaccc cagcaacaag gaggaggagg ggctggccaa tggcagcgct | 2160 |
| gctgagcccg ccatgcccaa cacgtatggc gtggagcccc tgcccccagga ggtcctgaag | 2220 |
| aagtacatca tctacgccaa ggagagggtc cacccgaagc tcaaccagat ggaccaggac | 2280 |
| aaggtggcca agatgtacag tgacctgagg aaagaatcta tggcgacagg cagcatcccc | 2340 |
| attacggtgc ggcacatcga gtccatgatc cgcatggcgg aggcccacgc gcgcatccat | 2400 |
| ctgcgggact atgtgatcga agacgacgtc aacatggcca tccgcgtgat gctggagagc | 2460 |
| ttcatagaca cacagaagtt cagcgtcatg cgcagcatgc gcaagacttt tgcccgctac | 2520 |
| cttttcattcc ggcgtgacaa caatgagctg ttgctcttca tactgaagca gttagtggca | 2580 |
| gagcaggtga catatcagcg caaccgcttt ggggcccagc aggacactat tgaggtccct | 2640 |

```
gagaaggact tggtggataa ggctcgtcag atcaacatcc acaacctctc tgcatttat     2700 gacagtgagc tcttcaggat gaacaagttc agccacgacc tgaaaaggaa aatgatcctg    2760
cagcagttct gaggccctat gccatccata aggattcctt gggattctgg tttggggtgg    2820
tcagtgccct ctgtgcttta tggacacaaa accagagcac ttgatgaact cggggtacta    2880
gggtcagggc ttatagcagg atgtctggct gcacctggca tgactgtttg tttctccaag    2940
cctgctttgt gcttctcacc tttgggtggg atgccttgcc agtgtgtctt acttggttgc    3000
tgaacatctt gccacctccg agtgctttgt ctccactcag taccttggat cagagctgct    3060
gagttcagga tgcctgcgtg tggtttaggt gttagccttc ttacatggat gtcaggagag    3120
ctgctgccct cttggcgtga gttgcgtatt caggctgctt ttgctgcctt tggccagaga    3180
gctggttgaa gatgtttgta atcgttttca gtctcctgca ggtttctgtg ccctgtggt    3240 ggaagagggc acgacagtgc agcgcagcg ttctgggctc ctcagtcgca ggggtgggat    3300
gtgagtcatg cggattatcc actgccaca gttatcagct gccattgctc cctgtctgtt    3360
tccccactct cttatttgtg cattcggttt ggtttctgta gttttaattt ttaataaagt    3420
tgaataaaat ataaaaaaaa aaaaaaaaa aaa                                  3453
```

<210> SEQ ID NO 12
<211> LENGTH: 904
<212> TYPE: PRT
<213> ORGANISM: Homo sapiens

<400> SEQUENCE: 12

```
Met Ala Glu Ser Ser Glu Ser Phe Thr Met Ala Ser Ser Pro Ala Gln
  1               5                   10                  15

Arg Arg Arg Gly Asn Asp Pro Leu Thr Ser Ser Pro Gly Arg Ser Ser
             20                  25                  30

Arg Arg Thr Asp Ala Leu Thr Ser Ser Pro Gly Arg Asp Leu Pro Pro
         35                  40                  45

Phe Glu Asp Glu Ser Glu Gly Leu Leu Gly Thr Gly Pro Leu Glu
     50                  55                  60

Glu Glu Glu Asp Gly Glu Leu Ile Gly Asp Gly Met Glu Arg Asp
 65                  70                  75                  80

Tyr Arg Ala Ile Pro Glu Leu Asp Ala Tyr Glu Ala Glu Gly Leu Ala
                 85                  90                  95

Leu Asp Asp Glu Asp Val Glu Glu Leu Thr Ala Ser Gln Arg Glu Ala
            100                 105                 110

Ala Glu Arg Ala Met Arg Gln Arg Asp Arg Glu Ala Gly Arg Gly Leu
        115                 120                 125

Gly Arg Met Arg Arg Gly Leu Leu Tyr Asp Ser Asp Glu Glu Asp Glu
    130                 135                 140

Glu Arg Pro Ala Arg Lys Arg Arg Gln Val Glu Arg Ala Thr Glu Asp
145                 150                 155                 160

Gly Glu Glu Asp Glu Glu Met Ile Glu Ser Ile Glu Asn Leu Glu Asp
                165                 170                 175

Leu Lys Gly His Ser Val Arg Glu Trp Val Ser Met Ala Gly Pro Arg
            180                 185                 190

Leu Glu Ile His His Arg Phe Lys Asn Phe Leu Arg Thr His Val Asp
        195                 200                 205

Ser His Gly His Asn Val Phe Lys Glu Arg Ile Ser Asp Met Cys Lys
    210                 215                 220

Glu Asn Arg Glu Ser Leu Val Val Asn Tyr Glu Asp Leu Ala Ala Arg
```

-continued

```
            225                 230                 235                 240
Glu His Val Leu Ala Tyr Phe Leu Pro Glu Ala Pro Ala Glu Leu Leu
                245                 250                 255
Gln Ile Phe Asp Glu Ala Ala Leu Glu Val Val Leu Ala Met Tyr Pro
                260                 265                 270
Lys Tyr Asp Arg Ile Thr Asn His Ile His Val Arg Ile Ser His Leu
                275                 280                 285
Pro Leu Val Glu Glu Leu Arg Ser Leu Arg Gln Leu His Leu Asn Gln
                290                 295                 300
Leu Ile Arg Thr Ser Gly Val Val Thr Ser Cys Thr Gly Val Leu Pro
305                 310                 315                 320
Gln Leu Ser Met Val Lys Tyr Asn Cys Asn Lys Cys Asn Phe Val Leu
                325                 330                 335
Gly Pro Phe Cys Gln Ser Gln Asn Gln Glu Val Lys Pro Gly Ser Cys
                340                 345                 350
Pro Glu Cys Gln Ser Ala Gly Pro Phe Glu Val Asn Met Glu Glu Thr
                355                 360                 365
Ile Tyr Gln Asn Tyr Gln Arg Ile Arg Ile Gln Glu Ser Pro Gly Lys
                370                 375                 380
Val Ala Ala Gly Arg Leu Pro Arg Ser Lys Asp Ala Ile Leu Leu Ala
385                 390                 395                 400
Asp Leu Val Asp Ser Cys Lys Pro Gly Asp Glu Ile Glu Leu Thr Gly
                405                 410                 415
Ile Tyr His Asn Asn Tyr Asp Gly Ser Leu Asn Thr Ala Asn Gly Phe
                420                 425                 430
Pro Val Phe Ala Thr Val Ile Leu Ala Asn His Val Ala Lys Lys Asp
                435                 440                 445
Asn Lys Val Ala Val Gly Glu Leu Thr Asp Glu Asp Val Lys Met Ile
                450                 455                 460
Thr Ser Leu Ser Lys Asp Gln Gln Ile Gly Glu Lys Ile Phe Ala Ser
465                 470                 475                 480
Ile Ala Pro Ser Ile Tyr Gly His Glu Asp Ile Lys Arg Gly Leu Ala
                485                 490                 495
Leu Ala Leu Phe Gly Gly Glu Pro Lys Asn Pro Gly Gly Lys His Lys
                500                 505                 510
Val Arg Gly Asp Ile Asn Val Leu Leu Cys Gly Asp Pro Gly Thr Ala
                515                 520                 525
Lys Ser Gln Phe Leu Lys Tyr Ile Glu Lys Val Ser Ser Arg Ala Ile
                530                 535                 540
Phe Thr Thr Gly Gln Gly Ala Ser Ala Val Gly Leu Thr Ala Tyr Val
545                 550                 555                 560
Gln Arg His Pro Val Ser Arg Glu Trp Thr Leu Glu Ala Gly Ala Leu
                565                 570                 575
Val Leu Ala Asp Arg Gly Val Cys Leu Ile Asp Glu Phe Asp Lys Met
                580                 585                 590
Asn Asp Gln Asp Arg Thr Ser Ile His Glu Ala Met Glu Gln Gln Ser
                595                 600                 605
Ile Ser Ile Ser Lys Ala Gly Ile Val Thr Ser Leu Gln Ala Arg Cys
                610                 615                 620
Thr Val Ile Ala Ala Ala Asn Pro Ile Gly Gly Arg Tyr Asp Pro Ser
625                 630                 635                 640
Leu Thr Phe Ser Glu Asn Val Asp Leu Thr Glu Pro Ile Ile Ser Arg
                645                 650                 655
```

-continued

```
Phe Asp Ile Leu Cys Val Val Arg Asp Thr Val Asp Pro Val Gln Asp
            660                 665                 670
Glu Met Leu Ala Arg Phe Val Val Gly Ser His Val Arg His His Pro
        675                 680                 685
Ser Asn Lys Glu Glu Gly Leu Ala Asn Gly Ser Ala Glu Pro
        690                 695                 700
Ala Met Pro Asn Thr Tyr Gly Val Glu Pro Leu Pro Gln Glu Val Leu
705                 710                 715                 720
Lys Lys Tyr Ile Ile Tyr Ala Lys Glu Arg Val His Pro Lys Leu Asn
                725                 730                 735
Gln Met Asp Gln Asp Lys Val Ala Lys Met Tyr Ser Asp Leu Arg Lys
            740                 745                 750
Glu Ser Met Ala Thr Gly Ser Ile Pro Ile Thr Val Arg His Ile Glu
        755                 760                 765
Ser Met Ile Arg Met Ala Glu Ala His Ala Arg Ile His Leu Arg Asp
        770                 775                 780
Tyr Val Ile Glu Asp Asp Val Asn Met Ala Ile Arg Val Met Leu Glu
785                 790                 795                 800
Ser Phe Ile Asp Thr Gln Lys Phe Ser Val Met Arg Ser Met Arg Lys
                805                 810                 815
Thr Phe Ala Arg Tyr Leu Ser Phe Arg Arg Asp Asn Asn Glu Leu Leu
            820                 825                 830
Leu Phe Ile Leu Lys Gln Leu Val Ala Glu Gln Val Thr Tyr Gln Arg
        835                 840                 845
Asn Arg Phe Gly Ala Gln Gln Asp Thr Ile Glu Val Pro Glu Lys Asp
        850                 855                 860
Leu Val Asp Lys Ala Arg Gln Ile Asn Ile His Asn Leu Ser Ala Phe
865                 870                 875                 880
Tyr Asp Ser Glu Leu Phe Arg Met Asn Lys Phe Ser His Asp Leu Lys
                885                 890                 895
Arg Lys Met Ile Leu Gln Gln Phe
            900
```

<210> SEQ ID NO 13
<211> LENGTH: 2821
<212> TYPE: DNA
<213> ORGANISM: Homo sapiens

<400> SEQUENCE: 13

```
cgcccttcc cagccccaag ggtctaggat acagtctttg tagatgagcg ggtccccctt    60
ggaggacaga atgaagaatt gggaaatcat ggccgttctg gagagtagac aagaagacgg   120
cgaaagtcgg gcctgccccg ccctgcggcc ccggaacaaa agaacgcgtg tgcgctggcc   180
ctttaagagc gattctcctc cgcccgcgcc agctcggacc gcgggaaacc cggcgcctgc   240
actacccgc ccggagattc ccttccgacg cccgcaccgc ctcccgtca ctcattctag    300
gcccgcacgg tgattggctt gcggctagcg ggaggtgaag aaggccgcct tgtccgattg   360
gcccgcacgc agtggcgccg gtcacgtggg gggcgacgtt tcgcgccaat ttcggttggc   420
cggccacagt ccaccgcgcg gagattctca gcttccccag gagcaagacc tctgagcccg   480
ccaagcgcgg ccgcacggcc ctcggcagcg atggcactga aggactacgc gctagagaag   540
gaaaaggtta agaagttctt acaagagttc taccaggatg atgaactcgg gaagaagcag   600
ttcaagtatg ggaaccagtt ggttcggctg gctcatcggg aacaggtggc tctgtatgtg   660
```

```
gacctggacg acgtagccga ggatgacccc gagttggtgg actcaatttg tgagaatgcc    720
aggcgctacg cgaagctctt tgctgatgcc gtacaagagc tgctgcctca gtacaaggag    780
agggaagtgg taaataaaga tgtcctggac gtttacattg agcatcggct aatgatggag    840
cagcggagtc gggaccctgg gatggtccga agcccccaga accagtaccc tgctgaactc    900
atgcgcagat ttgagctgta ttttcaaggc cctagcagca caagcctcg tgtgatccgg     960
gaagtgcggg ctgactctgt ggggaagttg gtaactgtgc gtggaatcgt cactcgtgtc   1020
tctgaagtca aacccaagat ggtggtggcc acttacactt gtgaccagtg tggggcagag   1080
acctaccagc cgatccagtc tcccactttc atgcctctga tcatgtgccc aagccaggag   1140
tgccaaaacca accgctcagg agggcggctg tatctgcaga cacggggctc cagattcatc   1200
aaattccagg agatgaagat gcaagaacat agtgatcagg tgcctgtggg aaatatccct   1260
cgtagtatca cggtgctggt agaaggagag aacacaagga ttgcccagcc tggagaccac   1320
gtcagcgtca ctggtatttt cttgccaatc ctgcgcactg ggttccgaca ggtggtacag   1380
ggtttactct cagaaaccta cctggaagcc catcggattg tgaagatgaa caagagtgag   1440
gatgatgagt ctggggctgg agagctcacc agggaggagc tgaggcaaat tgcagaggag   1500
gatttctacg aaaagctggc agcttcaatc gccccagaaa tatacgggca tgaagatgtg   1560
aagaaggcac tgctgctcct gctagtcggg ggtgtggacc agtctcctcg aggcatgaaa   1620
atccggggca acatcaacat ctgtctgatg ggggatcctg tgtggccaa gtctcagctc    1680
ctgtcataca ttgatcgact ggcgcctcgc agccagtaca caacaggccg ggctcctca    1740
ggagtggggc ttacggcagc tgtgctgaga gactccgtga gtggagaact gaccttagag   1800
ggtgggccc tggtgctggc tgaccagggt gtgtgctgca ttgatgagtt cgacaagatg    1860
gctgaggccg accgcacagc catccacgag gtcatggagc agcagaccat ctccattgcc   1920
aaggccggca ttctcaccac actcaatgcc cgctgctcca tcctggctgc cgccaaccct   1980
gcctacgggc gctacaaccc tcgccgcagc ctggagcaga acatacagct acctgctgca   2040
ctgctctccc ggtttgacct cctctggctg attcaggacc ggcccgaccg agacaatgac   2100
ctacggttgg cccagcacat cacctatgtg caccagcaca gccggcagcc cccctcccag   2160
tttgaacctc tggacatgaa gctcatgagg cgttacatag ccatgtgccg cgagaagcag   2220
cccatggtgc cagagtctct ggctgactac atcacagcag catacgtgga gatgaggcga   2280
gaggcttggg ctagtaagga tgccacctat acttctgccc ggaccctgct ggctatcctg   2340
cgcctttcca ctgctctggc acgtctgaga atggtggatg tggtgagaa agaagatgtg    2400
aatgaagcca tcaggctaat ggagatgtca aaggactctc ttctaggaga caaggggcag   2460
acagctagga ctcagagacc agcagatgtg atatttgcca ccgtccgtga actggtctca   2520
ggggccgaa gtgtccggtt ctctgaggca gagcagcgct gtgtatctcg tggcttcaca   2580
cccgcccagt tccaggcggc tctggatgaa tatgaggagc tcaatgtctg gcaggtcaat   2640
gcttcccgga cacggatcac ttttgtctga ttccagcctg cttgcaaccc tggggtcctc   2700
ttgttccctg ctggcctgcc ccttgggaag gggcagtgat gcctttgagg ggaaggagga   2760
gcccctcttt ctcccatgct gcacttactc cttttgctaa taaaagtgtt tgtagattgt   2820
c                                                                   2821
```

<210> SEQ ID NO 14
<211> LENGTH: 719
<212> TYPE: PRT
<213> ORGANISM: Homo sapiens

<400> SEQUENCE: 14

```
Met Ala Leu Lys Asp Tyr Ala Leu Glu Lys Glu Lys Val Lys Lys Phe
1               5                   10                  15
Leu Gln Glu Phe Tyr Gln Asp Glu Leu Gly Lys Lys Gln Phe Lys
            20                  25                  30
Tyr Gly Asn Gln Leu Val Arg Leu Ala His Arg Glu Gln Val Ala Leu
        35                  40                  45
Tyr Val Asp Leu Asp Asp Val Ala Glu Asp Pro Glu Leu Val Asp
    50                  55                  60
Ser Ile Cys Glu Asn Ala Arg Arg Tyr Ala Lys Leu Phe Ala Asp Ala
65                  70                  75                  80
Val Gln Glu Leu Leu Pro Gln Tyr Lys Glu Arg Glu Val Val Asn Lys
                85                  90                  95
Asp Val Leu Asp Val Tyr Ile Glu His Arg Leu Met Met Glu Gln Arg
            100                 105                 110
Ser Arg Asp Pro Gly Met Val Arg Ser Pro Gln Asn Gln Tyr Pro Ala
            115                 120                 125
Glu Leu Met Arg Arg Phe Glu Leu Tyr Phe Gln Gly Pro Ser Ser Asn
        130                 135                 140
Lys Pro Arg Val Ile Arg Glu Val Arg Ala Asp Ser Val Gly Lys Leu
145                 150                 155                 160
Val Thr Val Arg Gly Ile Val Thr Arg Val Ser Glu Val Lys Pro Lys
                165                 170                 175
Met Val Val Ala Thr Tyr Thr Cys Asp Gln Cys Gly Ala Glu Thr Tyr
            180                 185                 190
Gln Pro Ile Gln Ser Pro Thr Phe Met Pro Leu Ile Met Cys Pro Ser
        195                 200                 205
Gln Glu Cys Gln Thr Asn Arg Ser Gly Gly Arg Leu Tyr Leu Gln Thr
    210                 215                 220
Arg Gly Ser Arg Phe Ile Lys Phe Gln Glu Met Lys Met Gln Glu His
225                 230                 235                 240
Ser Asp Gln Val Pro Val Gly Asn Ile Pro Arg Ser Ile Thr Val Leu
                245                 250                 255
Val Glu Gly Glu Asn Thr Arg Ile Ala Gln Pro Gly Asp His Val Ser
            260                 265                 270
Val Thr Gly Ile Phe Leu Pro Ile Leu Arg Thr Gly Phe Arg Gln Val
        275                 280                 285
Val Gln Gly Leu Leu Ser Glu Thr Tyr Leu Glu Ala His Arg Ile Val
    290                 295                 300
Lys Met Asn Lys Ser Glu Asp Glu Ser Gly Ala Gly Glu Leu Thr
305                 310                 315                 320
Arg Glu Glu Leu Arg Gln Ile Ala Glu Glu Asp Phe Tyr Glu Lys Leu
                325                 330                 335
Ala Ala Ser Ile Ala Pro Glu Ile Tyr Gly His Glu Asp Val Lys Lys
            340                 345                 350
Ala Leu Leu Leu Leu Val Gly Gly Val Asp Gln Ser Pro Arg Gly
        355                 360                 365
Met Lys Ile Arg Gly Asn Ile Asn Ile Cys Leu Met Gly Asp Pro Gly
    370                 375                 380
Val Ala Lys Ser Gln Leu Leu Ser Tyr Ile Asp Arg Leu Ala Pro Arg
385                 390                 395                 400
Ser Gln Tyr Thr Thr Gly Arg Gly Ser Ser Gly Val Gly Leu Thr Ala
```

```
                    405                 410                 415
Ala Val Leu Arg Asp Ser Val Ser Gly Glu Leu Thr Leu Glu Gly Gly
                420                 425                 430

Ala Leu Val Leu Ala Asp Gln Gly Val Cys Cys Ile Asp Glu Phe Asp
            435                 440                 445

Lys Met Ala Glu Ala Asp Arg Thr Ala Ile His Glu Val Met Glu Gln
    450                 455                 460

Gln Thr Ile Ser Ile Ala Lys Ala Gly Ile Leu Thr Thr Leu Asn Ala
465                 470                 475                 480

Arg Cys Ser Ile Leu Ala Ala Asn Pro Ala Tyr Gly Arg Tyr Asn
                485                 490                 495

Pro Arg Arg Ser Leu Glu Gln Asn Ile Gln Leu Pro Ala Ala Leu Leu
            500                 505                 510

Ser Arg Phe Asp Leu Leu Trp Leu Ile Gln Asp Arg Pro Asp Arg Asp
    515                 520                 525

Asn Asp Leu Arg Leu Ala Gln His Ile Thr Tyr Val His Gln His Ser
530                 535                 540

Arg Gln Pro Pro Ser Gln Phe Glu Pro Leu Asp Met Lys Leu Met Arg
545                 550                 555                 560

Arg Tyr Ile Ala Met Cys Arg Glu Lys Gln Pro Met Val Pro Glu Ser
                565                 570                 575

Leu Ala Asp Tyr Ile Thr Ala Ala Tyr Val Glu Met Arg Arg Glu Ala
            580                 585                 590

Trp Ala Ser Lys Asp Ala Thr Tyr Thr Ser Ala Arg Thr Leu Leu Ala
    595                 600                 605

Ile Leu Arg Leu Ser Thr Ala Leu Ala Arg Leu Arg Met Val Asp Val
610                 615                 620

Val Glu Lys Glu Asp Val Asn Glu Ala Ile Arg Leu Met Glu Met Ser
625                 630                 635                 640

Lys Asp Ser Leu Leu Gly Asp Lys Gly Gln Thr Ala Arg Thr Gln Arg
                645                 650                 655

Pro Ala Asp Val Ile Phe Ala Thr Val Arg Glu Leu Val Ser Gly Gly
            660                 665                 670

Arg Ser Val Arg Phe Ser Glu Ala Glu Gln Arg Cys Val Ser Arg Gly
    675                 680                 685

Phe Thr Pro Ala Gln Phe Gln Ala Ala Leu Asp Glu Tyr Glu Glu Leu
690                 695                 700

Asn Val Trp Gln Val Asn Ala Ser Arg Thr Arg Ile Thr Phe Val
705                 710                 715

<210> SEQ ID NO 15
<211> LENGTH: 2900
<212> TYPE: DNA
<213> ORGANISM: Homo sapiens

<400> SEQUENCE: 15
agtgtcgtgt aaacagtgtc cttccgcgcg gcggccgcgg agagagctgc ggcccggggg    60
ggcgtgcctg ggatccggag cttcgctcgg gcccgggaaa ggcggcagtg ggctgggatc   120
gcggtgtctc tgggtgtgat ggccaatggc tggactggct cccgccctgg gcggaggaat   180
cccgagctgt gaagcggctg gaatccgggc ccatgtgctt ctttgtttac taagagcgga   240
agcgatggcg ggagcggggg tggggtgcgg tggcggggtg cggtggcgga ggtcccggtg   300
aaatcagggg ctaaggggac ccaaagaagg cggggggatca taggggtgga aagaaagctg   360
```

```
agaaccttga gaccggagtg tgagggccca acggggaagg gcgctagaat tttaaactaa    420
agtagggacc ggaattcccc tggggagatg ttggatggcc ctgtgcactg ccacgggctc    480
tttattcttc gctggttaga aacagacttg tgaaaaagag ttatgcccac tttggggaga    540
cttcgaaaag gttaagaagt tcttacaaga gttctaccag gatgatgaac tcgggaagaa    600
gcagttcaag tatgggaacc agttggttcg gctggctcat cgggaacagg tggctctgta    660
tgtggacctg gacgacgtag ccgaggatga ccccgagttg gtggactcaa tttgtgagaa    720
tgccaggcgc tacgcgaagc tctttgctga tgccgtacaa gagctgctgc ctcagtacaa    780
ggagagggaa gtggtaaata aagatgtcct ggacgtttac attgagcatc ggctaatgat    840
ggagcagcgg agtcgggacc ctgggatggt ccgaagcccc cagaaccagt accctgctga    900
actcatgcgc agattgtgag tggtctctgt cgggaaagat gtagggattg gttctccagg    960
atcttgtttg tgactgtttt ctccccttag tgagctgtat tttcaaggcc ctagcagcaa   1020
caagcctcgt gtgatccggg aagtgcgggc tgactctgtg gggaagttgg taactgtgcg   1080
tggaatcgtc actcgtgtct ctgaagtcaa acccaagatg gtggtggcca cttacacttg   1140
tgaccagtgt ggggcagaga cctaccagcc gatccagtct cccactttca tgcctctgat   1200
catgtgccca agccaggagt gccaaaccaa ccgctcagga gggcggctgt atctgcagac   1260
acggggctcc agattcatca aattccagga gatgaagatg caagaacata gtgatcaggt   1320
gcctgtggga aatatccctc gtagtatcac ggtgctggta aaggagagag acacaaggat   1380
tgcccagcct ggagaccacg tcagcgtcac tggtattttc ttgccaatcc tgcgcactgg   1440
gttccgacag gtggtacagg gtttactctc agaaacctac ctggaagccc atcggattgt   1500
gaagatgaac aagagtgagg atgatgagtc tggggctgga gagctcacca gggaggagct   1560
gaggcaaatt gcagaggagg atttctacga aaagctggca gcttcaatcg ccccagaaat   1620
atacgggcat gaagatgtga agaaggcact gctgctcctg ctagtcgggg gtgtggacca   1680
gtctcctcga ggcatgaaaa tccggggcaa catcaacatc tgtctgatgg gggatcctgg   1740
tgtggccaag tctcagctcc tgtcatacat tgatcgactg gcgcctcgca gccagtacac   1800
aacaggccgg ggctcctcag gagtggggct tacggcagct gtgctgagag actccgtgag   1860
tggagaactg accttagagg gtggggccct ggtgctggct gaccagggtg tgtgctgcat   1920
tgatgagttc gacaagatgg ctgaggccga ccgcacagcc atccacgagg tcatggagca   1980
gcagaccatc tccattgcca aggccggcat tctcaccaca ctcaatgccc gctgctccat   2040
cctggctgcc gccaaccctg cctacgggcg ctacaaccct cgccgcagcc tggagcagaa   2100
catacagcta cctgctgcac tgctctcccg gtttgacctc ctctggctga ttcaggaccg   2160
gcccgaccga gacaatgacc tacggttggc ccagcacatc acctatgtgc accagcacag   2220
ccggcagccc ccctcccagt ttgaacctct ggacatgaag ctcatgaggc gttacatagc   2280
catgtgccgc gagaagcagc ccatggtgcc agagtctctg gctgactaca tcacagcagc   2340
atacgtggag atgaggcgag aggcttgggc tagtaaggat gccacctata cttctgcccg   2400
gaccctgctg ctatcctgc gccttttccac tgctctggca cgtctgagaa tggtggatgt   2460
ggtggagaaa gaagatgtga atgaagccat caggctaatg gagatgtcaa aggactctct   2520
tctaggagac aaggggcaga cagctaggac tcagagacca gcagatgtga tatttgccac   2580
cgtccgtgaa ctggtctcag ggggccgaag tgtccggttc tctgaggcag agcagcgctg   2640
tgtatctcgt ggcttcacac ccgcccagtt ccaggcggct ctggatgaat atgaggagct   2700
caatgtctgg caggtcaatg cttcccggac acggatcact tttgtctgat tccagcctgc   2760
```

-continued

```
ttgcaaccct gggtcctct tgttccctgc tggcctgccc cttgggaagg ggcagtgatg    2820
cctttgaggg gaaggaggag ccctctttc tccatgctg cacttactcc ttttgctaat    2880
aaaagtgttt gtagattgtc                                               2900
```

<210> SEQ ID NO 16
<211> LENGTH: 543
<212> TYPE: PRT
<213> ORGANISM: Homo sapiens

<400> SEQUENCE: 16

```
Met Val Val Ala Thr Tyr Thr Cys Asp Gln Cys Gly Ala Glu Thr Tyr
 1               5                  10                  15

Gln Pro Ile Gln Ser Pro Thr Phe Met Pro Leu Ile Met Cys Pro Ser
            20                  25                  30

Gln Glu Cys Gln Thr Asn Arg Ser Gly Gly Arg Leu Tyr Leu Gln Thr
        35                  40                  45

Arg Gly Ser Arg Phe Ile Lys Phe Gln Glu Met Lys Met Gln Glu His
    50                  55                  60

Ser Asp Gln Val Pro Val Gly Asn Ile Pro Arg Ser Ile Thr Val Leu
65                  70                  75                  80

Val Glu Gly Glu Asn Thr Arg Ile Ala Gln Pro Gly Asp His Val Ser
                85                  90                  95

Val Thr Gly Ile Phe Leu Pro Ile Leu Arg Thr Gly Phe Arg Gln Val
            100                 105                 110

Val Gln Gly Leu Leu Ser Glu Thr Tyr Leu Glu Ala His Arg Ile Val
        115                 120                 125

Lys Met Asn Lys Ser Glu Asp Asp Glu Ser Gly Ala Gly Glu Leu Thr
    130                 135                 140

Arg Glu Glu Leu Arg Gln Ile Ala Glu Glu Asp Phe Tyr Glu Lys Leu
145                 150                 155                 160

Ala Ala Ser Ile Ala Pro Glu Ile Tyr Gly His Glu Asp Val Lys Lys
                165                 170                 175

Ala Leu Leu Leu Leu Val Gly Gly Val Asp Gln Ser Pro Arg Gly
            180                 185                 190

Met Lys Ile Arg Gly Asn Ile Asn Ile Cys Leu Met Gly Asp Pro Gly
        195                 200                 205

Val Ala Lys Ser Gln Leu Leu Ser Tyr Ile Asp Arg Leu Ala Pro Arg
    210                 215                 220

Ser Gln Tyr Thr Thr Gly Arg Gly Ser Ser Gly Val Gly Leu Thr Ala
225                 230                 235                 240

Ala Val Leu Arg Asp Ser Val Ser Gly Glu Leu Thr Leu Glu Gly Gly
                245                 250                 255

Ala Leu Val Leu Ala Asp Gln Gly Val Cys Cys Ile Asp Glu Phe Asp
            260                 265                 270

Lys Met Ala Glu Ala Asp Arg Thr Ala Ile His Glu Val Met Glu Gln
        275                 280                 285

Gln Thr Ile Ser Ile Ala Lys Ala Gly Ile Leu Thr Thr Leu Asn Ala
    290                 295                 300

Arg Cys Ser Ile Leu Ala Ala Ala Asn Pro Ala Tyr Gly Arg Tyr Asn
305                 310                 315                 320

Pro Arg Arg Ser Leu Glu Gln Asn Ile Gln Leu Pro Ala Ala Leu Leu
                325                 330                 335

Ser Arg Phe Asp Leu Leu Trp Leu Ile Gln Asp Arg Pro Asp Arg Asp
```

```
                340             345             350
Asn Asp Leu Arg Leu Ala Gln His Ile Thr Tyr Val His Gln His Ser
            355                 360                 365
Arg Gln Pro Pro Ser Gln Phe Glu Pro Leu Asp Met Lys Leu Met Arg
        370                 375                 380
Arg Tyr Ile Ala Met Cys Arg Glu Lys Gln Pro Met Val Pro Glu Ser
385                 390                 395                 400
Leu Ala Asp Tyr Ile Thr Ala Ala Tyr Val Glu Met Arg Arg Glu Ala
                405                 410                 415
Trp Ala Ser Lys Asp Ala Thr Tyr Thr Ser Ala Arg Thr Leu Leu Ala
            420                 425                 430
Ile Leu Arg Leu Ser Thr Ala Leu Ala Arg Leu Arg Met Val Asp Val
            435                 440                 445
Val Glu Lys Glu Asp Val Asn Glu Ala Ile Arg Leu Met Glu Met Ser
        450                 455                 460
Lys Asp Ser Leu Leu Gly Asp Lys Gly Gln Thr Ala Arg Thr Gln Arg
465                 470                 475                 480
Pro Ala Asp Val Ile Phe Ala Thr Val Arg Glu Leu Val Ser Gly Gly
                485                 490                 495
Arg Ser Val Arg Phe Ser Glu Ala Glu Gln Arg Cys Val Ser Arg Gly
            500                 505                 510
Phe Thr Pro Ala Gln Phe Gln Ala Ala Leu Asp Glu Tyr Glu Glu Leu
        515                 520                 525
Asn Val Trp Gln Val Asn Ala Ser Arg Thr Arg Ile Thr Phe Val
    530                 535                 540

<210> SEQ ID NO 17
<211> LENGTH: 2140
<212> TYPE: DNA
<213> ORGANISM: Homo sapiens

<400> SEQUENCE: 17
agctgaggtg tgagcagctg ccgaagtcag ttccttgtgg agccggagct gggcgcggat      60
tcgccgaggc accgaggcac tcagaggagg cgccatgtca gaaccggctg gggatgtccg     120
tcagaaccca tgcggcagca aggcctgccg ccgcctcttc ggcccagtgg acagcgagca     180
gctgagccgc gactgtgatg cgctaatggc gggctgcatc caggaggccc gtgagcgatg     240
gaacttcgac tttgtcaccg agacaccact ggagggtgac ttcgcctggg agcgtgtgcg     300
gggccttggc ctgcccaagc tctaccttcc cacggggccc cggcgaggcc gggatgagtt     360
gggaggaggc aggcggcctg gcacctcacc tgctctgctg caggggacag cagaggaaga     420
ccatgtggac ctgtcactgt cttgtaccct tgtgcctcgc tcaggggagc aggctgaagg     480
gtccccaggt ggacctggag actctcaggg tcgaaaacgg cggcagacca gcatgacaga     540
tttctaccac tccaaacgcc ggctgatctt ctccaagagg aagccctaat ccgcccacag     600
gaagcctgca gtcctggaag cgcgagggcc tcaaggcccc gctctacatc ttctgcctta     660
gtctcagttt gtgtgtctta attattattt gtgttttaat ttaaacacct cctcatgtac     720
atacccctggc cgcccccctgc ccccagcct ctggcattag aattatttaa acaaaaacta     780
ggcggttgaa tgagaggttc ctaagagtgc tgggcatttt tatttttatga aatactattt     840
aaagcctcct catcccgtgt tctccttttc ctctctcccg gaggttgggt gggccggctt     900
catgccagct acttcctcct ccccacttgt ccgctgggtg gtaccctctg gaggggtgtg     960
gctccttccc atcgctgtca caggcggtta tgaaattcac cccctttcct ggacactcag    1020
```

-continued

```
acctgaattc ttttcattt gagaagtaaa cagatggcac tttgaagggg cctcaccgag    1080
tgggggcatc atcaaaaact ttggagtccc ctcacctcct ctaaggttgg gcagggtgac    1140
cctgaagtga gcacagccta gggctgagct ggggacctgg taccctcctg gctcttgata    1200
cccccctctg tcttgtgaag gcagggggaa ggtggggtac tggagcagac caccccgcct    1260
gccctcatgg cccctctgac ctgcactggg gagcccgtct cagtgttgag ccttttccct    1320
ctttggctcc cctgtacctt tgaggagcc ccagcttacc cttcttctcc agctgggctc     1380
tgcaattccc ctctgctgct gtccctcccc cttgtctttc ccttcagtac cctctcatgc    1440
tccaggtggc tctgaggtgc ctgtcccacc cccaccccca gctcaatgga ctggaagggg    1500
aagggacaca caagaagaag ggcaccctag ttctacctca ggcagctcaa gcagcgaccg    1560 cccccctcctc tagctgtggg ggtgagggtc ccatgtggtg gcacaggccc ccttgagtgg   1620
ggttatctct gtgttagggg tatatgatgg gggagtagat cttctagga gggagacact    1680 ggcccctcaa atcgtccagc gaccttcctc atccacccca tccctcccca gttcattgca   1740
ctttgattag cagcggaaca aggagtcaga cattttaaga tggtggcagt agaggctatg    1800
gacagggcat gccacgtggg ctcatatggg gctgggagta gttgtctttc ctggcactaa    1860
cgttgagccc ctggaggcac tgaagtgctt agtgtacttg gagtattggg gtctgacccc    1920
aaacaccttc cagctcctgt aacatactgg cctggactgt tttctctcgg ctccccatgt    1980
gtcctggttc ccgtttctcc acctagactg taaacctctc gagggcaggg accacaccct    2040
gtactgttct gtgtctttca cagctcctcc cacaatgctg aatatacagc aggtgctcaa    2100
taaatgattc ttagtgactt taaaaaaaaa aaaaaaaaa                           2140
```

<210> SEQ ID NO 18
<211> LENGTH: 164
<212> TYPE: PRT
<213> ORGANISM: Homo sapiens

<400> SEQUENCE: 18

```
Met Ser Glu Pro Ala Gly Asp Val Arg Gln Asn Pro Cys Gly Ser Lys
 1               5                  10                  15

Ala Cys Arg Arg Leu Phe Gly Pro Val Asp Ser Glu Gln Leu Ser Arg
                20                  25                  30

Asp Cys Asp Ala Leu Met Ala Gly Cys Ile Gln Glu Ala Arg Glu Arg
            35                  40                  45

Trp Asn Phe Asp Phe Val Thr Glu Thr Pro Leu Glu Gly Asp Phe Ala
        50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Arg Arg Pro Gly
                85                  90                  95

Thr Ser Pro Ala Leu Leu Gln Gly Thr Ala Glu Glu Asp His Val Asp
               100                 105                 110

Leu Ser Leu Ser Cys Thr Leu Val Pro Arg Ser Gly Glu Gln Ala Glu
           115                 120                 125

Gly Ser Pro Gly Gly Pro Gly Asp Ser Gln Gly Arg Lys Arg Arg Gln
       130                 135                 140

Thr Ser Met Thr Asp Phe Tyr His Ser Lys Arg Arg Leu Ile Phe Ser
145                 150                 155                 160

Lys Arg Lys Pro
```

<210> SEQ ID NO 19
<211> LENGTH: 2281
<212> TYPE: DNA
<213> ORGANISM: Homo sapiens

<400> SEQUENCE: 19

```
agctgaggtg tgagcagctg ccgaagtcag ttccttgtgg agccggagct gggcgcggat      60
tcgccgaggc accgaggcac tcagaggagg tgagagagcg gcggcagaca acaggggacc     120
ccgggccggc ggcccagagc cgagccaagc gtgcccgcgt gtgtccctgc gtgtccgcga     180
ggatgcgtgt tcgcgggtgt gtgctgcgtt cacaggtgtt tctgcggcag gcgccatgtc     240
agaaccggct ggggatgtcc gtcagaaccc atgcggcagc aaggcctgcc gccgcctctt     300
cggcccagtg gacagcgagc agctgagccg cgactgtgat gcgctaatgg cgggctgcat     360
ccaggaggcc cgtgagcgat ggaacttcga ctttgtcacc gagacaccac tggagggtga     420
cttcgcctgg gagcgtgtgc ggggccttgg cctgcccaag ctctaccttc ccacggggcc     480
ccggcgaggc cgggatgagt tgggaggagg caggcggcct ggcacctcac ctgctctgct     540
gcaggggaca gcagaggaag accatgtgga cctgtcactg tcttgtaccc ttgtgcctcg     600
ctcaggggag caggctgaag gtccccagg tggacctgga gactctcagg gtcgaaaacg     660
gcggcagacc agcatgacag atttctacca ctccaaacgc cggctgatct tctccaagag     720
gaagccctaa tccgcccaca ggaagcctgc agtcctggaa gcgcgagggc ctcaaaggcc     780
cgctctacat cttctgcctt agtctcagtt tgtgtgtctt aattattatt tgtgttttaa     840
tttaaacacc tcctcatgta catacccctgg ccgcccctg cccccagcc tctggcatta     900
gaattattta acaaaaaact aggcggttga atgagaggtt cctaagagtg ctgggcattt     960
ttattttatg aaatactatt taaagcctcc tcatcccgtg ttctccttt cctctctccc    1020
ggaggttggg tgggccggct tcatgccagc tacttcctcc tccccacttg tccgctgggt    1080
ggtaccctct ggagggtgt ggctccttcc catcgctgtc acaggcggtt atgaaattca    1140
ccccctttcc tggacactca gacctgaatt cttttcatt tgagaagtaa acagatggca    1200
ctttgaaggg gcctcaccga gtgggggcat catcaaaaac tttggagtcc cctcacctcc    1260
tctaaggttg gcagggtga ccctgaagtg agcacagcct agggctgagc tggggacctg    1320
gtaccctcct ggctcttgat ccccctctct gtcttgtgaa ggcagggga aggtggggtc    1380
ctggagcaga ccaccccgcc tgccctcatg gcccctctga cctgcactgg ggagcccgtc    1440
tcagtgttga gccttttccc tctttggctc ccctgtacct tttgaggagc cccagctacc    1500
cttcttctcc agctgggctc tgcaattccc ctctgctgct gtccctcccc cttgtccttt    1560
cccttcagta ccctctcagc tccaggtggc tctgaggtgc ctgtcccacc cccaccccca    1620
gctcaatgga ctggaagggg aagggacaca caagaagaag ggcaccctag ttctacctca    1680
ggcagctcaa gcgcgaccg ccccctcctc tagctgtggg ggtgagggtc ccatgtggtg    1740
gcacaggccc ccttgagtgg ggttatctct gtgttagggg tatatgatgg gggagtagat    1800
cttttctagga gggagacact ggcccctcaa atcgtccagc gaccttcctc atccacccca    1860
tccctcccca gttcattgca ctttgattag cagcggaaca aggagtcaga cattttaaga    1920
tggtggcagt agaggctatg gacagggcat gccacgtggg ctcatatggg gctgggagta    1980
gttgtctttc ctggcactaa cgttgagccc ctggaggcac tgaagtgctt agtgtacttg    2040
gagtattggg gtctgacccc aaacaccttc cagctcctgt aacatactgg cctgactgt    2100
tttctctcgg ctccccatgt gtcctggttc ccgtttctcc acctagactg taaacctctc    2160
```

```
gagggcaggg accacaccct gtactgttct gtgtctttca cagctcctcc cacaatgctg    2220
aatatacagc aggtgctcaa taaatgattc ttagtgactt taaaaaaaaa aaaaaaaaa     2280 a                                                                   2281
```

<210> SEQ ID NO 20
<211> LENGTH: 164
<212> TYPE: PRT
<213> ORGANISM: Homo sapiens

<400> SEQUENCE: 20

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```

<210> SEQ ID NO 21
<211> LENGTH: 1275
<212> TYPE: DNA
<213> ORGANISM: Homo sapiens

<400> SEQUENCE: 21

```
cctccctacg ggcgcctccg gcagcccttc ccgcgtgcgc agggctcaga gccgttccga    60
gatcttggag gtccgggtgg gagtgggggt ggggtgggggg tggggggtgaa ggtgggggggc  120 gggcgcgctc agggaaggcg ggtgcgcgcc tgcggggcgg agatgggcag ggggcggtgc   180
gtgggtccca gtctgcagtt aaggggggcag gagtggcgct gctcacctct ggtgccaaag   240
ggcggcgcag cggctgccga gctcggccct ggaggcggcg agaacatggt gcgcaggttc   300
ttggtgaccc tccggattcg gcgcgcgtgc ggcccgccgc gagtgagggt tttcgtggtt   360
cacatcccgc ggctcacggg ggagtgggca gcgccagggg cgcccgccgc tgtggccctc   420
gtgctgatgc tactgaggag ccagcgtcta gggcagcagc cgcttcctag aagaccaggt   480
catgatgatg ggcagcgccc gagtggcgga gctgctgctg ctccacggcg cggagcccaa   540
ctgcgccgac cccgccactc tcacccgacc cgtgcacgac gctgcccggg agggcttcct   600
ggacacgctg gtggtgctgc accgggccgg ggcgcggctg gacgtgcgcg atgcctgggg   660
ccgtctgccc gtggacctgg ctgaggagct gggccatcgc gatgtcgcac ggtacctgcg   720
```

| | |
|---|---|
| cgcggctgcg gggggcacca gaggcagtaa ccatgcccgc atagatgccg cggaaggtcc | 780 |
| ctcagacatc cccgattgaa agaaccagag aggctctgag aaacctcggg aaacttagat | 840 |
| catcagtcac cgaaggtcct acagggccac aactgccccc gccacaaccc accccgcttt | 900 |
| cgtagttttc atttagaaaa tagagctttt aaaaatgtcc tgcctttta acgtagatata | 960 |
| tgccttcccc cactaccgta aatgtccatt tatatcattt tttatatatt cttataaaaa | 1020 |
| tgtaaaaaag aaaaacaccg cttctgcctt ttcactgtgt tggagttttc tggagtgagc | 1080 |
| actcacgccc taagcgcaca ttcatgtggg catttcttgc gagcctcgca gcctccggaa | 1140 |
| gctgtcgact tcatgacaag catttttgtga actaggaag ctcaggggg ttactggctt | 1200 |
| ctcttgagtc acactgctag caaatggcag aaccaaagct caaataaaaa taaataatt | 1260 |
| ttcattcatt cactc | 1275 |

<210> SEQ ID NO 22
<211> LENGTH: 173
<212> TYPE: PRT
<213> ORGANISM: Homo sapiens

<400> SEQUENCE: 22

```
Met Gly Arg Gly Arg Cys Val Gly Pro Ser Leu Gln Leu Arg Gly Gln
 1               5                  10                  15
Glu Trp Arg Cys Ser Pro Leu Val Pro Lys Gly Ala Ala Ala Ala
            20                  25                  30
Glu Leu Gly Pro Gly Gly Gly Glu Asn Met Val Arg Arg Phe Leu Val
        35                  40                  45
Thr Leu Arg Ile Arg Arg Ala Cys Gly Pro Pro Arg Val Arg Val Phe
    50                  55                  60
Val Val His Ile Pro Arg Leu Thr Gly Glu Trp Ala Ala Pro Gly Ala
65                  70                  75                  80
Pro Ala Ala Val Ala Leu Val Leu Met Leu Leu Arg Ser Gln Arg Leu
                85                  90                  95
Gly Gln Gln Pro Leu Pro Arg Arg Pro Gly His Asp Asp Gly Gln Arg
            100                 105                 110
Pro Ser Gly Gly Ala Ala Ala Ala Pro Arg Arg Gly Ala Gln Leu Arg
        115                 120                 125
Arg Pro Arg His Ser His Pro Thr Arg Ala Arg Cys Pro Gly Gly
    130                 135                 140
Leu Pro Gly His Ala Gly Gly Ala Ala Pro Gly Arg Gly Ala Ala Gly
145                 150                 155                 160
Arg Ala Arg Cys Leu Gly Pro Ser Ala Arg Gly Pro Gly
                165                 170
```

<210> SEQ ID NO 23
<211> LENGTH: 5698
<212> TYPE: DNA
<213> ORGANISM: Homo sapiens

<400> SEQUENCE: 23

| | |
|---|---|
| aggttcaagt ggagctctcc taaccgacgc gcgtctgtgg agaagcggct tggtcggggg | 60 |
| tggtctcgtg gggtcctgcc tgtttagtcg ctttcagggt tcttgagccc cttcacgacc | 120 |
| gtcaccatgg aagtgtcacc attgcagcct gtaaatgaaa atatgcaagt caacaaaata | 180 |
| aagaaaaatg aagatgctaa gaaaagactg tctgttgaaa gaatctatca aagaaaaca | 240 |
| caattggaac atattttgct ccgcccagac acctacattg ttctgtgga attagtgacc | 300 |

```
cagcaaatgt gggtttacga tgaagatgtt ggcattaact ataggqaaqt cactttgtt      360 cctggtttgt acaaaatctt tgatgagatt ctagttaatg ctgcggacaa caaacaaagg    420
gacccaaaaa tgtcttgtat tagagtcaca attgatccgg aaaacaattt aattagtata    480
tggaataatg gaaaaggtat tcctgttgtt gaacacaaag ttgaaaagat gtatgtccca    540
gctctcatat ttggacagct cctaacttct agtaactatg atgatgatga aaagaaagtg    600
acaggtggtc gaaatggcta tggagccaaa ttgtgtaaca tattcagtac caaatttact    660
gtggaaacag ccagtagaga atacaagaaa atgttcaaac agacatggat ggataatatg    720
ggaagagctg tgagatgga actcaagccc ttcaatggag aagattatac atgtatcacc     780
tttcagcctg atttgtctaa gtttaaaatg caaagcctgg acaaagatat tgttgcacta    840
atggtcagaa gagcatatga tattgctgga tccaccaaag atgtcaaagt ctttcttaat    900
ggaaataaac tgccagtaaa aggatttcgt agttatgtgg acatgtattt gaaggacaag    960
ttggatgaaa ctggtaactc cttgaaagta atacatgaac aagtaaacca caggtgggaa   1020
gtgtgtttaa ctatgagtga aaaaggcttt cagcaaatta gctttgtcaa cagcattgct   1080
acatccaagg gtggcagaca tgttgattat gtagctgatc agattgtgac taaacttgtt   1140
gatgttgtga agaagaagaa caagggtggt gttgcagtaa aagcacatca ggtgaaaaat   1200
cacatgtgga ttttgtaaa tgccttaatt gaaaacccaa cctttgactc tcagacaaaa    1260
gaaaacatga ctttacaacc caagagcttt ggatcaacat gccaattgag tgaaaaattt   1320
atcaaagctg ccattggctg tggtattgta gaaagcatac taaactgggt gaagtttaag   1380
gcccaagtcc agttaaacaa gaagtgttca gctgtaaaac ataatagaat caagggaatt   1440
cccaaactcg atgatgccaa tgatgcaggg ggccgaaact ccactgagtg tacgcttatc   1500
ctgactgagg gagattcagc caaaactttg gctgtttcag gccttggtgt ggttgggaga   1560
gacaaatatg gggttttccc tcttagagga aaaatactca atgttcgaga agcttctcat   1620
aagcagatca tggaaaatgc tgagattaac aatatcatca agattgtggg tcttcagtac   1680
aagaaaaact atgaagatga agattcattg aagacgcttc gttatgggaa gataatgatt   1740
atgacagatc aggaccaaga tggttcccac atcaaaggct tgctgattaa tttatccat    1800 cacaactggc cctctcttct gcgacatcgt tttctggagg aatttatcac tcccattgta   1860
aaggtatcta aaaacaagca agaaatggca ttttacagcc ttcctgaatt tgaagagtgg   1920
aagagttcta ctccaaatca taaaaaatgg aaagtcaaat attacaaagg tttgggcacc   1980
agcacatcaa aggaagctaa agaatacttt gcagatatga aaagacatcg tatccagttc   2040
aaatattctg gtcctgaaga tgatgctgct atcagcctgg cctttagcaa aaaacagata   2100
gatgatcgaa aggaatggtt aactaatttc atggaggata aagacaacg aaagttactt    2160 gggcttcctg aggattactt gtatggacaa actaccacat atctgacata taatgacttc   2220
atcaacaagg aacttatctt gttctcaaat tctgataacg agagatctat cccttctatg   2280
gtggatggtt tgaaaccagg tcagagaaag gttttgttta cttgcttcaa acggaatgac   2340
aagcgagaag taaaggttgc ccaattagct ggatcagtgg ctgaaatgtc ttcttatcat   2400
catggtgaga tgtcactaat gatgaccatt atcaatttgg ctcagaattt tgtgggtagc   2460
aataatctaa acctcttgca gcccattggt cagtttggta ccaggctaca tggtggcaag   2520
gattctgcta gtccacgata catctttaca atgctcagct ctttggctcg attgttattt   2580
ccaccaaaag atgatcacac gttgaagttt ttatatgatg acaaccagcg tgttgagcct   2640
gaatggtaca ttcctattat tcccatggtg ctgataaatg gtgctgaagg aatcggtact   2700
```

```
gggtggtcct gcaaaatccc caactttgat gtgcgtgaaa ttgtaaataa catcaggcgt    2760
ttgatggatg gagaagaacc tttgccaatg cttccaagtt acaagaactt caagggtact    2820
attgaagaac tggctccaaa tcaatatgtg attagtggtg aagtagctat tcttaattct    2880
acaaccattg aaatctcaga gcttcccgtc agaacatgga cccagacata caagaacaa     2940 gttctagaac ccatgttgaa tggcaccgag aagacacctc ctctcataac agactatagg    3000
gaataccata cagataccac tgtgaaattt gttgtgaaga tgactgaaga aaaactggca    3060
gaggcagaga gagttggact acacaaagtc ttcaaactcc aaactagtct cacatgcaac    3120
tctatggtgc tttttgacca cgtaggctgt ttaaagaaat atgacacggt gttggatatt    3180
ctaagagact ttttgaact cagacttaaa tattatggat taagaaaaga atggctccta    3240
ggaatgcttg gtgctgaatc tgctaaactg aataatcagg ctcgctttat cttagagaaa    3300
atagatggca aaataatcat tgaaaataag cctaagaaaa aattaattaa agttctgatt    3360
cagaggggat atgattcgga tcctgtgaag gcctggaaag aagcccagca aaaggttcca    3420
gatgaagaag aaaatgaaga gagtgacaac gaaaaggaaa ctgaaaagag tgactccgta    3480
acagattctg gaccaacctt caactatctt cttgatatgc ccctttggta tttaaccaag    3540
gaaaagaaag atgaactctg caggctaaga aatgaaaaag acaagagct ggacacatta     3600 aaagaaaga gtccatcaga tttgtggaaa gaagacttgg ctacatttat tgaagaattg     3660
gaggctgttg aagccaagga aaacaagat gaacaagtcg acttcctgg gaaaggggg      3720 aaggccaagg ggaaaaaaac acaaatggct gaagttttgc cttctccgcg tggtcaaaga    3780
gtcattccac gaataaccat agaaatgaaa gcagaggcag aaaagaaaaa taaaagaaa     3840 attaagaatg aaaatactga aggaagccct caagaagatg gtgtggaact agaaggccta    3900
aaacaaagat tagaaagaa acagaaaaga gaaccaggta caaagacaaa gaaacaaact     3960
acattggcat ttaagccaat caaaaaagga aagaagagaa atccctggtc tgattcagaa    4020
tcagatagga gcagtgacga aagtaatttt gatgtccctc cacgagaaac agagccacgg    4080
agagcagcaa caaaaacaaa attcacaatg gatttggatt cagatgaaga tttctcagat    4140
tttgatgaaa aaactgatga tgaagatttt gtcccatcag atgctagtcc acctaagacc    4200
aaaacttccc caaacttag taacaaagaa ctgaaaccac agaaaagtgt cgtgtcagac    4260
cttgaagctg atgatgttaa gggcagtgta ccactgtctt caagccctcc tgctacacat    4320
ttcccagatg aaactgaaat tacaaaccca gttcctaaaa agaatgtgac agtgaagaag    4380
acagcagcaa aaagtcagtc ttccacctcc actaccggtg ccaaaaaag ggctgcccca    4440 aaaggaacta aagggatcc agctttgaat tctggtgtct ctcaaaagcc tgatcctgcc     4500
aaaaccaaga atcgccgcaa aaggaagcca tccacttctg atgattctga ctctaatttt    4560
gagaaaattg tttcgaaagc agtcacaagc aagaaatcca aggggagag tgatgacttc    4620 catatggact ttgactcagc tgtggctcct cgggcaaaat ctgtacgggc aaagaaacct    4680
ataaagtacc tggaagagtc agatgaagat gatctgtttt aaaatgtgag gcgattattt    4740
taagtaatta tcttaccaag cccaagactg gttttaaagt tacctgaagc tcttaacttc    4800 ctccctctg aatttagttt ggggaaggtg tttttagtac aagacatcaa agtgaagtaa     4860
agcccaagtg ttctttagct ttttataata ctgtctaaat agtgaccatc tcatgggcat    4920
tgttttcttc tctgctttgt ctgtgtttg agtctgcttt cttttgtctt taaaacctga    4980 ttttaagtt cttctgaact gtagaaatag ctatctgatc acttcagcgt aaagcagtgt     5040
```

```
gtttattaac catccactaa gctaaaacta gagcagtttg atttaaaagt gtcactcttc    5100 ctcctttct actttcagta gatatgagat agagcataat tatctgtttt atcttagttt    5160
tatacataat ttaccatcag atagaacttt atggttctag tacagatact ctactacact    5220
cagcctctta tgtgccaagt ttttctttaa gcaatgagaa attgctcatg ttcttcatct    5280
tctcaaatca tcagaggcca aagaaaaaca ctttggctgt gtctataact tgacacagtc    5340
aatagaatga agaaaattag agtagttatg tgattatttc agctcttgac ctgtcccctc    5400
tggctgcctc tgagtctgaa tctcccaaag agagaaacca atttctaaga ggactggatt    5460
gcagaagact cggggacaac atttgatcca agatcttaaa tgttatattg ataaccatgc    5520
tcagcaatga gctattagat tcattttggg aaatctccat aatttcaatt tgtaaacttt    5580
gttaagacct gtctacattg ttatatgtgt gtgacttgag taatgttatc aacgttttg    5640 taaatattta ctatgttttt ctattagcta aattccaaca attttgtact ttaataaa    5698
```

<210> SEQ ID NO 24
<211> LENGTH: 1531
<212> TYPE: PRT
<213> ORGANISM: Homo sapiens

<400> SEQUENCE: 24

```
Met Glu Val Ser Pro Leu Gln Pro Val Asn Glu Asn Met Gln Val Asn
1               5                   10                  15

Lys Ile Lys Lys Asn Glu Asp Ala Lys Lys Arg Leu Ser Val Glu Arg
            20                  25                  30

Ile Tyr Gln Lys Lys Thr Gln Leu Glu His Ile Leu Leu Arg Pro Asp
        35                  40                  45

Thr Tyr Ile Gly Ser Val Glu Leu Val Thr Gln Gln Met Trp Val Tyr
    50                  55                  60

Asp Glu Asp Val Gly Ile Asn Tyr Arg Glu Val Thr Phe Val Pro Gly
65                  70                  75                  80

Leu Tyr Lys Ile Phe Asp Glu Ile Leu Val Asn Ala Ala Asp Asn Lys
                85                  90                  95

Gln Arg Asp Pro Lys Met Ser Cys Ile Arg Val Thr Ile Asp Pro Glu
            100                 105                 110

Asn Asn Leu Ile Ser Ile Trp Asn Asn Gly Lys Gly Ile Pro Val Val
        115                 120                 125

Glu His Lys Val Glu Lys Met Tyr Val Pro Ala Leu Ile Phe Gly Gln
    130                 135                 140

Leu Leu Thr Ser Ser Asn Tyr Asp Asp Asp Glu Lys Lys Val Thr Gly
145                 150                 155                 160

Gly Arg Asn Gly Tyr Gly Ala Lys Leu Cys Asn Ile Phe Ser Thr Lys
                165                 170                 175

Phe Thr Val Glu Thr Ala Ser Arg Glu Tyr Lys Lys Met Phe Lys Gln
            180                 185                 190

Thr Trp Met Asp Asn Met Gly Arg Ala Gly Glu Met Glu Leu Lys Pro
        195                 200                 205

Phe Asn Gly Glu Asp Tyr Thr Cys Ile Thr Phe Gln Pro Asp Leu Ser
    210                 215                 220

Lys Phe Lys Met Gln Ser Leu Asp Lys Asp Ile Val Ala Leu Met Val
225                 230                 235                 240

Arg Arg Ala Tyr Asp Ile Ala Gly Ser Thr Lys Asp Val Lys Val Phe
                245                 250                 255

Leu Asn Gly Asn Lys Leu Pro Val Lys Gly Phe Arg Ser Tyr Val Asp
```

-continued

```
                260                 265                 270
Met Tyr Leu Lys Asp Lys Leu Asp Glu Thr Gly Asn Ser Leu Lys Val
    275                 280                 285
Ile His Glu Gln Val Asn His Arg Trp Glu Val Cys Leu Thr Met Ser
    290                 295                 300
Glu Lys Gly Phe Gln Gln Ile Ser Phe Val Asn Ser Ile Ala Thr Ser
305                 310                 315                 320
Lys Gly Gly Arg His Val Asp Tyr Val Ala Asp Gln Ile Val Thr Lys
                325                 330                 335
Leu Val Asp Val Val Lys Lys Asn Lys Gly Gly Val Ala Val Lys
                340                 345                 350
Ala His Gln Val Lys Asn His Met Trp Ile Phe Val Asn Ala Leu Ile
    355                 360                 365
Glu Asn Pro Thr Phe Asp Ser Gln Thr Lys Glu Asn Met Thr Leu Gln
    370                 375                 380
Pro Lys Ser Phe Gly Ser Thr Cys Gln Leu Ser Glu Lys Phe Ile Lys
385                 390                 395                 400
Ala Ala Ile Gly Cys Gly Ile Val Glu Ser Ile Leu Asn Trp Val Lys
                405                 410                 415
Phe Lys Ala Gln Val Gln Leu Asn Lys Lys Cys Ser Ala Val Lys His
                420                 425                 430
Asn Arg Ile Lys Gly Ile Pro Lys Leu Asp Asp Ala Asn Asp Ala Gly
            435                 440                 445
Gly Arg Asn Ser Thr Glu Cys Thr Leu Ile Leu Thr Glu Gly Asp Ser
    450                 455                 460
Ala Lys Thr Leu Ala Val Ser Gly Leu Gly Val Val Gly Arg Asp Lys
465                 470                 475                 480
Tyr Gly Val Phe Pro Leu Arg Gly Lys Ile Leu Asn Val Arg Glu Ala
                485                 490                 495
Ser His Lys Gln Ile Met Glu Asn Ala Glu Ile Asn Asn Ile Ile Lys
            500                 505                 510
Ile Val Gly Leu Gln Tyr Lys Lys Asn Tyr Glu Asp Glu Asp Ser Leu
    515                 520                 525
Lys Thr Leu Arg Tyr Gly Lys Ile Met Ile Met Thr Asp Gln Asp Gln
    530                 535                 540
Asp Gly Ser His Ile Lys Gly Leu Leu Ile Asn Phe Ile His His Asn
545                 550                 555                 560
Trp Pro Ser Leu Leu Arg His Arg Phe Leu Glu Glu Phe Ile Thr Pro
                565                 570                 575
Ile Val Lys Val Ser Lys Asn Lys Gln Glu Met Ala Phe Tyr Ser Leu
                580                 585                 590
Pro Glu Phe Glu Glu Trp Lys Ser Ser Thr Pro Asn His Lys Lys Trp
            595                 600                 605
Lys Val Lys Tyr Tyr Lys Gly Leu Gly Thr Ser Thr Ser Lys Glu Ala
    610                 615                 620
Lys Glu Tyr Phe Ala Asp Met Lys Arg His Arg Ile Gln Phe Lys Tyr
625                 630                 635                 640
Ser Gly Pro Glu Asp Asp Ala Ala Ile Ser Leu Ala Phe Ser Lys Lys
                645                 650                 655
Gln Ile Asp Asp Arg Lys Glu Trp Leu Thr Asn Phe Met Glu Asp Arg
            660                 665                 670
Arg Gln Arg Lys Leu Leu Gly Leu Pro Glu Asp Tyr Leu Tyr Gly Gln
    675                 680                 685
```

```
Thr Thr Thr Tyr Leu Thr Tyr Asn Asp Phe Ile Asn Lys Glu Leu Ile
    690             695                 700

Leu Phe Ser Asn Ser Asp Asn Glu Arg Ser Ile Pro Ser Met Val Asp
705             710                 715                 720

Gly Leu Lys Pro Gly Gln Arg Lys Val Leu Phe Thr Cys Phe Lys Arg
                725                 730                 735

Asn Asp Lys Arg Glu Val Lys Val Ala Gln Leu Ala Gly Ser Val Ala
            740                 745                 750

Glu Met Ser Ser Tyr His His Gly Glu Met Ser Leu Met Met Thr Ile
        755                 760                 765

Ile Asn Leu Ala Gln Asn Phe Val Gly Ser Asn Asn Leu Asn Leu Leu
    770                 775                 780

Gln Pro Ile Gly Gln Phe Gly Thr Arg Leu His Gly Gly Lys Asp Ser
785                 790                 795                 800

Ala Ser Pro Arg Tyr Ile Phe Thr Met Leu Ser Ser Leu Ala Arg Leu
                805                 810                 815

Leu Phe Pro Pro Lys Asp Asp His Thr Leu Lys Phe Leu Tyr Asp Asp
            820                 825                 830

Asn Gln Arg Val Glu Pro Glu Trp Tyr Ile Pro Ile Pro Met Val
        835                 840                 845

Leu Ile Asn Gly Ala Glu Gly Ile Gly Thr Gly Trp Ser Cys Lys Ile
    850                 855                 860

Pro Asn Phe Asp Val Arg Glu Ile Val Asn Asn Ile Arg Arg Leu Met
865                 870                 875                 880

Asp Gly Glu Glu Pro Leu Pro Met Leu Pro Ser Tyr Lys Asn Phe Lys
                885                 890                 895

Gly Thr Ile Glu Glu Leu Ala Pro Asn Gln Tyr Val Ile Ser Gly Glu
            900                 905                 910

Val Ala Ile Leu Asn Ser Thr Thr Ile Glu Ile Ser Glu Leu Pro Val
        915                 920                 925

Arg Thr Trp Thr Gln Thr Tyr Lys Glu Gln Val Leu Glu Pro Met Leu
    930                 935                 940

Asn Gly Thr Glu Lys Thr Pro Pro Leu Ile Thr Asp Tyr Arg Glu Tyr
945                 950                 955                 960

His Thr Asp Thr Thr Val Lys Phe Val Val Lys Met Thr Glu Glu Lys
                965                 970                 975

Leu Ala Glu Ala Glu Arg Val Gly Leu His Lys Val Phe Lys Leu Gln
            980                 985                 990

Thr Ser Leu Thr Cys Asn Ser Met Val Leu Phe Asp His Val Gly Cys
        995                 1000                1005

Leu Lys Lys Tyr Asp Thr Val Leu Asp Ile Leu Arg Asp Phe Phe Glu
    1010                1015                1020

Leu Arg Leu Lys Tyr Tyr Gly Leu Arg Lys Glu Trp Leu Leu Gly Met
1025                1030                1035                1040

Leu Gly Ala Glu Ser Ala Lys Leu Asn Asn Gln Ala Arg Phe Ile Leu
                1045                1050                1055

Glu Lys Ile Asp Gly Lys Ile Ile Glu Asn Lys Pro Lys Lys Glu
            1060                1065                1070

Leu Ile Lys Val Leu Ile Gln Arg Gly Tyr Asp Ser Asp Pro Val Lys
        1075                1080                1085

Ala Trp Lys Glu Ala Gln Gln Lys Val Pro Asp Glu Glu Asn Glu
    1090                1095                1100
```

-continued

```
Glu Ser Asp Asn Glu Lys Glu Thr Glu Lys Ser Asp Ser Val Thr Asp
1105                1110                1115                1120

Ser Gly Pro Thr Phe Asn Tyr Leu Leu Asp Met Pro Leu Trp Tyr Leu
                1125                1130                1135

Thr Lys Glu Lys Lys Asp Glu Leu Cys Arg Leu Arg Asn Glu Lys Glu
            1140                1145                1150

Gln Glu Leu Asp Thr Leu Lys Arg Lys Ser Pro Ser Asp Leu Trp Lys
        1155                1160                1165

Glu Asp Leu Ala Thr Phe Ile Glu Glu Leu Glu Ala Val Glu Ala Lys
    1170                1175                1180

Glu Lys Gln Asp Glu Gln Val Gly Leu Pro Gly Lys Gly Gly Lys Ala
1185                1190                1195                1200

Lys Gly Lys Lys Thr Gln Met Ala Glu Val Leu Pro Ser Pro Arg Gly
                1205                1210                1215

Gln Arg Val Ile Pro Arg Ile Thr Ile Glu Met Lys Ala Glu Ala Glu
            1220                1225                1230

Lys Lys Asn Lys Lys Lys Ile Lys Asn Glu Asn Thr Glu Gly Ser Pro
        1235                1240                1245

Gln Glu Asp Gly Val Glu Leu Glu Gly Leu Lys Gln Arg Leu Glu Lys
    1250                1255                1260

Lys Gln Lys Arg Glu Pro Gly Thr Lys Thr Lys Lys Gln Thr Thr Leu
1265                1270                1275                1280

Ala Phe Lys Pro Ile Lys Lys Gly Lys Lys Arg Asn Pro Trp Ser Asp
                1285                1290                1295

Ser Glu Ser Asp Arg Ser Ser Asp Glu Ser Asn Phe Asp Val Pro Pro
            1300                1305                1310

Arg Glu Thr Glu Pro Arg Arg Ala Ala Thr Lys Thr Lys Phe Thr Met
        1315                1320                1325

Asp Leu Asp Ser Asp Glu Asp Phe Ser Asp Phe Asp Glu Lys Thr Asp
    1330                1335                1340

Asp Glu Asp Phe Val Pro Ser Asp Ala Ser Pro Pro Lys Thr Lys Thr
1345                1350                1355                1360

Ser Pro Lys Leu Ser Asn Lys Glu Leu Lys Pro Gln Lys Ser Val Val
                1365                1370                1375

Ser Asp Leu Glu Ala Asp Asp Val Lys Gly Ser Val Pro Leu Ser Ser
            1380                1385                1390

Ser Pro Pro Ala Thr His Phe Pro Asp Glu Thr Glu Ile Thr Asn Pro
        1395                1400                1405

Val Pro Lys Lys Asn Val Thr Val Lys Lys Thr Ala Ala Lys Ser Gln
    1410                1415                1420

Ser Ser Thr Ser Thr Thr Gly Ala Lys Lys Arg Ala Ala Pro Lys Gly
1425                1430                1435                1440

Thr Lys Arg Asp Pro Ala Leu Asn Ser Gly Val Ser Gln Lys Pro Asp
                1445                1450                1455

Pro Ala Lys Thr Lys Asn Arg Arg Lys Arg Lys Pro Ser Thr Ser Asp
            1460                1465                1470

Asp Ser Asp Ser Asn Phe Glu Lys Ile Val Ser Lys Ala Val Thr Ser
        1475                1480                1485

Lys Lys Ser Lys Gly Glu Ser Asp Asp Phe His Met Asp Phe Asp Ser
    1490                1495                1500

Ala Val Ala Pro Arg Ala Lys Ser Val Arg Ala Lys Lys Pro Ile Lys
1505                1510                1515                1520

Tyr Leu Glu Glu Ser Asp Glu Asp Asp Leu Phe
```

<210> SEQ ID NO 25
<211> LENGTH: 17
<212> TYPE: DNA
<213> ORGANISM: Artificial Sequence
<220> FEATURE:
<223> OTHER INFORMATION: Primer

<400> SEQUENCE: 25
ctctgagccc gccaagc                                                        17

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
tgtaagaact tcttaacctt ttccttctct a                                        31

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ccctcggcag cgatggcact                                                     20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gaggaatccc gagctgtgaa                                                     20

<210> SEQ ID NO 29
<211> LENGTH: 14
<212> TYPE: DNA
<213> ORGANISM: Artificial Sequence
<220> FEATURE:
<223> OTHER INFORMATION: Primer

<400> SEQUENCE: 29
cccgctcccg ccat                                                           14

<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30
cccatgtgct tctttgttta ctaagagcgg aa                                       32

<210> SEQ ID NO 31
<211> LENGTH: 17
<212> TYPE: DNA
<213> ORGANISM: Artificial Sequence

```
<220> FEATURE:
<223> OTHER INFORMATION: Primer

<400> SEQUENCE: 31
gtccgaagcc cccagaa                                                    17

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
cccgacagag accactcaca                                                 20

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
cagtaccctg ctgaactcat gcgca                                           25

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
cgctacgcga agctctttg                                                  19

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
cctttgtttg ccattgttct ctaa                                            24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tgccgtacaa gagctgctgc ctca                                            24

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
caaacgccgg ctgatctt                                                   18
```

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
ccaggactgc aggcttcct                                            19

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
caagaggaag ccctaatccg ccca                                      24

<210> SEQ ID NO 40
<211> LENGTH: 16
<212> TYPE: DNA
<213> ORGANISM: Artificial Sequence
<220> FEATURE:
<223> OTHER INFORMATION: Primer

<400> SEQUENCE: 40
gagcggcggc agacaa                                               16

<210> SEQ ID NO 41
<211> LENGTH: 17
<212> TYPE: DNA
<213> ORGANISM: Artificial Sequence
<220> FEATURE:
<223> OTHER INFORMATION: Primer

<400> SEQUENCE: 41
ccgcgaacac gcatcct                                              17

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
cccagagccg agccaagcgt g                                         21

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
tggagactct cagggtcgaa a                                         21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
tccagtctgg ccaacagagt t                                    21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cggcggcaga ccagcatgac                                      20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gccctcgtgc tgatgctact                                      20

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
tcatcatgac ctggtcttct agga                                 24

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
agcgtctagg gcagcagccg c                                    21

<210> SEQ ID NO 49
<211> LENGTH: 15
<212> TYPE: DNA
<213> ORGANISM: Artificial Sequence
<220> FEATURE:
<223> OTHER INFORMATION: Primer

<400> SEQUENCE: 49
tgcccaacgc accga                                           15

<210> SEQ ID NO 50
<211> LENGTH: 15
<212> TYPE: DNA
<213> ORGANISM: Artificial Sequence
<220> FEATURE:
<223> OTHER INFORMATION: Primer

<400> SEQUENCE: 50
gggcgctgcc catca                                           15

<210> SEQ ID NO 51

```
<211> LENGTH: 22
<212> TYPE: DNA
<213> ORGANISM: Artificial Sequence
<220> FEATURE:
<223> OTHER INFORMATION: Primer

<400> SEQUENCE: 51
tcggaggccg atccaggtca tg                                              22

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
aagcttcctt tccgtcatgc                                                 20

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
catgacctgc cagagagaac ag                                              22

<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54
cccccaccct ggctctgacc a                                               21

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
ggaaaccaag gaagaggaat gag                                             23

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
tgttcccccc ttcagatctt ct                                              22

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
```

```
acgcgcgtac agatctctcg aatgct                                          26

<210> SEQ ID NO 58
<211> LENGTH: 18
<212> TYPE: DNA
<213> ORGANISM: Artificial Sequence
<220> FEATURE:
<223> OTHER INFORMATION: Primer

<400> SEQUENCE: 58
cacgccctaa gcgcacat                                                   18

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
cctagttcac aaaatgcttg tcatg                                           25

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
tttcttgcga gcctcgcagc ctc                                             23

<210> SEQ ID NO 61
<211> LENGTH: 24
<212> TYPE: DNA
<213> ORGANISM: Artificial Sequence
<220> FEATURE:
<223> OTHER INFORMATION: Primer

<400> SEQUENCE: 61
aaagaagatg atgaccgggt ttac                                            24

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
gagcctctgg atggtgcaa                                                  19

<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63
caaactcaac gtgcaagcct cgga                                            24

<210> SEQ ID NO 64
<211> LENGTH: 14
<212> TYPE: DNA
```

```
<213> ORGANISM: Artificial Sequence
<220> FEATURE:
<223> OTHER INFORMATION: Primer

<400> SEQUENCE: 64
tccgccgcgg acaa                                                      14

<210> SEQ ID NO 65
<211> LENGTH: 18
<212> TYPE: DNA
<213> ORGANISM: Artificial Sequence
<220> FEATURE:
<223> OTHER INFORMATION: Primer

<400> SEQUENCE: 65
catggtgtcc cgctcctt                                                  18

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
accctggcct caggccggag                                                20

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
ggaattgttg gccacctgta tt                                             22

<210> SEQ ID NO 68
<211> LENGTH: 27
<212> TYPE: DNA
<213> ORGANISM: Artificial Sequence
<220> FEATURE:
<223> OTHER INFORMATION: Primer

<400> SEQUENCE: 68
ctggagaaat cacttgttcc tatttct                                        27

<210> SEQ ID NO 69
<211> LENGTH: 32
<212> TYPE: DNA
<213> ORGANISM: Artificial Sequence
<220> FEATURE:
<223> OTHER INFORMATION: Primer

<400> SEQUENCE: 69
cagtccttgc attatcattg aaacacctca ca                                  32

<210> SEQ ID NO 70
<211> LENGTH: 28
<212> TYPE: DNA
<213> ORGANISM: Artificial Sequence
<220> FEATURE:
<223> OTHER INFORMATION: Primer

<400> SEQUENCE: 70
tcaactcatt ggaattacct cattattc                                       28
```

<210> SEQ ID NO 71
<211> LENGTH: 24
<212> TYPE: DNA
<213> ORGANISM: Artificial Sequence
<220> FEATURE:
<223> OTHER INFORMATION: Primer

<400> SEQUENCE: 71
accatcagtg acgtaagcaa actc                                          24

<210> SEQ ID NO 72
<211> LENGTH: 34
<212> TYPE: DNA
<213> ORGANISM: Artificial Sequence
<220> FEATURE:
<223> OTHER INFORMATION: Primer

<400> SEQUENCE: 72
ccaaacttga ggaaatctat gctcctaaac tcca                               34

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
ttttgaagtt ctgcattctg acttg                                         25

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74
accatcagtg acgtaagcaa gataa                                         25

<210> SEQ ID NO 75
<211> LENGTH: 34
<212> TYPE: DNA
<213> ORGANISM: Artificial Sequence
<220> FEATURE:
<223> OTHER INFORMATION: Primer

<400> SEQUENCE: 75
aaccacagat gaggtccata cttctagact ggct                               34

<210> SEQ ID NO 76
<211> LENGTH: 156
<212> TYPE: PRT
<213> ORGANISM: Homo sapiens
<220> FEATURE:
<221> NAME/KEY: VARIANT
<222> LOCATION: (1)...(156)
<223> OTHER INFORMATION: Partial amino acid sequence for p16/p14ARF
      isoform 1

<400> SEQUENCE: 76

Met Glu Pro Ala Ala Gly Ser Ser Met Glu Pro Ser Ala Asp Trp Leu
 1               5                  10                  15

Ala Thr Ala Ala Ala Arg Gly Arg Val Glu Glu Val Arg Ala Leu Leu
             20                  25                  30

Glu Ala Gly Ala Leu Pro Asn Ala Pro Asn Ser Tyr Gly Arg Arg Pro
            35                  40                  45

Ile Gln Val Met Met Met Gly Ser Ala Arg Val Ala Glu Leu Leu Leu
 50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
            130                 135                 140

Ile Asp Ala Ala Glu Gly Pro Ser Asp Ile Pro Asp
145                 150                 155

<210> SEQ ID NO 77
<211> LENGTH: 105
<212> TYPE: PRT
<213> ORGANISM: Homo sapiens
<220> FEATURE:
<221> NAME/KEY: VARIANT
<222> LOCATION: (1)...(105)
<223> OTHER INFORMATION: Partial amino acid sequence for p16/p14ARF
      isoform 2

<400> SEQUENCE: 77

Met Met Met Gly Ser Ala Arg Val Ala Glu Leu Leu Leu Leu His Gly
 1               5                  10                  15

Ala Glu Pro Asn Cys Ala Asp Pro Ala Thr Leu Thr Arg Pro Val His
            20                  25                  30

Asp Ala Ala Arg Glu Gly Phe Leu Asp Thr Leu Val Val Leu His Arg
         35                  40                  45

Ala Gly Ala Arg Leu Asp Val Arg Asp Ala Trp Gly Arg Leu Pro Val
     50                  55                  60

Asp Leu Ala Glu Glu Leu Gly His Arg Asp Val Ala Arg Tyr Leu Arg
65                  70                  75                  80

Ala Ala Ala Gly Gly Thr Arg Gly Ser Asn His Ala Arg Ile Asp Ala
                85                  90                  95

Ala Glu Gly Pro Ser Asp Ile Pro Asp
            100                 105

<210> SEQ ID NO 78
<211> LENGTH: 116
<212> TYPE: PRT
<213> ORGANISM: Homo sapiens
<220> FEATURE:
<221> NAME/KEY: VARIANT
<222> LOCATION: (1)...(116)
<223> OTHER INFORMATION: Partial amino acid sequence for p16/p14ARF
      isoform 3

<400> SEQUENCE: 78

Met Glu Pro Ala Ala Gly Ser Ser Met Glu Pro Ser Ala Asp Trp Leu
 1               5                  10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro

```
                35                  40                  45
Ile Gln Val Gly Arg Arg Ser Ala Ala Gly Ala Gly Asp Gly Gly Arg
         50                  55                  60

Leu Trp Arg Thr Lys Phe Ala Gly Glu Leu Glu Ser Gly Ser Ala Ser
 65                  70                  75                  80

Ile Leu Arg Lys Lys Gly Arg Leu Pro Gly Glu Phe Ser Glu Gly Val
                 85                  90                  95

Cys Asn His Arg Pro Pro Pro Gly Asp Ala Leu Gly Ala Trp Glu Thr
            100                 105                 110

Lys Glu Glu Glu
        115

<210> SEQ ID NO 79
<211> LENGTH: 173
<212> TYPE: PRT
<213> ORGANISM: Homo sapiens

<400> SEQUENCE: 79

Met Gly Arg Gly Arg Cys Val Gly Pro Ser Leu Gln Leu Arg Gly Gln
  1               5                  10                  15

Glu Trp Arg Cys Ser Pro Leu Val Pro Lys Gly Gly Ala Ala Ala Ala
                 20                  25                  30

Glu Leu Gly Pro Gly Gly Gly Glu Asn Met Val Arg Arg Phe Leu Val
             35                  40                  45

Thr Leu Arg Ile Arg Arg Ala Cys Gly Pro Pro Arg Val Arg Val Phe
 50                  55                  60

Val Val His Ile Pro Arg Leu Thr Gly Glu Trp Ala Ala Pro Gly Ala
 65                  70                  75                  80

Pro Ala Ala Val Ala Leu Val Leu Met Leu Leu Arg Ser Gln Arg Leu
                 85                  90                  95

Gly Gln Gln Pro Leu Pro Arg Arg Pro Gly His Asp Asp Gly Gln Arg
            100                 105                 110

Pro Ser Gly Gly Ala Ala Ala Pro Arg Arg Gly Ala Gln Leu Arg
            115                 120                 125

Arg Pro Arg His Ser His Pro Thr Arg Ala Arg Cys Pro Gly Gly
            130                 135                 140

Leu Pro Gly His Ala Gly Gly Ala Ala Pro Gly Arg Gly Ala Ala Gly
145                 150                 155                 160

Arg Ala Arg Cys Leu Gly Pro Ser Ala Arg Gly Pro Gly
                165                 170

<210> SEQ ID NO 80
<211> LENGTH: 21
<212> TYPE: DNA
<213> ORGANISM: Artificial Sequence
<220> FEATURE:
<223> OTHER INFORMATION: PCR primer

<400> SEQUENCE: 80
ggaggtggta ctggccatgt a                                      21

<210> SEQ ID NO 81
<211> LENGTH: 19
<212> TYPE: DNA
<213> ORGANISM: Artificial Sequence
<220> FEATURE:
<223> OTHER INFORMATION: PCR primer

<400> SEQUENCE: 81
```

-continued gggagatgcg gacatggat                                               19

<210> SEQ ID NO 82
<211> LENGTH: 25
<212> TYPE: DNA
<213> ORGANISM: Artificial Sequence
<220> FEATURE:
<223> OTHER INFORMATION: PCR primer

<400> SEQUENCE: 82
ccaagtacga ccgcatcacc aacca                                        25

<210> SEQ ID NO 83
<211> LENGTH: 21
<212> TYPE: DNA
<213> ORGANISM: Artificial Sequence
<220> FEATURE:
<223> OTHER INFORMATION: PCR primer

<400> SEQUENCE: 83
cattccaaga cctgcctacc a                                            21

<210> SEQ ID NO 84
<211> LENGTH: 21
<212> TYPE: DNA
<213> ORGANISM: Artificial Sequence
<220> FEATURE:
<223> OTHER INFORMATION: PCR primer

<400> SEQUENCE: 84
atgcgagtga gcaaaccaat t                                            21

<210> SEQ ID NO 85
<211> LENGTH: 29
<212> TYPE: DNA
<213> ORGANISM: Artificial Sequence
<220> FEATURE:
<223> OTHER INFORMATION: PCR primer

<400> SEQUENCE: 85
acacaagatt cgagagctca cctcatcca                                    29

<210> SEQ ID NO 86
<211> LENGTH: 19
<212> TYPE: DNA
<213> ORGANISM: Artificial Sequence
<220> FEATURE:
<223> OTHER INFORMATION: PCR primer

<400> SEQUENCE: 86
ggctacatgg tggcaagga                                               19

<210> SEQ ID NO 87
<211> LENGTH: 23
<212> TYPE: DNA
<213> ORGANISM: Artificial Sequence
<220> FEATURE:
<223> OTHER INFORMATION: PCR primer

<400> SEQUENCE: 87
tggaaataac aatcgagcca aag                                          23

<210> SEQ ID NO 88
<211> LENGTH: 34
<212> TYPE: DNA

<213> ORGANISM: Artificial Sequence
<220> FEATURE:
<223> OTHER INFORMATION: PCR primer

<400> SEQUENCE: 88
tgctagtcca cgatacatct ttacaatgct cagc    34

<210> SEQ ID NO 89
<211> LENGTH: 3769
<212> TYPE: DNA
<213> ORGANISM: Homo sapiens

<400> SEQUENCE: 89

| | | | | | |
|---|---|---|---|---|---|
| aaagctgcag | cgtctggaaa | aaagcgactt | gtggcggtcg | agcgtggcgc | aggcgaatcc | 60 |
| tcggcactaa | gcaaatatgg | acctcgcggc | ggcagcggag | ccgggcgccg | gcagccagca | 120 |
| cctggaggtc | cgcgacgagg | tggccgagaa | gtgccagaaa | ctgttcctgg | acttcttgga | 180 |
| ggagtttcag | agcagcgatg | gagaaattaa | atacttgcaa | ttagcagagg | aactgattcg | 240 |
| tcctgagaga | aacacattgg | ttgtgagttt | tgtggacctg | aacaattta | accagcaact | 300 |
| ttccaccacc | attcaagagg | agttctatag | agtttaccct | tacctgtgtc | gggccttgaa | 360 |
| aacattcgtc | aaagaccgta | aagagatccc | tcttgccaag | gatttttatg | ttgcattcca | 420 |
| agacctgcct | accagacaca | agattcgaga | gctcacctca | tccagaattg | gtttgctcac | 480 |
| tcgcatcagt | gggcaggtgg | tgcggactca | cccagttcac | ccagagcttg | tgagcggaac | 540 |
| ttttctgtgc | ttggactgtc | agacagtgat | cagggatgta | gaacagcagt | tcaaatacac | 600 |
| acagccaaac | atctgccgaa | atccagtttg | tgccaacagg | aggagattct | tactggatac | 660 |
| aaataaatca | agatttgttg | attttcaaaa | ggttcgtatt | caagagaccc | aagctgagct | 720 |
| tcctcgaggg | agtatccccc | gcagtttaga | agtaatttta | agggctgaag | ctgtggaatc | 780 |
| agctcaagct | ggtgacaagt | gtgactttac | agggacactg | attgttgtgc | ctgacgtctc | 840 |
| caagcttagc | acaccaggag | cacgtgcaga | aactaattcc | cgtgtcagtg | gtgttgatgg | 900 |
| atatgagaca | gaaggcattc | gaggactccg | ggcccttggt | gttagggacc | tttcttatag | 960 |
| gctggtcttt | cttgcctgct | gtgttgcgcc | aaccaaccca | aggtttgggg | ggaaagagct | 1020 |
| cagagatgag | gaacagacag | ctgagagcat | taagaaccaa | atgactgtga | agaatgggga | 1080 |
| gaaagtgttt | gagatgagtc | aagataaaaa | tctataccac | aatctttgta | ccagcctgtt | 1140 |
| ccctactata | catggcaatg | atgaagtaaa | acggggtgtc | ctgctgatgc | tctttggtgg | 1200 |
| cgttccaaag | acaacaggag | aagggacctc | tcttcgaggg | gacataaatg | tttgcattgt | 1260 |
| tggtgaccca | gtacagctaa | agagccaatt | tctcaagcac | gtggaggagt | tcagccccag | 1320 |
| agctgtctac | accagtggta | aagcgtccag | tgctgctggc | ttaacagcag | ctgttgtgag | 1380 |
| agatgaagaa | tctcatgagt | ttgtcattga | ggctggagct | ttgatgttgg | ctgataatgg | 1440 |
| tgtgtgttgt | attgatgaat | ttgataagat | ggacgtgcgg | gatcaagttg | ctattcatga | 1500 |
| agctatggaa | cagcagacca | tatccatcac | taaagcagga | gtgaaggcta | ctctgaacgc | 1560 |
| ccggacgtcc | attttggcag | cagcaaaccc | aatcagtgga | cactatgaca | gatcaaaatc | 1620 |
| attgaaacag | aatataaatt | tgtcagctcc | catcatgtcc | cgattcgatc | tcttctttat | 1680 |
| ccttgtggat | gaatgtaatg | aggttacaga | ttatgccatt | gccaggcgca | tagtagattt | 1740 |
| gcattcaaga | attgaggaat | caattgatcg | tgtctattcc | ctcgatgata | tcagaagata | 1800 |
| tcttctcttt | gcaagacagt | ttaaacccaa | gatttccaaa | gagtcagagg | acttcattgt | 1860 |
| ggagcaatat | aaacatctcc | gccagagaga | tggttctgga | gtgaccaagt | cttcatggag | 1920 |

```
gattacagtg cgacagcttg agagcatgat tcgtctctct gaagctatgg ctcggatgca   1980
ctgctgtgat gaggtccaac ctaaacatgt gaaggaagct ttccggttac tgaataaatc   2040
aatcatccgt gtggaaacac ctgatgtcaa tctagatcaa gaggaagaga tccagatgga   2100
ggtagatgag ggtgctggtg gcatcaatgg tcatgctgac agccctgctc ctgtgaacgg   2160
gatcaatggc tacaatgaag acataaatca gagtctgctc cccaaagcct ccttaaggct   2220
gggcttctct gagtactgcc gaatctctaa ccttattgtg cttcacctca gaaaggtgga   2280
agaagaagag gacgagtcag cattaaagag gagcgagctt gttaactggt acttgaagga   2340
aatcgaatca gagatagact ctgaagaaga acttataaat aaaaaaagaa tcatagagaa   2400
agttattcat cgactcacac actatgatca tgttctaatt gagctcaccc aggctggatt   2460
gaaaggctcc acagagggaa gtgagagcta tgaagaagat ccctacttgg tagttaaccc   2520
taactacttg ctcgaagatt gagatagtga aagtaactga ccagagctga ggaactgtgg   2580
cacagcacct cgtggcctgg agcctggctg gagctctgct agggacagaa gtgtttctgg   2640
aagtgatgct tccaggattt gttttcagaa acaagaattg agttgatggt cctatgtgtc   2700
acattcatca caggtttcat accaacacag gcttcagcac ttcctttggt gtgtttcctg   2760
tcccagtgaa gttggaacca ataatgtgt agtctctata accaataccct ttgttttcat   2820
gtgtaagaaa aggcccatta cttttaaggt atgtgctgtc ctattgagca ataactttt   2880
tttcaattgc cagctactgc ttttattcat caaaataaaa taacttgttc tgaagttgtc   2940
tattggattt ctttctactg taccctgatt attacttcca tctacttctg aatgtgagac   3000
tttccctttt tgcttaacct ggagtgaaga ggtagaactg tggtattatg gatgaggttt   3060
ctatgagaag gagtcattag agaactcata tgaaagctag aggccttaga gatgactttc   3120
caaggttaat tccagttgtt tttttttttt tttaagttta taaagtttta ttatactttt   3180
ttaaaattac tctttagtaa tttatttac ttctgtgtcc taagggtaat ttctcaggat   3240
tgttttcaaa ttgcttttt aggggaaata ggtcatttgc tatattacaa gcaatcccca   3300
aattttatgg tcttccagga aaagttatta ccgtttatga tactaacagt tcctgagact   3360
tagctatgat cagtatgttc atgaggtgga gcagttcctg tgttgcagct tttaacaaca   3420
gatggcattc attaaatcac aaagtatgtt aaaggtcaca aaagcaaaat aactgtctga   3480
ggctaaggcc cacgtgggac agtctaatac ccatgagtac tcaacttgcc ttgatgtctg   3540
agctttccag tgcaatgtga atttgagcag ccagaaatct attagtagaa agcaagacag   3600
attaatatag gttaaaacaa tgatttaaat atgtttctcc caataattat ctctttccct   3660
ggaatcaact tgtatgaaac cttgtcaaaa tgtactccac aagtatgtac aattaagtat   3720
tttaaaaata aatggcaaac attaaaaaca aaaaaaaaaa aaaaaaaa            3769
```

<210> SEQ ID NO 90
<211> LENGTH: 821
<212> TYPE: PRT
<213> ORGANISM: Homo sapiens

<400> SEQUENCE: 90

Met Asp Leu Ala Ala Ala Ala Glu Pro Gly Ala Gly Ser Gln His Leu
  1               5                  10                  15

Glu Val Arg Asp Glu Val Ala Glu Lys Cys Gln Lys Leu Phe Leu Asp
             20                  25                  30

Phe Leu Glu Glu Phe Gln Ser Ser Asp Gly Glu Ile Lys Tyr Leu Gln
         35                  40                  45

```
Leu Ala Glu Glu Leu Ile Arg Pro Glu Arg Asn Thr Leu Val Val Ser
     50                  55                  60
Phe Val Asp Leu Glu Gln Phe Asn Gln Gln Leu Ser Thr Thr Ile Gln
 65                  70                  75                  80
Glu Glu Phe Tyr Arg Val Tyr Pro Tyr Leu Cys Arg Ala Leu Lys Thr
                 85                  90                  95
Phe Val Lys Asp Arg Lys Glu Ile Pro Leu Ala Lys Asp Phe Tyr Val
                100                 105                 110
Ala Phe Gln Asp Leu Pro Thr Arg His Lys Ile Arg Glu Leu Thr Ser
            115                 120                 125
Ser Arg Ile Gly Leu Leu Thr Arg Ile Ser Gly Gln Val Val Arg Thr
        130                 135                 140
His Pro Val His Pro Glu Leu Val Ser Gly Thr Phe Leu Cys Leu Asp
145                 150                 155                 160
Cys Gln Thr Val Ile Arg Asp Val Glu Gln Gln Phe Lys Tyr Thr Gln
                165                 170                 175
Pro Asn Ile Cys Arg Asn Pro Val Cys Ala Asn Arg Arg Phe Leu
            180                 185                 190
Leu Asp Thr Asn Lys Ser Arg Phe Val Asp Phe Gln Lys Val Arg Ile
        195                 200                 205
Gln Glu Thr Gln Ala Glu Leu Pro Arg Gly Ser Ile Pro Arg Ser Leu
    210                 215                 220
Glu Val Ile Leu Arg Ala Glu Ala Val Glu Ser Ala Gln Ala Gly Asp
225                 230                 235                 240
Lys Cys Asp Phe Thr Gly Thr Leu Ile Val Val Pro Asp Val Ser Lys
                245                 250                 255
Leu Ser Thr Pro Gly Ala Arg Ala Glu Thr Asn Ser Arg Val Ser Gly
            260                 265                 270
Val Asp Gly Tyr Glu Thr Glu Gly Ile Arg Gly Leu Arg Ala Leu Gly
        275                 280                 285
Val Arg Asp Leu Ser Tyr Arg Leu Val Phe Leu Ala Cys Cys Val Ala
    290                 295                 300
Pro Thr Asn Pro Arg Phe Gly Gly Lys Glu Leu Arg Asp Glu Glu Gln
305                 310                 315                 320
Thr Ala Glu Ser Ile Lys Asn Gln Met Thr Val Lys Glu Trp Glu Lys
                325                 330                 335
Val Phe Glu Met Ser Gln Asp Lys Asn Leu Tyr His Asn Leu Cys Thr
            340                 345                 350
Ser Leu Phe Pro Thr Ile His Gly Asn Asp Glu Val Lys Arg Gly Val
        355                 360                 365
Leu Leu Met Leu Phe Gly Gly Val Pro Lys Thr Thr Gly Glu Gly Thr
    370                 375                 380
Ser Leu Arg Gly Asp Ile Asn Val Cys Ile Val Gly Asp Pro Ser Thr
385                 390                 395                 400
Ala Lys Ser Gln Phe Leu Lys His Val Glu Glu Phe Ser Pro Arg Ala
                405                 410                 415
Val Tyr Thr Ser Gly Lys Ala Ser Ser Ala Ala Gly Leu Thr Ala Ala
            420                 425                 430
Val Val Arg Asp Glu Glu Ser His Glu Phe Val Ile Glu Ala Gly Ala
        435                 440                 445
Leu Met Leu Ala Asp Asn Gly Val Cys Cys Ile Asp Glu Phe Asp Lys
    450                 455                 460
```

```
Met Asp Val Arg Asp Gln Val Ala Ile His Glu Ala Met Glu Gln Gln
465                 470                 475                 480

Thr Ile Ser Ile Thr Lys Ala Gly Val Lys Ala Thr Leu Asn Ala Arg
            485                 490                 495

Thr Ser Ile Leu Ala Ala Ala Asn Pro Ile Ser Gly His Tyr Asp Arg
        500                 505                 510

Ser Lys Ser Leu Lys Gln Asn Ile Asn Leu Ser Ala Pro Ile Met Ser
            515                 520                 525

Arg Phe Asp Leu Phe Phe Ile Leu Val Asp Glu Cys Asn Glu Val Thr
        530                 535                 540

Asp Tyr Ala Ile Ala Arg Arg Ile Val Asp Leu His Ser Arg Ile Glu
545                 550                 555                 560

Glu Ser Ile Asp Arg Val Tyr Ser Leu Asp Asp Ile Arg Arg Tyr Leu
            565                 570                 575

Leu Phe Ala Arg Gln Phe Lys Pro Lys Ile Ser Lys Glu Ser Glu Asp
        580                 585                 590

Phe Ile Val Glu Gln Tyr Lys His Leu Arg Gln Arg Asp Gly Ser Gly
        595                 600                 605

Val Thr Lys Ser Ser Trp Arg Ile Thr Val Arg Gln Leu Glu Ser Met
        610                 615                 620

Ile Arg Leu Ser Glu Ala Met Ala Arg Met His Cys Cys Asp Glu Val
625                 630                 635                 640

Gln Pro Lys His Val Lys Glu Ala Phe Arg Leu Leu Asn Lys Ser Ile
            645                 650                 655

Ile Arg Val Glu Thr Pro Asp Val Asn Leu Asp Gln Glu Glu Glu Ile
            660                 665                 670

Gln Met Glu Val Asp Glu Gly Ala Gly Gly Ile Asn Gly His Ala Asp
        675                 680                 685

Ser Pro Ala Pro Val Asn Gly Ile Asn Gly Tyr Asn Glu Asp Ile Asn
        690                 695                 700

Gln Glu Ser Ala Pro Lys Ala Ser Leu Arg Leu Gly Phe Ser Glu Tyr
705                 710                 715                 720

Cys Arg Ile Ser Asn Leu Ile Val Leu His Leu Arg Lys Val Glu Glu
            725                 730                 735

Glu Glu Asp Glu Ser Ala Leu Lys Arg Ser Glu Leu Val Asn Trp Tyr
            740                 745                 750

Leu Lys Glu Ile Glu Ser Glu Ile Asp Ser Glu Glu Leu Ile Asn
        755                 760                 765

Lys Lys Arg Ile Ile Glu Lys Val Ile His Arg Leu Thr His Tyr Asp
        770                 775                 780

His Val Leu Ile Glu Leu Thr Gln Ala Gly Leu Lys Gly Ser Thr Glu
785                 790                 795                 800

Gly Ser Glu Ser Tyr Glu Glu Asp Pro Tyr Leu Val Val Asn Pro Asn
            805                 810                 815

Tyr Leu Leu Glu Asp
            820
```

METHODS AND COMPOSITIONS FOR THE DETECTION OF CERVICAL DISEASE

CROSS REFERENCE TO RELATED APPLICATIONS

This application is a divisional application of U.S. Utility application Ser. No. 11/087,227, filed Mar. 23, 2005, which claims the benefit of U.S. Provisional Application Ser. No. 60/556,495, filed Mar. 24, 2004, both of which are incorporated herein by reference in their entirety.

FIELD OF THE INVENTION

The present invention relates to methods and compositions for the detection of high-grade cervical disease.

BACKGROUND OF THE INVENTION

Carcinoma of the cervix is the second most common neoplasm in women, accounting for approximately 12% of all female cancers and causing approximately 250,000 deaths per year. Baldwin et al. (2003) *Nature Reviews Cancer* 3: 1-10. In many developing countries where mass screening programs are not available; the clinical problem is more serious. Cervical cancer in these countries is the number one cause of cancer deaths in women.

The majority of cases of cervical cancer represent squamous cell carcinoma, although adenocarcinoma is also seen. Cervical cancer can be prevented by population screening as it evolves through well-defined noninvasive intraepithelial stages, which can be distinguished morphologically. Williams et al. (1998) *Proc. Natl. Acad. Sci. USA* 95:14932-14937. While it is not understood how normal cells become transformed, the concept of a continuous spectrum of histopathological change from normal, stratified epithelium through cervical intraepithelial neoplasia (CIN) to invasive cancer has been with one or more oncogenic subtypes of HPV, there is a risk for the development of neoplasia in comparison to patients without an HPV infection. Given the importance of HPV in the development of cervical neoplasia, the clinical detection of HPV has become an important diagnostic tool in the identification of patients at risk for cervical neoplasia development. The clinical utility of HPV-based screening for cervical disease is in its negative predictive value. An HPV negative result in combination with a history of normal Pap smears is an excellent indicator of a disease-free condition and a low risk of cervical neoplasia development during the subsequent 1-3 years. However, a positive HPV result is not diagnostic of cervical disease; rather it is an indication of infection. Although the majority of HPV infections is transient and will spontaneously clear within a 12-month period, a persistent infection with a high-risk HPV viral subtype indicates a higher risk for the development of cervical neoplasia. To supplement HPV testing, the identification of molecular markers associated with cervical neoplasia is expected to improve the clinical specificity for cervical disease diagnosis.

Cytological examination of Papanicolaou-stained cervical smears (Pap smears) currently is the method of choice for detecting cervical cancer. The Pap test is a subjective method that has remained substantially unchanged for 60 years. There are several concerns, however, regarding its performance. The reported sensitivity of a single Pap test (the proportion of disease positives that are test-positive) is low and shows wide variation (30-87%). The specificity of a single Pap test (the proportion of disease negatives that are test-negative) might be as low as 86% in a screening population and considerably lower in the ASCUS PLUS population for the determination of underlying high-grade disease. See, Baldwin et al., supra. A significant percentage of Pap smears characterized as LSIL or CINI are actually positive for high-grade lesions. Furthermore, up to 10% of Pap smears are classified as ASCUS (atypical squamous cells of undetermined significance), i.e., it is not possible to make a clear categorization as normal, moderate or severe lesion, or tumor. However, experience shows that up to 10% of this ASCUS population has high-grade lesions, which are consequently overlooked. See, for example, Manos et al. (1999) *JAMA* 281:1605-1610.

Thus, a method for diagnosing high-grade cervical disease that is independent of or works in conjunction with conventional Pap smears and molecular testing for high-risk HPV infection is needed. Such a method should be able to specifically identify high-grade cervical disease that is present in all patient populations, including those cases classified as LSIL or CINI by Pap staining that are actually positive for high-grade lesions (i.e., "false negatives"). Therefore, there is a need in the art for specific, reliable diagnostic methods that are capable of detecting high-grade cervical disease and of differentiating high-grade disease from conditions that are not considered clinical disease, such as early-stage HPV infection and mild dysplasia.

SUMMARY OF THE INVENTION

Compositions and methods for diagnosing high-grade cervical disease are provided. The methods of the invention comprise detecting overexpression of at least one biomarker, particularly a nuclear biomarker, in a body sample, wherein the detection of overexpression of said biomarker specifically identifies samples that are indicative of high-grade cervical disease. The present method distinguishes samples that are indicative of high-grade cervical disease from samples that are indicative of benign proliferation, early-stage HPV infection, or mild dysplasia. Thus, the method relies on the detection of a biomarker that is selectively overexpressed in high-grade cervical disease states but that is not overexpressed in normal cells or cells that are not indicative of clinical disease.

The biomarkers of the invention are proteins and/or genes that are selectively overexpressed in high-grade cervical disease, including those that result from HPV-induced cell cycle dysfunction and activation of certain genes responsible for S-phase induction. Biomarkers of particular interest include S-phase genes, whose overexpression results from HPV-induced cell-cycle dysfunction and the subsequent activation of the transcriptional factors SP-1 and E2F. The detection of overexpression of the biomarker genes or proteins of the invention permits the differentiation of samples that are indicative of high-grade disease, such as moderate to severe dysplasia and cervical carcinomas, from normal cells or cells that are not indicative of clinical disease (e.g., early-stage HPV infection absent dysplasia and mild dysplasia).

Biomarker overexpression can be assessed at the protein or nucleic acid level. In some embodiments, immunocytochemistry techniques are provided that utilize antibodies to detect the overexpression of biomarker proteins in cervical cytology samples. In this aspect of the invention, at least one antibody directed to a specific biomarker of interest is used. Overexpression can also be detected by nucleic acid-based techniques, including, for example, hybridization and RT-PCR. Kits comprising reagents for practicing the methods of the invention are further provided.

The methods of the invention can also be used in combination with traditional gynecological diagnostic techniques that analyze morphological characteristics or HPV infection status. Thus, for example, the immunocytochemistry methods presented here can be combined with the Pap test so that all the morphological information from the conventional method is conserved. In this manner, the detection of biomarkers that are selectively overexpressed in high-grade cervical disease can reduce the high false-negative rate of the Pap test and may facilitate mass automated screening.

BRIEF DESCRIPTION OF THE DRAWINGS

FIG. 1 provides a schematic summary of proliferation and cell cycle de-regulation in cervical dysplasia. Cell cycle alterations and proliferation control defects in cervical neoplasia. HPV infection and over-expression of the E6 and E7 oncoproteins produces a series of alterations in the cell cycle and proliferation control. The HPV E6 oncoprotein abrogates cell cycle checkpoints at the G1/S and G2/M boundaries with subsequent replication of DNA with somatic mutations. E7 promotes the acceleration into the S-phase with prolonged expression of the S-phase genes required for DNA replication (aberrant S-phase induction). Likewise, E6 promotes expression of telomerase ensuring continued chromosomal telomere integrity during proliferation and cellular immortalization. Finally, E7 abrogates the TGF-beta signaling pathway and abrogates this control mechanism for G1 arrest and control of proliferation.

FIG. 2 provides a schematic representation of aberrant S-phase induction in cervical neoplasia. The effects of HPV proteins on cell cycle control and proliferation include inactivation of the p53 and Rb tumor suppressor pathways, activation of E2F-1 transcription, induction of the S-phase genes MCM-2, MCM-6, MCM-7, TOP2A and Cyclin E1 along others. In addition, E2 interacts with the Sp-1 transcription factor to activate gene expression of p21-waf-1.

FIG. 3 provides a schematic representation of the feedback loop on cell proliferation in aberrant S-phase of the cell cycle. Overexpression of Cyclin E and CDK2 in the S-phase results in an independent mechanism to permit induction of the S-phase genes.

FIG. 4 provides a schematic representation of the role of c-myc in aberrant S-phase induction. C-myc is an important transcriptional activator in cellular proliferation. The gene encoding c-myc is located on the chromosome. This is the same site that HPV 18 integration has been documented with a corresponding amplification of this gene region. Amplification of the c-myc gene would result in over-expression of the encoded protein and increased levels of c-myc would independently contribute to S-phase gene transcription further accelerating cellular proliferation.

FIG. 5 provides a schematic representation of TaqMan® primers directed to MCM7 transcript variants.

FIG. 6 illustrates the differential staining pattern of an antibody directed to Claudin 1 in an IHC assay for a patient with mild dysplasia and a patient with squamous cell carcinoma.

FIG. 7 illustrates the differential staining pattern of an antibody directed to Claudin 1 in an IHC and ICC format. Normal cells and cells indicative of CINIII and HSIL are shown.

FIG. 8 illustrates nuclear staining patterns obtained with a nuclear biomarker (i.e., MCM2) and cytoplasmic staining patterns obtained with a cytoplasmic biomarker (p16). Results are from an immunocytochemistry (ICC) assay of a high-grade cervical disease patient sample.

FIG. 9 illustrates desirable and undesirable antibody staining in an immunohistochemistry (IHC) assay using two different antibodies directed to MCM6 on cervical tissue from a patient with high-grade cervical disease.

DETAILED DESCRIPTION OF THE INVENTION

The present invention provides compositions and methods for identifying or diagnosing high-grade cervical disease. The methods comprise the detection of the overexpression of specific biomarkers that are selectively overexpressed in high-grade cervical disease (e.g., moderate to severe dysplasia and cervical cancer). That is, the biomarkers of the invention are capable of distinguishing between HPV-infected cells and HPV-infected cells that are pre-malignant, malignant, or overtly cancerous. Methods for diagnosing high-grade cervical disease involve detecting the overexpression of at least one biomarker that is indicative of high-grade cervical disease in a tissue or body fluid sample from a patient. In particular embodiments, antibodies and immunocytochemistry techniques are used to detect expression of the biomarker of interest. Kits for practicing the methods of the invention are further provided.

"Diagnosing high-grade cervical disease" is intended to include, for example, diagnosing or detecting the presence of cervical disease, monitoring the progression of the disease, and identifying or detecting cells or samples that are indicative of high-grade cervical disease. The terms diagnosing, detecting, and identifying high-grade cervical disease are used interchangeably herein. By "high-grade cervical disease" is intended those conditions classified by colposcopy as premalignant pathology, malignant pathology, moderate to severe dysplasia, and cervical cancer. Underlying high-grade cervical disease includes histological identification of CINII, CINIII, HSIL, carcinoma in situ, adenocarcinoma, and cancer (FIGO stages I-IV).

As discussed above, a significant percentage of patients presenting with Pap smears classified as normal, CINI, or ASCUS actually have lesions characteristic of high-grade cervical disease. Thus, the methods of the present invention permit the identification of high-grade cervical disease in all patient populations, including these "false negative" patients, and facilitate the detection of rare abnormal cells in a patient sample. The diagnosis can be made independent of cell morphology and HPV infection status, although the methods of the invention can also be used in conjunction with conventional diagnostic techniques, e.g., Pap test, molecular testing for high-risk types of HPV, etc.

HPV types have been divided into high and low-risk categories based on their association with cervical cancer and precancerous lesions. Low-risk HPV types include types 6, 11, 42, 43, 44 and are not associated with an increased risk of cervical cancer. In contrast, high-risk HPV types, including types 16, 18, 31, 33, 35, 39, 45, 51, 52, 56, 58, 59, 68, have been strongly associated with cervical cancer and squamous intraepithelial lesions. See, for example, Wright et al. (2004) *Obstet. Gynecol.* 103:304-309. In fact, over 99% of cervical cancers are associated with high-risk HPV infection. Persistent high-risk HPV infection leads to the disruption of the cell cycle and mitotic checkpoints in cervical cells through the action of HPV genes E2, E6, and E7. In particular, HPV E7 causes an increase in cyclin E and the subsequent release of the transcription factor E2f from the retinoblastoma (Rb) protein. The released E2f transcription factor then triggers the transcription of a variety of S-phase genes, including topoisomerase II alpha (Topo2A), MCM proteins, cyclins E1 and E2, and p14arf, resulting in loss of cell cycle control. HPV E2 further stimulates overexpression of S-phase genes such as $p21^{waf-1}$ by activating the Sp-1 transcription factor. The cell cycle disruption caused by persistent HPV infection can lead to mild cervical dysplasia that may then progress to moderate or severe dysplasia and eventually to cervical cancer in some cases. By "cervical cancer" is intended any cancer or cancerous lesion associated with cervical tissue or cervical cells.

HPV infection within cervical keratinocytes results in a number of alterations that disrupt the activities within the cell cycle. The E6 and E7 oncoproteins of the high-risk HPV subtypes have been implicated in a number of cellular processes related to increased proliferation and neoplastic transformation of the infected keratinocytes. The E6 protein has been implicated in two critical processes. The first is the degradation of the p53 tumor suppressor protein through ubiquitin-mediated proteolysis. Removal of functional p53 eliminates a major cell cycle checkpoint responsible for DNA repair prior to entry into DNA replication and mitosis (Duensing and Munger (2003) *Prog Cell Cycle Res.* 5:383-391). In addition, E6 has been shown to interact with the c-myc protein and is responsible for direct transcriptional activation of the hTERT gene with subsequent expression of telomerase (McMurray and McCance (2003) *J Virol.* 77:9852-9861; Veldman et al. (2003) *Proc Natl Acad Sci U.S.A.* 100: 8211-8216). Activation of telomerase is a key step in cancer biology responsible for the maintenance of telomere length on replicating chromosomes and this enzyme ensures functionally intact chromosomes during cellular immortalization.

The HPV oncoprotein E7 is known to contribute to cellular proliferation through two independent mechanisms. The first is the inactivation of the TGF-beta tumor suppressor pathway responsible for cell cycle arrest at the G1 phase through direct interaction of E7 with the Smad proteins (Smad 2, 3 and 4), thereby inhibiting their ability to bind to DNA (Lee et al. (2002) *J Biol Chem.* 277:38557-38564). Likewise, E7 is known to specifically interact with the Rb tumor suppressor protein. Within the G1 phase of the cell cycle, Rb complexes the E2F transcription factor and prevents E2F from activating gene transcription. At the G1/S boundary, the Rb protein is phosphorylated with release of the E2F transcription factor—thereby initiating E2F gene transcription and entry into the S phase of the cell cycle. The HPV E7 oncoprotein abrogates this control mechanism by directly binding with Rb and displacing E2F from the complex. This results in E2F driven gene transcription independent of normal cell cycle control (Duensing and Munger (2003) *Prog Cell Cycle Res.* 5:383-391; Duensing and Munger (2004) *Int J Cancer* 109:157-162; Clarke and Chetty (2001) *Gynecol Oncol.* 82:238-246). This release of E2F uncouples gene transcription from cell cycle control and results in prolonged and aberrant transcription of S-phase genes responsible for DNA synthesis and cellular proliferation. In addition, the combined actions of both E6 and E7 have been shown to contribute to centrosome abnormalities and the subsequent genomic instability in cervical neoplasia (Duensing and Munger (2004) *Int J Cancer* 109: 157-162).

While not intending to be limited to a particular mechanism, in some embodiments, the molecular behavior of high-grade cervical disease can be characterized as the overexpression of discrete genes, normally expressed only during the S-phase of the cell cycle, as a result of infection by oncogenic strains of HPV. The subsequent uncontrolled activation of gene transcription and aberrant S-phase induction is mediated through the E2F-1 transcription factor pathway. This behavior appears to be indicative of high-grade cervical disease and provides a link between oncogenic HPV infections and the molecular behavior of cervical neoplasia. The use of these molecular biomarkers of cervical neoplasia in molecular diagnostic assay formats can improve the detection of cervical disease with an improved sensitivity and specificity over current methods. See generally FIGS. 1-4 and Malinowski (2005) *BioTechniques* 38:1-8 (in press), which is herein incorporated by reference in its entirety. Thus, in particular embodiments, a method for diagnosing high-grade cervical disease comprises detecting overexpression of a biomarker, wherein overexpression of the biomarker is indicative of aberrant S-phase induction, as described herein. In still other embodiments, the methods comprise detecting overexpression of a biomarker, wherein overexpression of the biomarker is indicative of active transcription or overexpression of the HPV E6 and HPV E7 genes.

Dysplasia is conventionally defined in morphological terms by a loss of normal orientation of epithelial cells, accompanied by alterations in cellular and nuclear size, shape, and staining characteristics. Dysplasia is graded according to the degree of the cellular abnormalities (i.e., mild, moderate, severe) and is widely accepted to be an intermediate stage in the progression from normal tissue to neoplasia, as evidenced by the identification of pre-malignant dysplastic conditions such as CIN. The methods of the present invention permit the identification of high-grade cervical disease, which includes moderate to severe dysplasia and cervical cancer (i.e., CINII conditions and above), based on the overexpression of biomarkers that are specific to high-grade cervical disease.

The methods disclosed herein provide superior detection of high-grade cervical disease in comparison to PAP smears and/or HPV infection testing. In particular aspects of the invention, the sensitivity and specificity of the present methods are equal to or greater than that of conventional Pap smears. As used herein, "specificity" refers to the level at which a method of the invention can accurately identify samples that have been confirmed as NIL by colposcopy (i.e., true negatives). That is, specificity is the proportion of disease negatives that are test-negative. In a clinical study, specificity is calculated by dividing the number of true negatives by the sum of true negatives and false positives. By "sensitivity" is intended the level at which a method of the invention can accurately identify samples that have been colposcopy-confirmed as positive for high-grade cervical disease (i.e., true positives). Thus, sensitivity is the proportion of disease positives that are test-positive. Sensitivity is calculated in a clinical study by dividing the number of true positives by the sum of true positives and false negatives. See Examples 1-3 below. In some embodiments, the sensitivity of the disclosed methods for the detection of high-grade cervical disease is preferably at least about 70%, more preferably at least about 80%, most preferably at least about 90, 91, 92, 93, 94, 95, 96, 97, 98, 99% or more. Furthermore, the specificity of the present methods is preferably at least about 70%, more preferably at least about 80%, most preferably at least about 90, 91, 92, 93, 94, 95, 96, 97, 98, 99% or more.

The term "positive predictive value" or "PPV" refers to the probability that a patient has high-grade cervical disease when restricted to those patients who are classified as positive using a method of the invention. PPV is calculated in a clinical study by dividing the number of true positives by the sum of true positives and false positives. In some embodiments, the PPV of a method of the invention for diagnosing high-grade cervical disease is at least about 40%, while maintaining a sensitivity of at least about 90%, more particularly at least about 95%. The "negative predictive value" or "NPV" of a test is the probability that the patient will not have the disease when restricted to all patients who test negative. NPV is calculated in a clinical study by dividing the number of true negatives by the sum of true negatives and false negatives.

The biomarkers of the invention include genes and proteins, and variants and fragments thereof. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides.

A "biomarker" is any gene or protein whose level of expression in a tissue or cell is altered compared to that of a normal or healthy cell or tissue. Biomarkers of the invention are selective for underlying high-grade cervical disease. By "selectively overexpressed in high-grade cervical disease" is intended that the biomarker of interest is overexpressed in high-grade cervical disease but is not overexpressed in conditions classified as LSIL, CINI, HPV-infected samples without any dysplasia present, immature metaplastic cells, and other conditions that are not considered to be clinical disease. Thus, detection of the biomarkers of the invention permits the differentiation of samples indicative of underlying high-grade cervical disease from samples that are indicative of benign proliferation, early-stage HPV infection, or mild dysplasia. By "early-stage HPV infection" is intended HPV infection that has not progressed to cervical dysplasia. As used herein, "mild dysplasia" refers to LSIL and CINI where no high-grade lesion is present. The methods of the invention also distinguish cells indicative of high-grade disease from normal cells, immature metaplastic cells, and other cells that are not indicative of clinical disease. In this manner, the methods of the invention permit the accurate identification of high-grade cervical disease, even in cases mistakenly classified as normal, CINI, LSIL, or ASCUS by traditional Pap testing (i.e., "false negatives"). In some embodiments, the methods for diagnosing high-grade cervical disease are performed as a reflex to an abnormal or atypical Pap smear. That is, the methods of the invention may be performed in response to a patient having an abnormal or atypical Pap smear result. In other aspects of the invention, the methods are performed as a primary screening test for high-grade cervical disease in the general population of women, just as the conventional Pap test is performed currently.

The biomarkers of the invention include any gene or protein that is selectively overexpressed in high-grade cervical disease, as defined herein above. Such biomarkers are capable of identifying cells within a cytology cell suspension that are pre-malignant, malignant, or overtly cancerous. The biomarkers of the invention detect cells of CINII conditions and above, but do not detect CINI and HPV-infected cells where there is no underlying high-grade disease. Biomarkers of particular interest include genes and proteins involved in cell cycle regulation, HPV disruption of the cell cycle, DNA replication and transcription, and signal transduction. In some embodiments, the biomarkers are S-phase genes, including those genes whose expression is stimulated by the E2f transcription factor or the Sp-1 transcription factor. Nuclear biomarkers may be used to practice certain aspects of the invention. By "nuclear biomarker" is intended a biomarker that is predominantly expressed in the nucleus of the cell. A nuclear widely accepted for years. The precursor to cervical cancer is dysplasia, also known in the art as CIN or squamous intraepithelial lesions (SIL). Squamous intraepithelial abnormalities may be classified by using the three-tiered (CIN) or two-tiered (Bethesda) system. Under the Bethesda system, low-grade squamous intraepithelial lesions (LSIL), corresponding to CINI and HPV infection, generally represent productive HPV infections with a relatively low risk of progression to invasive disease. High-grade squamous intraepithelial lesions (HSIL), corresponding to CINII and CINIII in the three-tiered system, show a higher risk of progression to cervical cancer than do LSIL, although both LSIL and HSIL are viewed as potential precursors of malignancy. Patient samples may also be classified as ASCUS (atypical squamous cells of unknown significance) or AGUS (atypical glandular cells of unknown significance) under this system.

A strong association of cervical cancer and infection by high-risk types of human papilloma virus (HPV), such as types 16, 18, and 31, has been established. In fact, a large body of epidemiological and molecular biological evidence has established HPV infection as a causative factor in cervical cancer. Moreover, HPV is found in 85% or more of the cases of high-grade cervical disease. However, HPV infection is very common, possibly occurring in 5-15% of women over the age of 30, but few HPV-positive women will ever develop high-grade cervical disease or cancer. The presence of HPV alone is indicative only of infection, not of high-grade cervical disease, and, therefore, testing for HPV infection alone results in many false positives. See, for example, Wright et al. (2004) *Obstet. Gynecol.* 103:304-309.

Current literature suggests that HPV infects the basal stem cells within the underlying tissue of the uterine-cervix. Differentiation of the stem cells into mature keratinocytes, with resulting migration of the cells to the stratified cervical epithelium, is associated with HPV viral replication and re-infection of cells. During this viral replication process, a number of cellular changes occur that include cell-cycle de-regulation, active proliferation, DNA replication, transcriptional activation and genomic instability (Crum (2000) *Modern Pathology* 13:243-251; Middleton et al (2003) *J. Virol.* 77:10186-10201; Pett et al. (2004) *Cancer Res.* 64:1359-1368).

Most HPV infections are transient in nature, with the viral infection resolving itself within a 12-month period. For those individuals who develop persistent infections biomarker may be expressed to a lesser degree in other parts of the cell. Although any biomarker indicative of high-grade cervical disease may be used in the present invention, in certain embodiments the biomarkers, particularly nuclear biomarkers, are selected from the group consisting of MCM2, MCM6, MCM7, $p21^{waf1}$, topoisomerase II alpha (Topo2A), $p14^{arf}$, and cyclin E. More particularly, the biomarker may comprise an MCM protein.

Minichromosome maintenance (MCM) proteins play an essential part in eukaryotic DNA replication. The minichromosome maintenance (MCM) proteins function in the early stages of DNA replication through loading of the prereplication complex onto DNA and functioning as a helicase to help unwind the duplex DNA during de novo synthesis of the duplicate DNA strand. Each of the MCM proteins has DNA-dependent ATPase motifs in their highly conserved central domain. Levels of MCM proteins generally increase in a variable manner as normal cells progress from G0 into the G1/S phase of the cell cycle. In the G0 phase, MCM2 and MCM5 proteins are much less abundant than are the MCM7 and MCM3 proteins. MCM6 forms a complex with MCM2, MCM4, and MCM7, which binds histone H3. In addition, the subcomplex of MCM4, MCM6, and MCM7 has helicase activity, which is mediated by the ATP-binding activity of MCM6 and the DNA-binding activity of MCM4. See, for example, Freeman et al. (1999) *Clin. Cancer Res.* 5:2121-2132; Lei et al. (2001) *J. Cell Sci.* 114:1447-1454; Ishimi et al. (2003) *Eur. J. Biochem.* 270:1089-1101, all of which are herein incorporated by reference in their entirety.

Early publications have shown that the MCM proteins, and in particular, MCM-5, are useful for the detection of cervical disease (Williams et al. (1998) *Proc Natl Acad Sci U.S.A.* 95:14932-14937), as well as other cancers (Freeman et al. (1999) *Clin Cancer Res.* 5:2121-2132). The published literature indicates that antibodies to MCM-5 are capable of detecting cervical neoplastic cells. The specificity for detection of high-grade cervical disease has not been demonstrated for MCM-5 (Williams et al. (1998) *Proc Natl Acad Sci U.S.A.* 95:14932-14937). The detection of MCM-5 expression is not restricted to high-grade cervical disease but is also detected in identified low-grade dysplasia and proliferative cells that have re-entered the cell cycle following infection with high-risk HPV. The detection of cervical neoplasia with antibodies to MCM-5 is shown in FIG. 4. In addition to MCM-5, other members from the MCM family, including MCM-2 and MCM-7 have been shown to be potentially useful markers for the detection of cervical neoplasia in tissue samples (Freeman et al. (1999) *Clin Cancer Res.* 5:2121-2132; Brake et al. (2003) *Cancer Res.* 63:8173-8180). Recent results have shown that MCM-7 appears to be a specific marker for the detection of high-grade cervical disease using immunochemistry formats (Brake et al. (2003) *Cancer Res.* 63:8173-8180; Malinowski et al. (2004) *Acta Cytol.* 43:696).

Topoisomerase II alpha (Topo2a) is an essential nuclear enzyme involved in DNA replication and is a target for many anti-cancer drugs used for cancer therapy. Decreased expression of Topo2a is a predominant mechanism of resistance to several chemotherapeutic agents. A significant variation in the range of expression of this protein has been noted in many different tumors. Topo2a is predominant in proliferating cells and is modified in M phase by phosphorylation at specific sites, which is critical for mitotic chromosome condensation and segregation.

p21 is a protein encoded by the WAF1/Cip1 gene on chromosome 6p. This gene was shown to inhibit the activity of several cyclin/cyclin-dependent kinase complexes and to block cell cycle progression. The expression of $p21^{waf1}$ mediates the cell cycle arrest function of p53. Because p21 appears to mediate several of the growth-regulatory functions of p53, its expression may reflect the functional status of p53 more precisely than p53 accumulation. Furthermore, $p21^{waf1}$ can inhibit DNA replication by blocking the action of proliferating cell nuclear antigen (PCNA).

Cyclin E is a regulatory subunit of cdk-2 and controls G1/S transition during the mammalian cell cycle. Multiple isoforms of Cyclin E are expressed only in tumors but not in the normal tissues, suggesting a post-transcriptional regulation of Cyclin E. In vitro analyses indicated that these truncated variant isoforms of Cyclin E are able to phosphorylate histone H1. Alterations in Cyclin E proteins have been implicated as indicators of poor prognosis in various cancers.

Although the above biomarkers have been discussed in detail, any biomarker that is overexpressed in high-grade cervical disease states (e.g., CINII, CINIII, and cervical carcinomas) may be used in the practice of the invention. Other biomarkers of interest include cell cycle regulated genes that are specific to the G1/S phase boundary or to S-phase. Such genes include but are not limited to helicase (DD×11), uracil DNA glycolase (UNG), E2F5, cyclin E1 (CCNE1), cyclin E2 (CCNE2), CDC25A, CDC45L, CDC6, p21 WAF-1 (CDKN1A), CDKN3, E2F1, MCM2, MCM6, NPAT, PCNA, stem loop BP (SLBP), BRCA1, BRCA2, CCNG2, CDKN2C, dihydrofolate reductase (DHFR), histone H1, histone H2A, histone H2B, histone H3, histone H4, MSH2, NASP, ribonucleotide reductase M1 (RRM1), ribonucleotide reductase M2 (RRM2), thymidine synthetase (TYMS), replication factor C4 (RFC4), RAD51, chromatin Factor 1A (CHAF1A), chromatin Factor 1B (CHAF1B), topisomerase III (TOP3A), ORC1, primase 2A (PRIM2A), CDC27, primase 1 (PRIM1), flap structure endonuclease (FEN1), fanconi anemia comp. grp A (FNACA), PKMYT1, and replication protein A2 (RPA2). See, for example, Whitfield et al. (2002) *Mol. Biol. Cell* 13:1977-2000, herein incorporated by reference in its entirety. Other S phase genes of interest include cyclin-dependent kinase 2 (CDK2), MCM3, MCM4, MCM5, DNA polymerase I alpha (DNA POL1), DNA ligase 1, B-Myb, DNA methyl transferase (DNA MET), pericentrin (PER), KIF4, DP-1, ID-3, RAN binding protein (RANBP1), gap junction alpha 6 (GJA6), amino levulinate dehydratase (ALDH), histone 2A Z (H2A.Z), spermine synthase (SpmS), proliferin 2, T-lymphocyte activation protein, phospholipase A2 (PLA2), and L6 antigen (L6). See, for example, Nevins et al. (2001) *Mol. Cell. Biol.* 21:4689-4699, herein incorporated by reference.

In some aspects of the invention, the biomarkers comprise genes that are induced by the E2f transcription factor. Such genes include but are not limited to thymidylate synthase, thymidine kinase 1, ribonucleotide reductase M1, ribonucleotide reductase M2, CDK2, cyclin E, MCM3, MCM7, PCNA, DNA primase small subunit, topoisomerase II A (Topo2A), DNA ligase 1, flap endonuclease 1, RAD51, CDC2, cyclin A2, cyclin B1, cyclin B2, KI-67, KIFC1, FIN16, BUB1, importin alpha-2, HMG2, enhancer of zeste, STK-1, histone stem-loop BP, Rb, P18-INK4C, annexin VIII, c-Myb, CDC25A, cyclin D3, cyclin E1, deoxycytosine kinase, DP-1, endothelin converting enzyme, enolase 2, P18 INK4C, ribonucleotide reductase, and uracil DNA glycolase 2. See, for example Nevins et al., supra; Muller et al. (2000) *Genes and Dev.* 15:267-285. In particular embodiments the biomarker of interest is a gene induced by E2f transcription factor that is involved in cell cycle regulation and DNA replication, such as, for example, cyclin E2, Ki-67, p57KIP2, RANBPM, and replication protein A1. Some E2f-induced genes of interest are involved in apoptosis, including APAF1, Bcl-2, caspase 3, MAP3 Kinase 5, and TNF receptor associated factor. Other E2f-induced genes are involved in the regulation of transcription and include, for example, ash2 like, polyhomeotic 2, embryonic ectoderm protein, enhancer of zeste, hairy/enhancer of split, homeobox A110, homeobox A7, homeobox A9, homeodomain TF1, pre-B-cell leukemia FT3, YY1 TF, POU domain TF, TAFII130, TBP-factor 172, basic TF3, bromodomain/zinc finger, SWI/SNF, ID4, TEA-4, NFATC1, NFATC3, BT, CNC-1, MAF, MAFF, MAFG, core binding protein, E74-like factor 4, c-FOS, JUNB, zinc finger DNA BP, and Cbp/p300 transactivator. E2f-induced genes involved in signal transduction are also potential biomarkers of interest and include TGF beta, follistatin, bone morphogenetic protein 2, BMP receptor type 1A, frizzled homolog 1, WNT10B, sphingosine kinase 1, dual specificity phosphatase 7, dual specificity (Y) phosphatase, FGF Receptor 3, protein tyrosine phosphatase, dual specificity (Y) phosphatase D6655, insulin receptor, mature T-cell proliferation 1, FGF receptor 2, TGF alpha, CDC42 effector protein 3, Met, CD58, CD83, TACC1, and TEAD4.

Although the methods of the invention require the detection of at least one biomarker in a patient sample for the detection of high-grade cervical disease, 2, 3, 4, 5, 6, 7, 8, 9, 10 or more biomarkers may be used to practice the present invention. It is recognized that detection of more than one biomarker in a body sample may be used to identify instances of high-grade cervical disease. Therefore, in some embodiments, two or more biomarkers are used, more preferably, two or more complementary biomarkers. By "complementary" is intended that detection of the combination of biomarkers in a body sample results in the successful identification of high-grade cervical disease in a greater percentage of cases than would be identified if only one of the biomarkers was used. Thus, in some cases, a more accurate determination of high-grade cervical disease can be made by using at least two biomarkers. Accordingly, where at least two biomarkers are used, at least two antibodies directed to distinct biomarker proteins will be used to practice the immunocytochemistry methods disclosed herein. The antibodies may be contacted with the body sample simultaneously or concurrently. In certain aspects of the invention, the overexpression of MCM2 and Topo2A is detected using three antibodies, wherein two of the antibodies are specific for MCM2 and the third antibody is specific for Topo2A.

In particular embodiments, the diagnostic methods of the invention comprise collecting a cervical sample from a patient, contacting the sample with at least one antibody specific for a biomarker of interest, and detecting antibody binding. Samples that exhibit overexpression of a biomarker of the invention, as determined by detection of antibody binding, are deemed positive for high-grade cervical disease. In particular embodiments, the body sample is a monolayer of cervical cells. In some aspects of the invention, the monolayer of cervical cells is provided on a glass slide.

By "body sample" is intended any sampling of cells, tissues, or bodily fluids in which expression of a biomarker can be detected. Examples of such body samples include but are not limited to blood, lymph, urine, gynecological fluids, biopsies, and smears. Body samples may be obtained from a patient by a variety of techniques including, for example, by scraping or swabbing an area or by using a needle to aspirate bodily fluids. Methods for collecting various body samples are well known in the art. In particular embodiments, the body sample comprises cervical cells, as cervical tissue samples or as cervical cells in suspension, particularly in a liquid-based preparation. In one embodiment, cervical samples are collected according to liquid-based cytology specimen preparation guidelines such as, for example, the SurePath® (TriPath Imaging, Inc.) or the ThinPrep® preparation (CYTYC, Inc.). Body samples may be transferred to a glass slide for viewing under magnification. Fixative and staining solutions may be applied to the cells on the glass slide for preserving the specimen and for facilitating examination. In one embodiment the cervical sample will be collected and processed to provide a monolayer sample, as set forth in U.S. Pat. No. 5,346,831, herein incorporated by reference.

The monolayer method relates to a method for producing a monolayer of cytological material on a cationically-charged substrate. The method comprises the steps of separating the cytological material by centrifugation over a density gradient, producing a packed pellet of the cytological material, mixing the pellet of the cytological material, withdrawing an aliquot of a predetermined volume from the mixed pellet, depositing the aliquot and a predetermined volume of water into a sedimentation vessel, which is removably secured to the cationically-charged substrate, allowing the cytological material to settle onto the substrate under the force of gravity, and after settlement of the cytological material, removing the water from the sedimentation vessel. For automated analysis, the sedimentation vessel may be detached from the substrate. Disaggregation may be by any methods known in the art, such as syringing, trypsinizing, ultrasonication, shaking, vortexing, or by use of the device described in copending U.S. Pat. No. 5,316,814, the contents of which are herein incorporated by reference. In some embodiments, slides comprising a monolayer of cervical cells are prepared from SurePath™ (TriPath Imaging, Inc.) samples using the PrepStain™ slide processor (TriPath Imaging, Inc.).

Any methods available in the art for identification or detection of the biomarkers are encompassed herein. The overexpression of a biomarker of the invention can be detected on a nucleic acid level or a protein level. In order to determine overexpression, the body sample to be examined may be compared with a corresponding body sample that originates from a healthy person. That is, the "normal" level of expression is the level of expression of the biomarker in cervical cells of a human subject or patient not afflicted with high-grade cervical disease. Such a sample can be present in standardized form. In some embodiments, particularly when the body sample comprises a monolayer of cervical cells, determination of biomarker overexpression requires no comparison between the body sample and a corresponding body sample that originates from a healthy person. In this situation, the monolayer of cervical cells from a single patient may contain as few as 1-2 abnormal cells per 50,000 normal cells present. Detection of these abnormal cells, identified by their overexpression of a biomarker of the invention, precludes the need for comparison to a corresponding body sample that originates from a healthy person.

Methods for detecting biomarkers of the invention comprise any methods that determine the quantity or the presence of the biomarkers either at the nucleic acid or protein level. Such methods are well known in the art and include but are not limited to western blots, northern blots, southern blots, ELISA, immunoprecipitation, immunofluorescence, flow cytometry, immunocytochemistry, nucleic acid hybridization techniques, nucleic acid reverse transcription methods, and nucleic acid amplification methods. In particular embodiments, overexpression of a biomarker is detected on a protein level using, for example, antibodies that are directed against specific biomarker proteins. These antibodies can be used in various methods such as Western blot, ELISA, immunoprecipitation, or immunocytochemistry techniques. Likewise, immunostaining of cervical smears can be combined with conventional Pap stain methods so that morphological information and immunocytochemical information can be obtained. In this manner, the detection of the biomarkers can reduce the high false-negative rate of the Pap smear test and may facilitate mass automated screening.

In one embodiment, antibodies specific for biomarker proteins are utilized to detect the overexpression of a biomarker protein in a body sample. The method comprises obtaining a body sample from a patient, contacting the body sample with at least one antibody directed to a biomarker that is selectively overexpressed in high-grade cervical disease, and detecting antibody binding to determine if the biomarker is overexpressed in the patient sample. A preferred aspect of the present invention provides an immunocytochemistry technique for diagnosing high-grade cervical disease. Specifically, this method comprises antibody staining of biomarkers within a patient sample that are specific for high-grade cervical disease. One of skill in the art will recognize that the immunocytochemistry method described herein below may be performed manually or in an automated fashion using, for example, the Autostainer Universal Staining System (Dako) or the Biocare Nemesis Autostainer (Biocare). One protocol for antibody staining (i.e., immunocytochemistry) of cervical samples is provided in Example 1.

In a preferred immunocytochemistry method, a patient cervical sample is collected into a liquid medium, such as, for example, in a SurePath™ collection vial (TriPath Imaging, Inc.). An automated processor such as the PrepStain™ system (TriPath Imaging, Inc.) is used to collect cells from the liquid medium and to deposit them in a thin layer on a glass slide for further analysis. Slide specimens may be fixed or unfixed and may be analyzed immediately following preparation or may be stored for later analysis. In some embodiments, prepared slides are stored in 95% ethanol for a minimum of 24 hours. Alternatively, in other embodiments, slides are stored in a pretreatment buffer, as described below.

Samples may need to be modified in order to make the biomarker antigens accessible to antibody binding. In a particular aspect of the immunocytochemistry methods, slides are transferred to a pretreatment buffer, for example the SureSlide® Preparation Buffer (TriPath Imaging, Inc.) and optionally heated to increase antigen accessibility. Heating of the sample in the pretreatment buffer rapidly disrupts the lipid bi-layer of the cells and makes the antigens (i.e., biomarker proteins) more accessible for antibody binding. The pretreatment buffer may comprise a polymer, a detergent, or a non-ionic or anionic surfactant such as, for example, an ethyloxylated anionic or nonionic surfactant, an alkanoate or an alkoxylate or even blends of these surfactants or even the use of a bile salt. In particular embodiments, the pretreatment buffer comprises a nonionic or anionic detergent, such as sodium alkanoate with an approximate molecular weight of 183 kD blended with an alkoxylate with an approximate molecular weight of 370 kD (hereafter referred to as RAM). In a particular embodiment, the pretreatment buffer comprises 1% RAM. In some embodiments, the pretreatment buffer may also be used as a slide storage buffer, as indicated above. In another embodiment a solution of 0.1% to 1% of deoxycholic acid, sodium salt, monohydrate was used as both a storage buffer as well as a pretreatment buffer. In yet another embodiment of the invention a solution of sodium laureth-13-carboxylate (e.g., Sandopan LS) or and ethoxylated anionic complex or even an alkylaryl ethoxlate carboxylic acid can be used for the storage and pretreatment buffers. In a particular aspect of the invention, the slide pretreatment buffer comprises 0.05% to 5% sodium laureth-13-carboxylate, particularly 0.1% to 1% sodium laureth-13-carboxylate, more particularly 0.5% sodium laureth-13-carboxylate. In one embodiment the slides can be stored in the buffer for up to 72 hours prior to the pretreatment and staining process. The pretreatment buffers of the invention may be used in methods for making antigens more accessible for antibody binding in an immunoassay, such as, for example, an immunocytochemistry method or an immunohistochemistry method. See Example 14. The terms "pretreatment buffer" and "preparation buffer" are used interchangeably herein to refer to a buffer that is used to prepare cytology or histology samples for immunostaining, particularly by increasing antigen accessibility for antibody binding.

Any method for making antigens more accessible for antibody binding may be used in the practice of the invention, including the antigen retrieval methods known in the art. See, for example, Bibbo et al. (2002) *Acta. Cytol.* 46:25-29; Saqi et al. (2003) *Diagn. Cytopathol.* 27:365-370; Bibbo et al. (2003) *Anal. Quant. Cytol. Histol.* 25:8-11, herein incorporated by reference in their entirety. In some embodiments, antigen retrieval comprises storing the slides in 95% ethanol for at least 24 hours, immersing the slides in 1× Target Retrieval Solution pH 6.0 (DAKO S1699)/dH2O bath preheated to 95° C., and placing the slides in a steamer for 25 minutes. See Example 2 below.

Following pretreatment or antigen retrieval to increase antigen accessibility, samples are blocked using an appropriate blocking agent, e.g., a peroxidase blocking reagent such as hydrogen peroxide. In some embodiments, the samples are blocked using a protein blocking reagent to prevent non-specific binding of the antibody. The protein blocking reagent may comprise, for example, purified casein. An antibody, particularly a monoclonal antibody, directed to a biomarker of interest is then incubated with the sample. As noted above, one of skill in the art will appreciate that a more accurate diagnosis of high-grade cervical disease may be obtained in some cases by detecting more than one biomarker in a patient sample. Therefore, in particular embodiments, at least two antibodies directed to two distinct biomarkers are used to detect high-grade cervical disease. Where more than one antibody is used, these antibodies may be added to a single sample sequentially as individual antibody reagents or simultaneously as an antibody cocktail. See Example 3 below. Alternatively, each individual antibody may be added to a separate sample from the same patient, and the resulting data pooled. In particular embodiments, an antibody cocktail comprises at least three antibodies, wherein two antibodies specifically bind to MCM2 and a third antibody specifically binds to Topo2A.

Techniques for detecting antibody binding are well known in the art. Antibody binding to a biomarker of interest may be detected through the use of chemical reagents that generate a detectable signal that corresponds to the level of antibody binding and, accordingly, to the level of biomarker protein expression. In one of the immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Enzymes of particular interest include horseradish peroxidase (HRP) and alkaline phosphatase (AP). Commercial antibody detection systems, such as, for example the Dako Envision+ system and Biocare Medical's Mach 3 system, may be used to practice the present invention.

In one particular immunocytochemistry method of the invention, antibody binding to a biomarker is detected through the use of an HRP-labeled polymer that is conjugated to a secondary antibody. Antibody binding can also be detected through the use of a mouse probe reagent, which binds to mouse monoclonal antibodies, and a polymer conjugated to HRP, which binds to the mouse probe reagent. Slides are stained for antibody binding using the chromogen 3,3-diaminobenzidine (DAB) and then counterstained with hematoxylin and, optionally, a bluing agent such as ammonium hydroxide or TBS/Tween-20. In some aspects of the invention, slides are reviewed microscopically by a cytotechnologist and/or a pathologist to assess cell staining (i.e., biomarker overexpression) and to determine if high-grade cervical disease is present. Alternatively, samples may be reviewed via automated microscopy or by personnel with the assistance of computer software that facilitates the identification of positive staining cells.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Antibody derivatives may comprise a protein or chemical moiety conjugated to the antibody.

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. Polypeptides of the latter kind are, for example, produced at low levels by the lymph system and at increased levels by myelomas.

The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing.

The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize 35 readily. Pepsin treatment yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them.

Polyclonal antibodies can be prepared by immunizing a suitable subject (e.g., rabbit, goat, mouse, or other mammal) with a biomarker protein immunogen. The antibody titer in the immunized subject can be monitored over time by standard techniques, such as with an enzyme linked immunosorbent assay (ELISA) using immobilized biomarker protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550-52; Kenneth (1980) in *Monoclonal Antibodies: A New Dimension In Biological Analyses* (Plenum Publishing Corp., NY); and Lerner (1981) *Yale J. Biol. Med.*, 54:387-402).

Alternative to preparing monoclonal antibody-secreting hybridomas, a monoclonal antibody can be identified and isolated by screening a recombinant combinatorial immunoglobulin library (e.g., an antibody phage display library) with a biomarker protein to thereby isolate immunoglobulin library members that bind the biomarker protein. Kits for generating and screening phage display libraries are commercially available (e.g., the Pharmacia *Recombinant Phage Antibody System*, Catalog No. 27-9400-01; and the Stratagene *SurfZAP I Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^3$H.

In regard to detection of antibody staining in the immunocytochemistry methods of the invention, there also exist in the art, video-microscopy and software methods for the quantitative determination of an amount of multiple molecular species (e.g., biomarker proteins) in a biological sample wherein each molecular species present is indicated by a representative dye marker having a specific color. Such methods are also known in the art as a colorimetric analysis methods. In these methods, video-microscopy is used to provide an image of the biological sample after it has been stained to visually indicate the presence of a particular biomarker of interest. Some of these methods, such as those disclosed in U.S. patent application Ser. No. 09/957,446 to Marcelpoil et al. and U.S. patent application Ser. No. 10/057,729 to Marcelpoil et al., incorporated herein by reference, disclose the use of an imaging system and associated software to determine the relative amounts of each molecular species present based on the presence of representative color dye markers as indicated by those color dye markers' optical density or transmittance value, respectively, as determined by an imaging system and associated software. These techniques provide quantitative determinations of the relative amounts of each molecular species in a stained biological sample using a single video image that is "deconstructed" into its component color parts.

The antibodies used to practice the invention are selected to have high specificity for the biomarker proteins of interest. Methods for making antibodies and for selecting appropriate antibodies are known in the art. See, for example, Celis, ed. (in press) *Cell Biology & Laboratory Handbook*, 3rd edition (Academic Press, New York), which is herein incorporated in its entirety by reference. In some embodiments, commercial antibodies directed to specific biomarker proteins may be used to practice the invention. The antibodies of the invention may be selected on the basis of desirable staining of cytological, rather than histological, samples. That is, in particular embodiments the antibodies are selected with the end sample type (i.e., cytology preparations) in mind and for binding specificity.

In some aspects of the invention, antibodies directed to specific biomarkers of interest are selected and purified via a multi-step screening process. In particular embodiments, polydomas are screened to identify biomarker-specific antibodies that possess the desired traits of specificity and sensitivity. As used herein, "polydoma" refers to multiple hybridomas. The polydomas of the invention are typically provided in multi-well tissue culture plates. In the initial antibody screening step, a tumor tissue microarray comprising multiple normal (i.e., no CIN), CINIII, squamous cell carcinoma, and adenocarcinoma samples is generated. Methods and equipment, such as the Chemicon® Advanced Tissue Arrayer, for generating arrays of multiple tissues on a single slide are known in the art. See, for example, U.S. Pat. No. 4,820,504. Undiluted supernatants from each well containing a polydoma are assayed for positive staining using standard immunohistochemistry techniques. At this initial screening step, background, non-specific binding is essentially ignored. Polydomas producing positive results are selected and used in the second phase of antibody screening.

In the second screening step, the positive polydomas are subjected to a limiting dilution process. The resulting unscreened antibodies are assayed for positive staining of CINIII or cervical carcinoma samples using standard immunohistochemistry techniques. At this stage, background staining is relevant, and the candidate polydomas that only stain positive for abnormal cells (i.e., CINIII and cancer cells) only are selected for further analysis.

To identify antibodies that can distinguish normal and CINI samples from those indicative of high-grade cervical disease (i.e., CINII and above), a disease panel tissue microarray is generated. This tissue microarray typically comprises multiple no CIN, CINI, CINII, CINIII, squamous cell carcinoma, and adenocarcinoma samples. Standard immunohistochemistry techniques are employed to assay the candidate polydomas for specific positive staining of samples indicative of high-grade cervical disease only (i.e., CINII samples and above). Polydomas producing positive results and minimal background staining are selected for further analysis.

Positive-staining cultures are prepared as individual clones in order to select individual candidate monoclonal antibodies. Methods for isolating individual clones are well known in the art. The supernatant from each clone comprising unpurified antibodies is assayed for specific staining of CINII, CINIII, squamous cell carcinoma, and adenocarcinoma samples using the tumor and disease panel tissue microarrays described herein above. Candidate antibodies showing positive staining of high-grade cervical disease samples (i.e., CINII and above), minimal staining of other cell types (i.e., normal and CINI samples), and little background are selected for purification and further analysis. Methods for purifying antibodies through affinity adsorption chromatography are well known in the art.

In order to identify antibodies that display maximal specific staining of high-grade cervical disease samples and minimal background, non-specific staining in cervical cytology samples, the candidate antibodies isolated and purified in the immunohistochemistry-based screening process above are assayed using the immunocytochemistry techniques of the present invention. Exemplary protocols for performing immunocytochemistry are provided in Examples 1 and 2.

Specifically, purified antibodies of interest are used to assay a statistically significant number of NIL (i.e., no invasive lesion), ASCUS, LSIL, HSIL or cancerous cervical cytology patient samples. The samples are analyzed by immunocytochemistry as described herein and classified as positive, negative, or indeterminate for high-grade cervical disease on the basis of positive antibody staining for a particular biomarker. Sensitivity, specificity, positive predictive values, and negative predictive values for each antibody are calculated. Antibodies exhibiting maximal specific staining of high-grade cervical disease in cervical cytology samples with minimal background (i.e., maximal signal to noise ratio) are selected for the present invention.

Identification of appropriate antibodies results in an increase in signal to noise ratio and an increase in the clinical utility of the assay. Assay format and sample type to be used are critical factors in selection of appropriate antibodies. Many antibodies directed to biomarkers do not produce a desirable signal to noise ratio in an immunocytochemistry format with cytology preparations or in an immunohistochemistry format with formalin-fixed paraffin-embedded samples. Moreover, biomarker antibodies that produce a maximal signal to noise ratio in an immunohistochemistry format may not work as well in immunocytochemistry assays. For example, an antibody that produces the desired level of staining in an immunocytochemistry format may not produce the appropriate level of staining in an immunohistochemistry assay (data not shown). Likewise, an antibody that produces an acceptable signal to noise ratio when used in the immunohistochemistry assay may result in overstaining of immunocytochemistry samples (data not shown). Thus, antibody selection requires early consideration of the assay format and the end sample type to be used.

Cytology-based assays (i.e., immunocytochemistry) differ from tissue-based assays (i.e., immunohistochemistry) insofar as the tissue architecture is not available to assist with staining interpretation in the immunocytochemistry format. For example, in an immunohistochemistry assay performed on samples from patients with mild dysplasia or squamous cell carcinoma with an antibody directed to Claudin 1, the results indicated that Claudin 1 was expressed in the lesion of the mild dysplasia sample (i.e., light brown staining) but was significantly overexpressed (i.e., dark brown staining) in the cancer lesion (FIG. 12). The results obtained with the same Claudin 1 antibody in an immunocytochemistry assay format were indeterminate (FIG. 13). While abnormal cells are easily detectable using a Claudin 1 antibody in an immunohistochemistry assay, the results obtained by the staining of Claudin 1 in the immunocytochemistry assay of the invention were more difficult to interpret. Therefore, biomarkers that are appropriate in an immunohistochemistry format may not be suitable in an immunocytochemistry assay and, thus, are not included in the preferred embodiment of the invention.

Furthermore, the location of biomarkers within the cell is also an important consideration in immunocytochemistry assays. Biomarkers that display nuclear, cytoplasmic, or membrane staining patterns can be confirmed morphologically and are appropriate for immunohistochemistry methods. Cytoplasmic and membrane staining, however, make it difficult to identify critical morphological characteristics of cervical disease (e.g., nuclear to cytoplasmic ratio) in immunocytochemistry assays. See FIG. 15. In contrast, biomarkers that are expressed in the nucleus and show a nuclear staining pattern facilitate detection of antibody staining and also permit morphological analysis. See FIG. 15. Thus, in some preferred embodiments, only biomarkers that are selectively expressed in the nucleus are used in an immunocytochemistry assay of the invention.

One of skill in the art will recognize that optimization of antibody titer and detection chemistry is needed to maximize the signal to noise ratio for a particular antibody. Antibody concentrations that maximize specific binding to the biomarkers of the invention and minimize non-specific binding (or "background") will be determined. In particular embodiments, appropriate antibody titers for use in cervical cytology preparations are determined by initially testing various antibody dilutions on formalin-fixed paraffin-embedded normal and high-grade cervical disease tissue samples. Optimal antibody concentrations and detection chemistry conditions are first determined for formalin-fixed paraffin-embedded cervical tissue samples. The design of assays to optimize antibody titer and detection conditions is standard and well within the routine capabilities of those of ordinary skill in the art. After the optimal conditions for fixed tissue samples are determined, each antibody is then used in cervical cytology preparations under the same conditions. Some antibodies require additional optimization to reduce background staining and/or to increase specificity and sensitivity of staining in the cytology samples.

Furthermore, one of skill in the art will recognize that the concentration of a particular antibody used to practice the methods of the invention will vary depending on such factors as time for binding, level of specificity of the antibody for the biomarker protein, and method of body sample preparation. Moreover, when multiple antibodies are used, the required concentration may be affected by the order in which the antibodies are applied to the sample, i.e., simultaneously as a cocktail or sequentially as individual antibody reagents. Furthermore, the detection chemistry used to visualize antibody binding to a biomarker of interest must also be optimized to produce the desired signal to noise ratio.

In other embodiments, the expression of a biomarker of interest is detected at the nucleic acid level. Nucleic acid-based techniques for assessing expression are well known in the art and include, for example, determining the level of biomarker mRNA in a body sample. Many expression detection methods use isolated RNA. Any RNA isolation technique that does not select against the isolation of mRNA can be utilized for the purification of RNA from cervical cells (see, e.g., Ausubel et al., ed., (1987-1999) *Current Protocols in Molecular Biology* (John Wiley & Sons, New York). Additionally, large numbers of tissue samples can readily be processed using techniques well known to those of skill in the art, such as, for example, the single-step RNA isolation process of Chomczynski (1989, U.S. Pat. No. 4,843,155).

The term "probe" refers to any molecule that is capable of selectively binding to a specifically intended target biomolecule, for example, a nucleotide transcript or a protein encoded by or corresponding to a biomarker. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker of the present invention. Hybridization of an mRNA with the probe indicates that the biomarker in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of biomarker mRNA in a sample involves the process of nucleic acid amplification, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan® System). Such methods typically utilize pairs of oligonucleotide primers that are specific for the biomarker of interest. Methods for designing oligonucleotide primers specific for a known sequence are well known in the art.

Biomarker expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of biomarker expression may also comprise using nucleic acid probes in solution.

In one embodiment of the invention, microarrays are used to detect biomarker expression. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety for all purposes. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation of an all-inclusive device. See, for example, U.S. Pat. Nos. 5,856,174 and 5,922,591 herein incorporated by reference.

In one approach, total mRNA isolated from the sample is converted to labeled cRNA and then hybridized to an oligonucleotide array. Each sample is hybridized to a separate array. Relative transcript levels may be calculated by reference to appropriate controls present on the array and in the sample.

Kits for practicing the methods of the invention are further provided. By "kit" is intended any manufacture (e.g., a package or a container) comprising at least one reagent, e.g., an antibody, a nucleic acid probe, etc. for specifically detecting the expression of a biomarker of the invention. The kit may be promoted, distributed, or sold as a unit for performing the methods of the present invention. Additionally, the kits may contain a package insert describing the kit and methods for its use.

In a particular embodiment, kits for practicing the immunocytochemistry methods of the invention are provided. Such kits are compatible with both manual and automated immunocytochemistry techniques (e.g., cell staining) as described below in Example 1. These kits comprise at least one antibody directed to a biomarker of interest, chemicals for the detection of antibody binding to the biomarker, a counterstain, and, optionally, a bluing agent to facilitate identification of positive staining cells. Any chemicals that detect antigen-antibody binding may be used in the practice of the invention. In some embodiments, the detection chemicals comprise a labeled polymer conjugated to a secondary antibody. For example, a secondary antibody that is conjugated to an enzyme that catalyzes the deposition of a chromogen at the antigen-antibody binding site may be provided. Such enzymes and techniques for using them in the detection of antibody binding are well known in the art. In one embodiment, the kit comprises a secondary antibody that is conjugated to an HRP-labeled polymer. Chromogens compatible with the conjugated enzyme (e.g., DAB in the case of an HRP-labeled secondary antibody) and solutions, such as hydrogen peroxide, for blocking non-specific staining may be further provided. In other embodiments, antibody binding to a biomarker protein is detected through the use of a mouse probe reagent that binds to mouse monoclonal antibodies, followed by addition of a dextran polymer conjugated with HRP that binds to the mouse probe reagent. Such detection reagents are commercially available from, for example, Biocare Medical.

The kits of the present invention may further comprise a peroxidase blocking reagent (e.g., hydrogen peroxide), a protein blocking reagent (e.g., purified casein), and a counterstain (e.g., hematoxylin). A bluing agent (e.g., ammonium hydroxide or TBS, pH 7.4, with Tween-20 and sodium azide) may be further provided in the kit to facilitate detection of positive staining cells.

In another embodiment, the immunocytochemistry kits of the invention additionally comprise at least two reagents, e.g., antibodies, for specifically detecting the expression of at least two distinct biomarkers. Each antibody may be provided in the kit as an individual reagent or, alternatively, as an antibody cocktail comprising all of the antibodies directed to the different biomarkers of interest. Furthermore, any or all of the kit reagents may be provided within containers that protect them from the external environment, such as in sealed containers. An exemplary kit for practicing the methods of the invention is described below in Example 8.

Positive and/or negative controls may be included in the kits to validate the activity and correct usage of reagents employed in accordance with the invention. Controls may include samples, such as tissue sections, cells fixed on glass slides, etc., known to be either positive or negative for the presence of the biomarker of interest. In a particular embodiment, the positive control comprises SiHa cells. This is a human cervical squamous cancer cell line that is hypertriploid and positive for HPV-16 infection and, therefore, serves as a positive control for the overexpression of biomarkers in high-grade cervical disease states. SiHa control cells may be provided in the kits of the invention as prepared slides or as a cell suspension that is compatible with slide preparation. The design and use of controls is standard and well within the routine capabilities of those of ordinary skill in the art.

In other embodiments, kits for identifying high-grade cervical comprising detecting biomarker overexpression at the nucleic acid level are further provided. Such kits comprise, for example, at least one nucleic acid probe that specifically binds to a biomarker nucleic acid or fragment thereof. In particular embodiments, the kits comprise at least two nucleic acid probes that hybridize with distinct biomarker nucleic acids.

In some embodiments, the methods of the invention can be used in combination with traditional cytology techniques that analyze morphological characteristics. For example, the immunocytochemical techniques of the present invention can be combined with the conventional Pap stain so that all the morphological information from the conventional method is conserved. In this manner the detection of biomarkers can reduce the high false-negative rate of the Pap smear test and may facilitate mass automated screening. In a particular embodiment, the immunocytochemistry methods disclosed herein above are combined with the conventional Pap stain in a single method, as described below in Example 6-7. A combined immunocytochemistry and Pap staining method permits visualization of both biomarkers that are selectively overexpressed in high-grade cervical disease and cell morphology in a single sample (e.g., a microscope slide comprising a monolayer of cervical cells). The combined immunocytochemistry and Pap staining method may permit the more accurate identification and diagnosis of high-grade cervical disease, particularly in cases mistakenly classified as normal, LSIL, or ASCUS by conventional Pap testing. Analysis of both biomarker overexpression and cell morphology in a single method could replace the Pap smear as the primary screening method for cervical cancer.

One of skill in the art will recognize that the staining parameters (e.g., incubation times, wash conditions, chromogen/stain concentrations, etc.) for this combined methodology will need to be optimized such that a sufficient contrast between the immunocytochemistry output (e.g., chromogen staining) and the Pap stain is obtained. The design of assays to optimize staining parameters is standard and well within the routine capabilities of those of ordinary skill in the art. Kits for performing the combined immunocytochemistry and Pap staining method are also encompassed by the present invention. Such kits comprise the reagents needed for immunocytochemistry, as described herein above, and the reagents for conventional Pap staining, particularly EA50 and Orange G.

One of skill in the art will further appreciate that any or all steps in the methods of the invention could be implemented by personnel or, alternatively, performed in an automated fashion. Thus, the steps of body sample preparation, sample staining, and detection of biomarker expression may be automated.

The following examples are offered by way of illustration and not by way of limitation:

EXPERIMENTAL

Example 1

Detection of Biomarker Overexpression Using Immunocytochemistry

Slide Preparation and Pretreatment

Patient cervical samples are collected and placed into a SurePath™ collection vial (TriPath Imaging, Inc.). Cervical cells are collected from the liquid medium and deposited in a thin layer on a glass slide using the PrepStain™ slide processor system (TriPath Imaging, Inc.). Prepared slides are immediately transferred to a pretreatment buffer (1% RAM) and heated for 45 minutes at 95° C. The slides are cooled to room temperature and rinsed three times (2 minutes per rinse) in TBS (tris buffered saline).

Manual Immunocytochemistry

To prevent non-specific background staining, slides are not permitted to dry out during the staining procedure. Furthermore, in order to block non-specific staining, hydrogen peroxide is applied to the slides for 5 minutes, followed by a TBS rinse. An antibody directed to MCM6 is applied to the slide for 1 hour at room temperature. Following incubation with the MCM6 antibody, the slide is washed three times with TBS for 2 minutes per wash. The Dako Envision+ HRP-labeled polymer secondary antibody is applied to the slide for 30 minutes at room temperature, followed by a TBS rinse. The HRP substrate chromogen DAB is applied for 10 minutes, and then the slides are rinsed for 5 minutes with water. Each slide is counterstained with hematoxylin and then rinsed with water until clear. Following counterstaining, the slides are soaked in ammonium hydroxide for 10 seconds and then rinsed with water for 1 minute.

Samples are dehydrated by immersing the slides in 95% ethanol for 1 minute and then in absolute ethanol for an additional minute. Slides are cleared by rinsing 3 times in xylene for 1 minute per rinse. Slides are then coverslipped with permanent mounting media and incubated at 35° C. to dry. Positive staining cells are visualized using a bright-field microscope.

Automated Immunocytochemistry

The Dako Autostainer Universal Staining system is programmed according to the manufacturer's instructions, and the necessary staining and counterstaining reagents described above for manual immunocytochemistry are loaded onto the machine. The prepared and pretreated slides are loaded onto the Autostainer, and the program is run. At the end of the run, the slides are removed and rinsed in water for 5 minutes. The slides are dehydrated, cleared, coverslipped, and analyzed as described above.

Example 2

Detection of Biomarkers in Clinical Samples

Approximately 180 cervical cytology patient samples representing various diagnoses were collected. The presence or absence of cancerous cells or lesions indicative of high-grade disease in these patients was previously confirmed by colposcopy. The following table indicates the number of samples within each diagnosis group analyzed in this study, as well as a description of the colposcopy findings (e.g., presence or absence of high-grade lesions).

TABLE 1

| Specimens analyzed | | |
|---|---|---|
| Diagnosis | Count | Description |
| NIL | 72 | HPV Negative |
| ASC-US | 26 | 26 without lesion |
|  |  | 0 with lesion or high risk HPV |
| LSIL | 48 | 42 negative for high grade lesion |
|  |  | 6 positive for high grade lesion |
| HSIL | 25 |  |
| Cancer | 10 | Squamous Cell Carcinoma and Adenocarcinoma |

The samples were analyzed by immunocytochemistry methods to identify high-grade cervical disease. Antibodies were used to detect the overexpression of six biomarkers of interest: MCM2, MCM6, MCM 7, $p21^{waf1}$, Cyclin E, and Topo2A. Assay controls included MCM2, MCM6, MCM7, $p21^{waf1}$, Cyclin E, Topo2A and a mouse IgG negative run on the SiHa cell line. Samples were also analyzed by traditional Pap staining techniques.

Preparation of Slides

Each sample was removed from storage and allowed to come to room temperature. 6 ml of TriPath CytoRich® preservative was added to each vial, and the vials were vortexed. Samples were processed on the TriPath PrepMate® automated processor, and any remaining fluid in the vial was transferred to a centrifuge tube. The samples were centrifuged for 2 minutes at 200× g, and the supernatant was aspirated. The samples were then centrifuged for 10 minutes at 800× g, and the supernatant was decanted. Sample tubes were loaded onto the TriPath PrepStain® system and the system software (version 1.1; Transfer Only) was run. Eight slides for each patient sample were prepared and stored in 95% ethanol for at least 24 hours but not longer than 2 weeks prior to use in Pap staining and immuocytochemistry methods.

Pap Staining Method

Prepared slides were incubated in 95% ethanol for 30 seconds and then rinsed with water for an additional 30 seconds. Hematoxylin was applied to the slides for 6 minutes. Slides were rinsed in water for 1 minute, acid water for 2 seconds, and water for 30 seconds. A bluing agent (ammonium hydroxide) was applied for 30 seconds, and the slides were rinsed first in water and then in 95% ethanol for 30 seconds each. EA 50 and Orange G (Autocyte®) were applied for 6 minutes. The slides were rinsed 2 times in 95% ethanol, 3 times in 100% ethanol, and 3 times in xylene for 30 seconds per rinse.

The slides were then coverslipped using Acrytol mounting media and incubated at 35° C. to dry. Samples were reviewed by a pathologist using a bright-field microscope.

Immunocytochemistry Method

Prepared slides were removed from the 95% ethanol and rinsed with deionized water for approximately 1 minute. Slides were placed in a 1× Target Retrieval Solution pH 6.0 (DAKO S1699)/dH20 bath preheated to 95° C. and placed in a steamer for 25 minutes. Samples were allowed to cool for 20 minutes at room temperature, rinsed well in deionized water, and placed in TBS. Pretreated slides were stained for biomarker expression essentially as described above in Example 1, "Automated Immunocytochemistry." Commercial antibodies directed to MCM2 (1:200), MCM7 (1:25), p21waf1 (1:100), and cylcin E (1:100) were diluted as indicated and used to detect biomarker expression. Purified MCM6 antibody, identified by polydoma screening as described in Example 4, was used at a 1:6000 dilution.

Interpretation of Slides

Each slide was screened and reviewed by a cytotechnologist and a pathologist. Samples were classified as positive, negative, or indeterminate for high-grade cervical disease according to the following parameters:

- Non-cellular artifacts and inflammatory cells staining brown (DAB) were disregarded.
- Mature, normal-appearing squamous cells and normal-appearing glandular cells were not counted as positive when staining with DAB.
- Squamous metaplastic cells along with abnormal cells were considered positive.
- A staining intensity of less than 1.5 was considered negative.
- Discrepant results were resolved through joint review of slides.

The immunocytochemistry results were compared with the results previously obtained by colposcopy. Each slide was then given a final result of true positive (TP), true negative (TN), false positive (FP), false negative (FN), or indeterminate. Sensitivity, specificity, positive predictive values, and negative predictive values for each biomarker were calculated.

Results

The results for each biomarker are summarized below.

TABLE 2

MCM2

| | TP | FP | FN | TN | Indeter. | Totals |
|---|---|---|---|---|---|---|
| NIL | 0 | 0 | 0 | 71 | 1 | 72 |
| ASC-US (No Lesion) | 0 | 0 | 0 | 25 | 1 | 26 |
| ASC-US (Lesion) | 0 | 0 | 0 | 0 | 0 | 0 |
| LSIL (No HSIL) | 0 | 7 | 0 | 31 | 4 | 42 |
| LSIL (HSIL) | 3 | 0 | 3 | 0 | 0 | 6 |
| HSIL | 24 | 0 | 1 | 0 | 0 | 25 |
| Cancer | 7 | 0 | 1 | 0 | 2 | 10 |
| | 34 | 7 | 5 | 127 | 8 | 181 |

Sensitivity 0.8718
Specificity 0.9478
PPV 0.8293
NPV 0.9621

TABLE 3

MCM6

| | TP | FP | FN | TN | Indeter. | Totals |
|---|---|---|---|---|---|---|
| NIL | 0 | 0 | 0 | 68 | 4 | 72 |
| ASC-US (No Lesion) | 0 | 3 | 0 | 22 | 1 | 26 |
| ASC-US (Lesion) | 0 | 0 | 0 | 0 | 0 | 0 |
| LSIL (No HSIL) | 0 | 14 | 0 | 24 | 4 | 42 |
| LSIL (HSIL) | 3 | 0 | 2 | 0 | 1 | 6 |
| HSIL | 22 | 0 | 0 | 0 | 3 | 25 |
| Cancer | 10 | 0 | 0 | 0 | 0 | 10 |
| | 35 | 17 | 2 | 114 | 13 | 181 |

Sensitivity 0.9459
Specificity 0.8702
PPV 0.6731
NPV 0.9828

TABLE 4

MCM7

| | TP | FP | FN | TN | Indeter. | Totals |
|---|---|---|---|---|---|---|
| NIL | 0 | 0 | 0 | 67 | 5 | 72 |
| ASC-US (No Lesion) | 0 | 2 | 0 | 21 | 3 | 26 |
| ASC-US (Lesion) | 0 | 0 | 0 | 0 | 0 | 0 |
| LSIL (No HSIL) | 0 | 12 | 0 | 28 | 2 | 42 |
| LSIL (HSIL) | 4 | 0 | 2 | 0 | 0 | 6 |
| HSIL | 24 | 0 | 1 | 0 | 0 | 25 |
| Cancer | 9 | 0 | 0 | 0 | 1 | 10 |
| | 37 | 14 | 3 | 116 | 11 | 181 |

Sensitivity 0.9250
Specificity 0.8923
PPV 0.7255
NPV 0.9748

TABLE 5

Cyclin E

| | TP | FP | FN | TN | Indeter. | Totals |
|---|---|---|---|---|---|---|
| NIL | 0 | 0 | 0 | 72 | 0 | 72 |
| ASC-US (No Lesion) | 0 | 0 | 0 | 26 | 0 | 26 |
| ASC-US (Lesion) | 0 | 0 | 0 | 0 | 0 | 0 |
| LSIL (No HSIL) | 0 | 3 | 0 | 35 | 4 | 42 |
| LSIL (HSIL) | 2 | 0 | 4 | 0 | 0 | 6 |
| HSIL | 15 | 0 | 4 | 0 | 6 | 25 |
| Cancer | 7 | 0 | 2 | 0 | 1 | 10 |
| | 24 | 3 | 10 | 133 | 11 | 181 |

Sensitivity 0.7059
Specificity 0.9779
PPV 0.8889
NPV 0.9301

TABLE 6

$p21^{waf1}$

| | TP | FP | FN | TN | Indeter. | Totals |
|---|---|---|---|---|---|---|
| NIL | 0 | 2 | 0 | 61 | 9 | 72 |
| ASC-US (No Lesion) | 0 | 1 | 0 | 22 | 3 | 26 |
| ASC-US (Lesion) | 0 | 0 | 0 | 0 | 0 | 0 |
| LSIL (No HSIL) | 0 | 12 | 0 | 23 | 7 | 42 |
| LSIL (HSIL) | 3 | 0 | 3 | 0 | 0 | 6 |

TABLE 6-continued p21$^{waf1}$

|  | TP | FP | FN | TN | Indeter. | Totals |
|---|---|---|---|---|---|---|
| HSIL | 21 | 0 | 1 | 0 | 3 | 25 |
| Cancer | 7 | 0 | 2 | 0 | 1 | 10 |
|  | 31 | 15 | 6 | 106 | 23 | 181 |

| Sensitivity | 0.8378 |
|---|---|
| Specificity | 0.8760 |
| PPV | 0.6739 |
| NPV | 0.9464 |

TABLE 7

TOPO2A

|  | TP | FP | FN | TN | Indeter. | Totals |
|---|---|---|---|---|---|---|
| NIL | 0 | 0 | 0 | 68 | 4 | 72 |
| ASC-US (No Lesion) | 0 | 1 | 0 | 24 | 1 | 26 |
| ASC-US (Lesion) | 0 | 0 | 0 | 0 | 0 | 0 |
| LSIL (No HSIL) | 0 | 4 | 0 | 27 | 11 | 42 |
| LSIL (HSIL) | 3 | 0 | 3 | 0 | 0 | 6 |
| HSIL | 21 | 0 | 1 | 0 | 3 | 25 |
| Cancer | 9 | 0 | 0 | 0 | 1 | 10 |
|  | 33 | 5 | 4 | 119 | 20 | 181 |

| Sensitivity | 0.8919 |
|---|---|
| Specificity | 0.9597 |
| PPV | 0.8684 |
| NPV | 0.9675 |

Approximately 180 cases were analyzed for the presence of high-grade cervical disease using the immunocytochemistry methods of the invention. Of that number, the MCM biomarkers produced an indeterminate rate ranging from 4% to 7%. Additionally, MCM2 showed a specificity of 95% with a sensitivity of 87%. The MCM6 and MCM7 biomarkers produced comparable sensitivity results of 95% and 93%, respectively. The specificity for these two biomarkers ranged from 87% to 89%.

Cyclin E produced the highest specificity value of 98%. Although the indeterminate rate was 6%, the sensitivity was only 71%. The indeterminate rate for p21$^{waf1}$ was the highest of all markers tested at 13%. p21$^{waf1}$ produced a sensitivity of 84% and a specificity of 88%. 96% specificity was observed with the biomarker Topo2A. The indeterminate rate for Topo2A was 11%, with a sensitivity of 89%.

Example 3

Detection of Biomarkers in Clinical Samples Using Antibody Cocktails

Approximately 180 colposcopy-confirmed cervical cytology samples were analyzed by immunocytochemistry methods to identify high-grade cervical disease. Each sample was analyzed for the expression of multiple biomarkers of interest. Specifically, various combinations of antibodies directed to MCM2, MCM6, MCM 7, p21waf1, Cyclin E, and Topo2A were analyzed for their ability to detect high-grade cervical disease. These samples were evaluated for the expression of multiple biomarkers of interest using the immunocytochemistry methods and slide interpretation guidelines described in Example 2.

The immunocytochemistry results were compared with the results previously obtained by colposcopy. Each slide was then given a final result of true positive (TP), true negative (TN), false positive (FP), false negative (FN), or indeterminate. Sensitivity, specificity, positive predictive values, and negative predictive values for each biomarker were calculated.

Results

The results for each biomarker are summarized below.

TABLE 8

MCM2 and MCM7

|  | TP | FP | FN | TN | Indeter. | Totals |
|---|---|---|---|---|---|---|
| NIL | 0 | 0 | 0 | 66 | 6 | 72 |
| ASC-US (No Lesion) | 0 | 2 | 0 | 20 | 4 | 26 |
| ASC-US (Lesion) | 0 | 0 | 0 | 0 | 0 | 0 |
| LSIL (No HSIL) | 0 | 13 | 0 | 25 | 4 | 42 |
| LSIL (HSIL) | 4 | 0 | 2 | 0 | 0 | 6 |
| HSIL | 24 | 0 | 1 | 0 | 0 | 25 |
| Cancer | 10 | 0 | 0 | 0 | 0 | 10 |
|  | 38 | 15 | 3 | 111 | 14 | 181 |

| Sensitivity | 0.9268 |
|---|---|
| Specificity | 0.8810 |
| PPV | 0.7170 |
| NPV | 0.9737 |

TABLE 9

MCM6 and MCM7

|  | TP | FP | FN | TN | Indeter. | Totals |
|---|---|---|---|---|---|---|
| NIL | 0 | 0 | 0 | 65 | 7 | 72 |
| ASC-US (No Lesion) | 0 | 3 | 0 | 21 | 2 | 26 |
| ASC-US (Lesion) | 0 | 0 | 0 | 0 | 0 | 0 |
| LSIL (No HSIL) | 0 | 16 | 0 | 23 | 3 | 42 |
| LSIL (HSIL) | 4 | 0 | 2 | 0 | 0 | 6 |
| HSIL | 24 | 0 | 0 | 0 | 1 | 25 |
| Cancer | 10 | 0 | 0 | 0 | 0 | 10 |
|  | 38 | 19 | 2 | 109 | 13 | 181 |

| Sensitivity | 0.9500 |
|---|---|
| Specificity | 0.8516 |
| PPV | 0.6667 |
| NPV | 0.9820 |

TABLE 10

MCM7 and TOPO2A

|  | TP | FP | FN | TN | Indeter. | Totals |
|---|---|---|---|---|---|---|
| NIL | 0 | 0 | 0 | 64 | 8 | 72 |
| ASC-US (No Lesion) | 0 | 2 | 0 | 21 | 3 | 26 |
| ASC-US (Lesion) | 0 | 0 | 0 | 0 | 0 | 0 |
| LSIL (No HSIL) | 0 | 12 | 0 | 29 | 1 | 42 |
| LSIL (HSIL) | 4 | 0 | 2 | 0 | 0 | 6 |
| HSIL | 20 | 0 | 2 | 0 | 3 | 25 |
| Cancer | 8 | 0 | 0 | 0 | 2 | 10 |
|  | 32 | 14 | 4 | 114 | 17 | 181 |

| Sensitivity | 0.8889 |
|---|---|
| Specificity | 0.8906 |
| PPV | 0.6957 |
| NPV | 0.9661 |

TABLE 11

MCM7 and Cyclin E

|  | TP | FP | FN | TN | Indeter. | Totals |
|---|---|---|---|---|---|---|
| NIL | 0 | 0 | 0 | 67 | 5 | 72 |
| ASC-US (No Lesion) | 0 | 2 | 0 | 21 | 3 | 26 |
| ASC-US (Lesion) | 0 | 0 | 0 | 0 | 0 | 0 |
| LSIL (No HSIL) | 0 | 12 | 0 | 28 | 2 | 42 |
| LSIL (HSIL) | 4 | 0 | 2 | 0 | 0 | 6 |
| HSIL | 24 | 0 | 1 | 0 | 0 | 25 |
| Cancer | 10 | 0 | 0 | 0 | 0 | 10 |
|  | 38 | 14 | 3 | 116 | 10 | 181 |

Sensitivity 0.9268
Specificity 0.8923
PPV 0.7308
NPV 0.9748

TABLE 12

MCM7 and p21waf1

|  | TP | FP | FN | TN | Indeter. | Totals |
|---|---|---|---|---|---|---|
| NIL | 0 | 2 | 0 | 57 | 13 | 72 |
| ASC-US (No Lesion) | 0 | 3 | 0 | 20 | 3 | 26 |
| ASC-US (Lesion) | 0 | 0 | 0 | 0 | 0 | 0 |
| LSIL (No HSIL) | 0 | 14 | 0 | 21 | 7 | 42 |
| LSIL (HSIL) | 4 | 0 | 2 | 0 | 0 | 6 |
| HSIL | 24 | 0 | 1 | 0 | 0 | 25 |
| Cancer | 9 | 0 | 0 | 0 | 1 | 10 |
|  | 37 | 19 | 3 | 98 | 24 | 181 |

Sensitivity 0.9250
Specificity 0.8376
PPV 0.6607
NPV 0.9703

TABLE 13

MCM2 and MCM6

|  | TP | FP | FN | TN | Indeter. | Totals |
|---|---|---|---|---|---|---|
| NIL | 0 | 0 | 0 | 67 | 5 | 72 |
| ASC-US (No Lesion) | 0 | 3 | 0 | 21 | 2 | 26 |
| ASC-US (Lesion) | 0 | 0 | 0 | 0 | 0 | 0 |
| LSIL (No HSIL) | 0 | 17 | 0 | 21 | 4 | 42 |
| LSIL (HSIL) | 3 | 0 | 2 | 0 | 1 | 6 |
| HSIL | 24 | 0 | 0 | 0 | 1 | 25 |
| Cancer | 10 | 0 | 0 | 0 | 0 | 10 |
|  | 37 | 20 | 2 | 109 | 13 | 181 |

Sensitivity 0.9487
Specificity 0.8450
PPV 0.6491
NPV 0.9820

TABLE 14

MCM2 and TOPOIIA

|  | TP | FP | FN | TN | Indeter. | Totals |
|---|---|---|---|---|---|---|
| NIL | 0 | 0 | 0 | 67 | 5 | 72 |
| ASC-US (No Lesion) | 0 | 1 | 0 | 23 | 2 | 26 |
| ASC-US (Lesion) | 0 | 0 | 0 | 0 | 0 | 0 |
| LSIL (No HSIL) | 0 | 8 | 4 | 18 | 12 | 42 |
| LSIL (HSIL) | 3 | 0 | 3 | 0 | 0 | 6 |
| HSIL | 25 | 0 | 0 | 0 | 0 | 25 |
| Cancer | 9 | 0 | 0 | 0 | 1 | 10 |
|  | 37 | 9 | 7 | 108 | 20 | 181 |

Sensitivity 0.8409
Specificity 0.9231
PPV 0.8043
NPV 0.9391

TABLE 15

MCM2 and Cyclin E

|  | TP | FP | FN | TN | Indeter. | Totals |
|---|---|---|---|---|---|---|
| NIL | 0 | 0 | 0 | 71 | 1 | 72 |
| ASC-US (No Lesion) | 0 | 0 | 0 | 25 | 1 | 26 |
| ASC-US (Lesion) | 0 | 0 | 0 | 0 | 0 | 0 |
| LSIL (No HSIL) | 0 | 9 | 0 | 27 | 6 | 42 |
| LSIL (HSIL) | 3 | 0 | 3 | 0 | 0 | 6 |
| HSIL | 24 | 0 | 1 | 0 | 0 | 25 |
| Cancer | 8 | 0 | 2 | 0 | 0 | 10 |
|  | 35 | 9 | 6 | 123 | 8 | 181 |

Sensitivity 0.8537
Specificity 0.9318
PPV 0.7955
NPV 0.9535

TABLE 16

MCM2 and p21waf1

|  | TP | FP | FN | TN | Indeter. | Totals |
|---|---|---|---|---|---|---|
| NIL | 0 | 2 | 0 | 60 | 10 | 72 |
| ASC-US (No Lesion) | 0 | 1 | 0 | 21 | 4 | 26 |
| ASC-US (Lesion) | 0 | 0 | 0 | 0 | 0 | 0 |
| LSIL (No HSIL) | 0 | 13 | 0 | 21 | 8 | 42 |
| LSIL (HSIL) | 3 | 0 | 3 | 0 | 0 | 6 |
| HSIL | 24 | 0 | 1 | 0 | 0 | 25 |
| Cancer | 9 | 0 | 1 | 0 | 0 | 10 |
|  | 36 | 16 | 5 | 102 | 22 | 181 |

Sensitivity 0.8780
Specificity 0.8644
PPV 0.6923
NPV 0.9533

TABLE 17

TOPO2A and Cyclin E

|  | TP | FP | FN | TN | Indeter. | Totals |
|---|---|---|---|---|---|---|
| NIL | 0 | 0 | 0 | 68 | 4 | 72 |
| ASC-US (No Lesion) | 0 | 1 | 0 | 24 | 1 | 26 |
| ASC-US (Lesion) | 0 | 0 | 0 | 0 | 0 | 0 |
| LSIL (No HSIL) | 0 | 5 | 0 | 27 | 10 | 42 |
| LSIL (HSIL) | 3 | 0 | 3 | 0 | 0 | 6 |
| HSIL | 22 | 0 | 1 | 0 | 2 | 25 |
| Cancer | 9 | 0 | 0 | 0 | 1 | 10 |
|  | 34 | 6 | 4 | 119 | 18 | 181 |

Sensitivity 0.8947
Specificity 0.9520
PPV 0.8500
NPV 0.9675

TABLE 18

TOPO2A and p21waf1

| | TP | FP | FN | TN | Indeter. | Totals |
|---|---|---|---|---|---|---|
| NIL | 0 | 2 | 0 | 58 | 12 | 72 |
| ASC-US (No Lesion) | 0 | 2 | 0 | 21 | 3 | 26 |
| ASC-US (Lesion) | 0 | 0 | 0 | 0 | 0 | 0 |
| LSIL (No HSIL) | 0 | 13 | 0 | 19 | 10 | 42 |
| LSIL (HSIL) | 3 | 0 | 3 | 0 | 0 | 6 |
| HSIL | 25 | 0 | 0 | 0 | 0 | 25 |
| Cancer | 10 | 0 | 0 | 0 | 0 | 10 |
| | 38 | 17 | 3 | 98 | 25 | 181 |

Sensitivity 0.9268
specificity 0.8522
PPV 0.6909
NPV 0.9703

TABLE 19 p21waf1 and Cyclin E

| | TP | FP | FN | TN | Indeter. | Totals |
|---|---|---|---|---|---|---|
| NIL | 0 | 2 | 0 | 61 | 9 | 72 |
| ASC-US (No Lesion) | 0 | 1 | 0 | 22 | 3 | 26 |
| ASC-US (Lesion) | 0 | 0 | 0 | 0 | 0 | 0 |
| LSIL (No HSIL) | 0 | 12 | 0 | 23 | 7 | 42 |
| LSIL (HSIL) | 3 | 0 | 3 | 0 | 0 | 6 |
| HSIL | 22 | 0 | 1 | 0 | 2 | 25 |
| Cancer | 8 | 0 | 1 | 0 | 1 | 10 |
| | 33 | 15 | 5 | 106 | 22 | 181 |

Sensitivity 0.8684
Specificity 0.8760
PPV 0.6875
NPV 0.9550

TABLE 20

MCM2, MCM6, and MCM7

| | TP | FP | FN | TN | Indeter. | Totals |
|---|---|---|---|---|---|---|
| NIL | 0 | 0 | 0 | 64 | 8 | 72 |
| ASC-US (No Lesion) | 0 | 3 | 0 | 20 | 3 | 26 |
| ASC-US (Lesion) | 0 | 0 | 0 | 0 | 0 | 0 |
| LSIL (No HSIL) | 0 | 17 | 0 | 21 | 4 | 42 |
| LSIL (HSIL) | 4 | 0 | 2 | 0 | 0 | 6 |
| HSIL | 24 | 0 | 0 | 0 | 1 | 25 |
| Cancer | 10 | 0 | 0 | 0 | 0 | 10 |
| | 38 | 20 | 2 | 105 | 16 | 181 |

Sensitivity 0.9500
Specificity 0.8400
PPV 0.6552
NPV 0.9813

TABLE 21

MCM2, MCM7, and TOPO2A

| | TP | FP | FN | TN | Indeter. | Totals |
|---|---|---|---|---|---|---|
| NIL | 0 | 0 | 0 | 63 | 9 | 72 |
| ASC-US (No Lesion) | 0 | 2 | 0 | 20 | 4 | 26 |
| ASC-US (Lesion) | 0 | 0 | 0 | 0 | 0 | 0 |
| LSIL (No HSIL) | 0 | 13 | 0 | 21 | 8 | 42 |
| LSIL (HSIL) | 4 | 0 | 2 | 0 | 0 | 6 |
| HSIL | 25 | 0 | 0 | 0 | 0 | 25 |
| Cancer | 10 | 0 | 0 | 0 | 0 | 10 |
| | 39 | 15 | 2 | 104 | 21 | 181 |

Sensitivity 0.9512
Specificity 0.8739
PPV 0.7222
NPV 0.9811

TABLE 22

MCM6, MCM7, and TOPO2A

| | TP | FP | FN | TN | Indeter. | Totals |
|---|---|---|---|---|---|---|
| NIL | 0 | 0 | 0 | 63 | 9 | 72 |
| ASC-US (No Lesion) | 0 | 3 | 0 | 21 | 2 | 26 |
| ASC-US (Lesion) | 0 | 0 | 0 | 0 | 0 | 0 |
| LSIL (No HSIL) | 0 | 16 | 0 | 20 | 6 | 42 |
| LSIL (HSIL) | 4 | 0 | 2 | 0 | 0 | 6 |
| HSIL | 25 | 0 | 0 | 0 | 0 | 25 |
| Cancer | 10 | 0 | 0 | 0 | 0 | 10 |
| | 39 | 19 | 2 | 104 | 17 | 181 |

Sensitivity 0.9512
Specificity 0.8455
PPV 0.6724
NPV 0.9811

TABLE 23

MCM6, MCM7, and Cyclin E

| | TP | FP | FN | TN | Indeter. | Totals |
|---|---|---|---|---|---|---|
| NIL | 0 | 0 | 0 | 65 | 7 | 72 |
| ASC-US (No Lesion) | 0 | 3 | 0 | 21 | 2 | 26 |
| ASC-US (Lesion) | 0 | 0 | 0 | 0 | 0 | 0 |
| LSIL (No HSIL) | 0 | 16 | 0 | 23 | 3 | 42 |
| LSIL (HSIL) | 4 | 0 | 2 | 0 | 0 | 6 |
| HSIL | 24 | 0 | 0 | 0 | 1 | 25 |
| Cancer | 10 | 0 | 0 | 0 | 0 | 10 |
| | 38 | 19 | 2 | 109 | 13 | 181 |

Sensitivity 0.9500
Specificity 0.8516
PPV 0.6667
NPV 0.9820

TABLE 24

MCM2, MCM7, and Cyclin E

| | TP | FP | FN | TN | Indeter. | Totals |
|---|---|---|---|---|---|---|
| NIL | 0 | 0 | 0 | 66 | 6 | 72 |
| ASC-US (No Lesion) | 0 | 2 | 0 | 20 | 4 | 26 |
| ASC-US (Lesion) | 0 | 0 | 0 | 0 | 0 | 0 |
| LSIL (No HSIL) | 0 | 13 | 0 | 25 | 4 | 42 |
| LSIL (HSIL) | 4 | 0 | 2 | 0 | 0 | 6 |
| HSIL | 24 | 0 | 1 | 0 | 0 | 25 |
| Cancer | 10 | 0 | 0 | 0 | 0 | 10 |
| | 38 | 15 | 3 | 111 | 14 | 181 |

Sensitivity 0.9268
Specificity 0.8810
PPV 0.7170
NPV 0.9737

TABLE 25

MCM2, MCM7, and p21waf1

|  | TP | FP | FN | TN | Indeter. | Totals |
|---|---|---|---|---|---|---|
| NIL | 0 | 2 | 0 | 56 | 14 | 72 |
| ASC-US (No Lesion) | 0 | 3 | 0 | 18 | 5 | 26 |
| ASC-US (Lesion) | 0 | 0 | 0 | 0 | 0 | 0 |
| LSIL (No HSIL) | 0 | 14 | 0 | 20 | 8 | 42 |
| LSIL (HSIL) | 4 | 0 | 2 | 0 | 0 | 6 |
| HSIL | 24 | 0 | 1 | 0 | 0 | 25 |
| Cancer | 10 | 0 | 0 | 0 | 0 | 10 |
|  | 38 | 19 | 3 | 94 | 27 | 181 |

Sensitivity 0.9268
Specificity 0.8319
PPV 0.6667
NPV 0.9691

TABLE 26

MCM2, TOPOIIA and Cyclin E

|  | TP | FP | FN | TN | Indeter. | Totals |
|---|---|---|---|---|---|---|
| NIL | 0 | 0 | 0 | 67 | 5 | 72 |
| ASC-US (No Lesion) | 0 | 1 | 0 | 23 | 2 | 26 |
| ASC-US (Lesion) | 0 | 0 | 0 | 0 | 0 | 0 |
| LSIL (No HSIL) | 0 | 9 | 0 | 22 | 11 | 42 |
| LSIL (HSIL) | 3 | 0 | 3 | 0 | 0 | 6 |
| HSIL | 25 | 0 | 0 | 0 | 0 | 25 |
| Cancer | 9 | 0 | 0 | 0 | 1 | 10 |
|  | 37 | 10 | 3 | 112 | 19 | 181 |

Sensitivity 0.9250
Specificity 0.9180
PPV 0.7872
NPV 0.9739

TABLE 27

MCM2, Cyclin E and p21waf1

|  | TP | FP | FN | TN | Indeter. | Totals |
|---|---|---|---|---|---|---|
| NIL | 0 | 2 | 0 | 60 | 10 | 72 |
| ASC-US (No Lesion) | 0 | 1 | 0 | 21 | 4 | 26 |
| ASC-US (Lesion) | 0 | 0 | 0 | 0 | 0 | 0 |
| LSIL (No HSIL) | 0 | 13 | 0 | 21 | 8 | 42 |
| LSIL (HSIL) | 3 | 0 | 3 | 0 | 0 | 6 |
| HSIL | 24 | 0 | 1 | 0 | 0 | 25 |
| Cancer | 9 | 0 | 1 | 0 | 0 | 10 |
|  | 36 | 16 | 5 | 102 | 22 | 181 |

Sensitivity 0.8780
Specificity 0.8644
PPV 0.6923
NPV 0.9533

TABLE 28

MCM2, TOPOIIA and p21waf1

|  | TP | FP | FN | TN | Indeter. | Totals |
|---|---|---|---|---|---|---|
| NIL | 0 | 2 | 0 | 57 | 13 | 72 |
| ASC-US (No Lesion) | 0 | 2 | 0 | 20 | 4 | 26 |
| ASC-US (Lesion) | 0 | 0 | 0 | 0 | 0 | 0 |
| LSIL (No HSIL) | 0 | 13 | 0 | 18 | 11 | 42 |
| LSIL (HSIL) | 3 | 0 | 3 | 0 | 0 | 6 |
| HSIL | 25 | 0 | 0 | 0 | 0 | 25 |
| Cancer | 10 | 0 | 0 | 0 | 0 | 10 |
|  | 38 | 17 | 3 | 95 | 28 | 181 |

Sensitivity 0.9268
Specificity 0.8482
PPV 0.6909
NPV 0.9694

TABLE 29

MCM7, TOPO2A, and Cyclin E

|  | TP | FP | FN | TN | Indeter. | Totals |
|---|---|---|---|---|---|---|
| NIL | 0 | 0 | 0 | 64 | 8 | 72 |
| ASC-US (No Lesion) | 0 | 2 | 0 | 21 | 3 | 26 |
| ASC-US (Lesion) | 0 | 0 | 0 | 0 | 0 | 0 |
| LSIL (No HSIL) | 0 | 12 | 0 | 23 | 7 | 42 |
| LSIL (HSIL) | 4 | 0 | 2 | 0 | 0 | 6 |
| HSIL | 25 | 0 | 0 | 0 | 0 | 25 |
| Cancer | 10 | 0 | 0 | 0 | 0 | 10 |
|  | 39 | 14 | 2 | 108 | 18 | 181 |

Sensitivity 0.9512
Specificity 0.8852
PPV 0.7358
NPV 0.9818

TABLE 30

MCM7, p21waf1, and Cyclin E

|  | TP | FP | FN | TN | Indeter. | Totals |
|---|---|---|---|---|---|---|
| NIL | 0 | 2 | 0 | 57 | 13 | 72 |
| ASC-US (No Lesion) | 0 | 3 | 0 | 19 | 4 | 26 |
| ASC-US (Lesion) | 0 | 0 | 0 | 0 | 0 | 0 |
| LSIL (No HSIL) | 0 | 14 | 0 | 21 | 7 | 42 |
| LSIL (HSIL) | 4 | 0 | 2 | 0 | 0 | 6 |
| HSIL | 24 | 0 | 1 | 0 | 0 | 25 |
| Cancer | 10 | 0 | 0 | 0 | 0 | 10 |
|  | 38 | 19 | 3 | 97 | 24 | 181 |

Sensitivity 0.9268
Specificity 0.8362
PPV 0.6667
NPV 0.9700

TABLE 31

MCM7, p21waf1, and TOPO2A

|  | TP | FP | FN | TN | Indeter. | Totals |
|---|---|---|---|---|---|---|
| NIL | 0 | 2 | 0 | 54 | 16 | 72 |
| ASC-US (No Lesion) | 0 | 3 | 0 | 19 | 4 | 26 |
| ASC-US (Lesion) | 0 | 0 | 0 | 0 | 0 | 0 |
| LSIL (No HSIL) | 0 | 14 | 0 | 18 | 10 | 42 |
| LSIL (HSIL) | 4 | 0 | 2 | 0 | 0 | 6 |
| HSIL | 25 | 0 | 0 | 0 | 0 | 25 |
| Cancer | 10 | 0 | 0 | 0 | 0 | 10 |
|  | 39 | 19 | 2 | 91 | 30 | 181 |

Sensitivity 0.9512
Specificity 0.8273
PPV 0.6724
NPV 0.9785

TABLE 32

MCM2, MCM7, Cyclin E, and p21waf1

|  | TP | FP | FN | TN | Indeter. | Totals |
|---|---|---|---|---|---|---|
| NIL | 0 | 2 | 0 | 56 | 14 | 72 |
| ASC-US (No Lesion) | 0 | 3 | 0 | 18 | 5 | 26 |
| ASC-US (Lesion) | 0 | 0 | 0 | 0 | 0 | 0 |
| LSIL (No HSIL) | 0 | 14 | 0 | 20 | 8 | 42 |
| LSIL (HSIL) | 4 | 0 | 2 | 0 | 0 | 6 |
| HSIL | 24 | 0 | 1 | 0 | 0 | 25 |
| Cancer | 10 | 0 | 0 | 0 | 0 | 10 |
|  | 38 | 19 | 3 | 94 | 27 | 181 |

Sensitivity 0.9268
Specificity 0.8319
PPV 0.6667
NPV 0.9691

TABLE 33

MCM2, MCM7, Cyclin E and TOPOIIA

|  | TP | FP | FN | TN | Indeter. | Totals |
|---|---|---|---|---|---|---|
| NIL | 0 | 0 | 0 | 63 | 9 | 72 |
| ASC-US (No Lesion) | 0 | 2 | 0 | 20 | 4 | 26 |
| ASC-US (Lesion) | 0 | 0 | 0 | 0 | 0 | 0 |
| LSIL (No HSIL) | 0 | 13 | 0 | 21 | 8 | 42 |
| LSIL (HSIL) | 4 | 0 | 2 | 0 | 0 | 6 |
| HSIL | 25 | 0 | 0 | 0 | 0 | 25 |
| Cancer | 10 | 0 | 0 | 0 | 0 | 10 |
|  | 39 | 15 | 2 | 104 | 21 | 181 |

Sensitivity 0.9512
Specificity 0.8739
PPV 0.7222
NPV 0.9811

TABLE 34

MCM2, MCM7, Cyclin E, p21waf1, and TOPO2A

|  | TP | FP | FN | TN | Indeter. | Totals |
|---|---|---|---|---|---|---|
| NIL | 0 | 2 | 0 | 53 | 17 | 72 |
| ASC-US (No Lesion) | 0 | 3 | 0 | 18 | 5 | 26 |
| ASC-US (Lesion) | 0 | 0 | 0 | 0 | 0 | 0 |
| LSIL (No HSIL) | 0 | 14 | 0 | 18 | 10 | 42 |
| LSIL (HSIL) | 4 | 0 | 2 | 0 | 0 | 6 |
| HSIL | 25 | 0 | 0 | 0 | 0 | 25 |
| Cancer | 10 | 0 | 0 | 0 | 0 | 10 |
|  | 39 | 19 | 2 | 89 | 32 | 181 |

Sensitivity 0.9512
Specificity 0.8241
PPV 0.6724
NPV 0.9780

TABLE 35

MCM2, MCM6, MCM7, TOPO2A, Cyclin E, and p21waf1

|  | TP | FP | FN | TN | Indeter. | Totals |
|---|---|---|---|---|---|---|
| NIL | 0 | 2 | 0 | 52 | 18 | 72 |
| ASC-US (No Lesion) | 0 | 4 | 0 | 18 | 4 | 26 |
| ASC-US (Lesion) | 0 | 0 | 0 | 0 | 0 | 0 |
| LSIL (No HSIL) | 0 | 18 | 0 | 16 | 8 | 42 |
| LSIL (HSIL) | 4 | 0 | 2 | 0 | 0 | 6 |
| HSIL | 25 | 0 | 0 | 0 | 0 | 25 |

TABLE 35-continued

MCM2, MCM6, MCM7, TOPO2A, Cyclin E, and p21waf1

|  | TP | FP | FN | TN | Indeter. | Totals |
|---|---|---|---|---|---|---|
| Cancer | 10 | 0 | 0 | 0 | 0 | 10 |
|  | 39 | 24 | 2 | 86 | 30 | 181 |

Sensitivity 0.9512
Specificity 0.7818
PPV 0.6190
NPV 0.9773

Data was compiled on 28 antibody cocktails, as described above. Biomarker expression was analyzed using cocktails comprising antibodies directed to 2, 3, 4, 5 or even all 6 of the biomarkers of interest. Twenty-one of the 28 antibody cocktails showed sensitivities greater than 92%. Four of the 28 cocktails produced specificities above 90% with the lowest value at 78%. The highest values were achieved with a combination of MCM2, TOPOIIA and Cyclin E. This cocktail yielded a sensitivity of 93% along with a specificity of 92%. It appears that a combination of at least 3 biomarkers should yield a sensitivity greater than 90%. It is recognized that adjustments to the assay would further increase the sensitivity and specificity of the assay.

Example 4

Detection of Biomarker Expression Using Antibody Cocktails

Antibody cocktails were prepared using various combinations of antibodies directed to Cyclin E, MCM2, MCM6, MCM7, p21waf1, and TOPO2a. The composition of each cocktail is listed in the table below.

TABLE 36

Composition of Antibody Cocktails

| Cocktail ID | Biomarkers |
|---|---|
| Cocktail 1 | Cyclin E, MCM2, MCM7 |
| Cocktail 2 | Cyclin E, MCM6, MCM7 |
| Cocktail 3 | Cyclin E, MCM7, p21waf1 |
| Cocktail 4 | Cyclin E, MCM7, TOPO2a |
| Cocktail 5 | MCM2, MCM7, p21waf1 |
| Cocktail 6 | MCM6, MCM7, p21waf1 |
| Cocktail 7 | MCM7, p21waf1, TOPO2a |
| Cocktail 8 | MCM2, MCM7, TOPO2a |
| Cocktail 9 | MCM6, MCM7, TOPO2a |
| Cocktail 10 | MCM2, MCM6, MCM7 |
| Cocktail 11 | Cyclin E, MCM2, MCM6, MCM7, p21waf1, TOPO2a |
| Cocktail 12 | Cyclin E, MCM2, MCM7, p21waf1 |
| Cocktail 13 | MCM2 and MCM 7 |
| Cocktail 14 | MCM7 and p21waf1 |
| Cocktail 15 | MCM7 and Cyclin E |
| Cocktail 16 | MCM2 and p21waf1 |
| Cocktail 17 | Cyclin E and p21waf1 |
| Cocktail 18 | MCM2 and Cyclin E |
| Cocktail 19 | MCM7 and TOPO2a |
| Cocktail 20 | MCM2 and TOPO2a |
| Cocktail 21 | Cyclin E and TOPO2a |
| Cocktail 22 | p21waf1 and TOPO2a |

Two sets of cervical cytology specimens were prepared by pooling HSIL cases (HSIL pool) and NIL cases (NIL pool). Each antibody cocktail was then tested on the HSIL pool and the NIL pool. Biomarker antibodies were also tested individually as a control. Slide preparation and automated immunocytochemistry were performed as described in Example 2.

Slides were screened and reviewed by a cytotechnologist and a pathologist. Specific staining of cells indicative of high-grade cervical disease, staining of glandular cells, bacteria cross-reactivity, and the location of cell staining were all variables that were recorded during the screening process.

The immunocytochemistry results indicated an increase in staining of cells indicative of high-grade cervical disease in the HSIL pool with the biomarker antibody cocktails when compared to the results obtained with detection of a single biomarker. Additionally, there was no significant increase in background when the number of antibodies in the cocktails increased from 2 to 3, 4 or 6. Furthermore, the various antibody cocktails did not show an increase in background staining when tested on the NIL pool.

Example 5

Detection of Biomarker Overexpression in Cervical Samples Using Immunocytochemistry Slide Preparation and Pretreatment Patient cervical samples were collected as described above in Example 1. Slides comprising a monolayer of cervical cells were prepared by the AutoPrep® System using "prep only" mode. Prepared slides were immediately placed in 1× SureSlide® Pretreatment Buffer (0.5% sodium laureth-13-carboxylate (Sandopan LS) in deionized $H_2O$) for a minimum of 1 hour and a maximum of 72 hours. The pretreated slides were placed in a steamer at 95° C. for 45 minutes without preheating. Slides were removed from the steamer, allowed to cool at room temperature for 20 minutes, and then rinsed well in deionized water. Slides were rinsed in TBST (TBS/Tween-20) twice at 2 minutes per rinse. The slides were tapped to remove excess buffer and placed into a humid chamber. Slides were subjected to manual or automated immunocytochemistry, as described below.

Manual Immunocytochemistry

200 μl of peroxidase block reagent (0.03% hydrogen peroxide) was applied to each slide to cover the cell deposition area for a period of 5 minutes. The slides were then rinsed with TBST three times at 2 minutes per rinse. Excess buffer was removed, and the slides were placed into a humid chamber. 200 μl of protein block reagent (purified casein and surfactant) was applied to each slide and incubated for 5 minutes. After the excess protein block reagent was removed, the slides were placed in a humid chamber.

200 μl of primary monoclonal antibody cocktail comprising two mouse anti-human antibodies directed to MCM2 (clone 27C5.6 at 0.39 mg/ml, 1:800 dilution; clone 26H6.19 at 0.918 mg/ml, 1:10,000 dilution) and a third mouse anti-human antibody specific for Topo2A (clone SWT3D1 at 100 μg/ml, 1:10,000 dilution) was applied to each slide to completely cover the cell deposition area. Slides were incubated for 30 minutes and then rinsed with TBST three times at 2 minutes per rinse. Excess buffer was removed, and the slides were returned to the humid chamber. 200 μl of mouse probe reagent that binds to mouse monoclonal antibodies was applied as above for 20 minutes. The slides were rinsed with TBST three times at 2 minutes per rinse. Excess buffer was removed, and the slides were again placed into the humid chamber.

200 μl of polymer reagent comprising a dextran polymer conjugated with HRP and a secondary goat anti-mouse antibody that binds to the mouse probe reagent was applied as above for 20 minutes and then the slides rinsed with TBST 3 times at 2 minutes per rinse. After the excess buffer was removed, the slides were returned to the humid chamber. 200 μl of DAB substrate-chromgen solution was applied as above for 5 minutes. The slides were rinsed with deionized water for 5 minutes and then rinsed with TBST for 2 minutes with one change of buffer. Excess buffer was removed and the slides were placed in a humid chamber as before. 200 μl of hematoxylin was added for 1 minute, followed by 3 rinses with deionized water at 2 minutes per rinse. Excess deionized water was removed, and the slides were placed into the humid chamber. 200 μl of bluing agent (i.e., TBS, pH 7.4 with tween-20 and sodium azide) was applied to each slide for 1 minute. The slides were then rinsed in one change of TBST and 1 change of deionized water for 2 minutes each. The slides were then dehydrated, cleared, coverslipped, and analyzed as described in Examples 1 and 2.

Automated Immunocytochemistry

The autostainer was programmed according to manufacturer's instructions to include the following sequence of steps:

a. 2 buffer rinses (TBST)
b. 5 min peroxidase block
c. 2 buffer rinses (TBST)
d. 5 min protein block, blow
e. 30 min primary antibody cocktail incubation
f. 3 buffer rinses (TBST)
g. 20 min mouse probe reagent
h. 3 buffer rinses (TBST)
i. 20 min polymer-HRP
j. 3 buffer rinses (TBST)
k. 5 min DAB (1 drop of chromagen to 1 ml of buffer)
l. 3$H_2O$ rinses
m. 2 buffer rinses (TBST)
n. 1 min Mayer's hematoxylin
o. 3$H_2O$ rinses
p. 1 min bluing agent
q. 1 buffer rinse (TBST)
r. 1$H_2O$ rinse The necessary staining and counterstaining reagents were loaded onto the machine. The prepared and pretreated slides were loaded onto the autostainer, and the above program was run. At the end of the run, the slides were removed and rinsed briefly in tap water. The slides were dehydrated, cleared, coverslipped, and analyzed as described in Examples 1 and 2.

Results

TABLE 37

| NIL Cases (n = 45) | | |
| --- | --- | --- |
| Pap Result | | |
| NIL | Other | Unsatisfactory |
| 44 | 1 (ASC-US) | 0 |
| ICC Result | | |
| Positive | Negative | Unsatisfactory |
| 0 | 44 | 1 |

TABLE 38

HSIL Cases (n = 45)

Pap Result

| HSIL | Other | Unsatisfactory |
|---|---|---|
| 45 | 0 | 0 |

ICC Result

| Positive | Negative | Unsatisfactory |
|---|---|---|
| 45 | 0 | 0 |

Of the 45 NIL cases tested, a review of the Pap stained slides revealed one ASC-US case. The immunocytochemistry (ICC) results for the NIL samples were negative, with one case deemed unsatisfactory for evaluation. Regarding the HSIL cases, each of the 45 cases was confirmed to be high-grade cervical disease based upon the review of the Pap stained slides. Additionally, each of the 45 HSIL cases was also positive in the ICC assay. The negative control, i.e., a universal mouse IgG control applied to the SiHa cell line control, produced negative results in the ICC assay. The positive control, i.e., the primary antibody cocktail applied to the SiHa cell line control, produced positive results in the ICC assay.

Example 6

Combined Immunocytochemistry and Pap Staining Procedure

Patient cervical samples were collected as described above in Example 1. Slides comprising a monolayer of cervical cells were prepared and pretreated as indicated in Example 5. Each pretreated slide was subjected to automated immunocytochemistry and Pap staining, thereby permitting visualization of both biomarker overexpression and cell morphology on a single slide.

Automated Immunocytochemistry

Automated immunocytochemistry was performed on each slide as described above in Example 5. At the end of the staining program, the slides were removed from the autostainer and rinsed in tap water for 3-5 minutes. Each slide was then stained according to conventional Pap staining methods, as described below.

Pap Staining Method

Following automated immunocytochemistry, each slide was further stained with Pap stain. The slides were first rinsed in 95% ethanol for 30 seconds. EA50 and Orange G were applied to half of the slides for 3 minutes and to the remaining slides for 6 minutes. All of the slides were then rinsed 2 times in 95% ethanol, 3 times in 100% ethanol, and 3 times in xylene for 30 seconds per rinse. The slides were then cover-slipped with permanent mounting media and analyzed as described above in Examples 1 and 2.

Results

A panel of 5 NIL and 5 HSIL cases were each subjected to 3 minutes or 6 minutes of staining with EA50 and Orange G in the Pap staining method. Results indicated minimal difference between the 3 minute and the 6 minute staining protocols. The slides subjected to 3 minutes of Pap staining displayed slightly less intense staining. Furthermore, the ICC positive staining HSIL cells were readily observed with the Pap counterstain.

Example 7

Combined Immunocytochemistry and Pap Staining Procedure (Optimization of Pap Staining)

The combined immunocytochemistry and Pap staining procedure outlined in Example 6 was modified to optimize the Pap staining parameters in order to maximize the contrast between the chromogen (i.e., DAB) staining of the immunocytochemistry method and the level of Pap staining.

Slides were prepared, pretreated, and subjected to automated immunocytochemistry as described above in Example 6. The slides were then stained with a conventional Pap stain essentially as described in Example 6, with the following modifications. Hematoxylin was tested using the Harris formulation along with Myers formulation. EA/Orange G was applied for 3 minutes or 6 minutes. Additionally, there were 3 changes of 95% ethanol after the EA/Orange G addition.

Slides received a determination of positive, negative, or unsatisfactory based upon the immunocytochemistry staining. Additionally, slides were evaluated morphologically for comparison with the incoming Pap diagnosis.

Results

TABLE 39

Results of Combined Immunocytochemistry and Pap Staining Method

| Incoming Pap Diagnosis | ICC Results | Comments |
|---|---|---|
| NIL n = 7 | Negative | All cases confirmed as NIL. |
| LSIL n = 6 | Negative | 5 of the 6 LSIL cases did not have LSIL cells on the slides. These cases were either NIL or ASC-US. |
| HSIL n = 6 | Positive | All cases confirmed as HSIL. |
| Cancer n = 4 | Positive | All cases were squamous cell carcinoma. |

The combined ICC and Pap staining procedure permitted both morphological analysis and assessment of biomarker overexpression. Additional experimentation will be required to further optimize the method.

Example 8

Immunocytochemistry Kit for the Detection of Biomarker Overexpression in Cervical Samples I. Principles of the Procedure An immunocytochenical test kit contains reagents required to complete a three-step immunocytochemical staining procedure for routinely prepared monolayer cervical specimens. Following incubation with the monoclonal antibody cocktail, this kit employs a ready-to-use visualization reagent based on dextran technology. This reagent consists of a secondary goat anti-mouse antibody molecule and horseradish peroxidase molecules linked to a dextran polymer backbone. The enzymatic conversion of the subsequently added chromogen results in the formation of a visible reaction product at the antigen(s) site. The specimen is then counterstained with hematoxylin, a bluing agent is applied, and the slide is coverslipped. Results are interpreted using a light microscope. A positive result indicative of cervical high-grade is achieved when cells of interest are stained brown.

A gallery of potentially positive cells may be created using automated imaging equipment. The gallery then can be reviewed to determine a positive result or negative result.

The immunocytochemical test kit is applicable for both manual and automated staining.

II. Reagents Provided

The following materials, sufficient for 75 monolayer preparations using 200 μL of the ready-to-use mouse monoclonal cocktail per preparation, were included in the immunocytochemical test kit:

TABLE 40

Immunocytochemistry Kit Components

| Vial No. | Quantity | Description |
| --- | --- | --- |
| 1a | 1 × 15 mL | Peroxidase-Blocking Reagent: Buffered hydrogen peroxide plus stabilizer and proprietary components |
| 1b | 1 × 15 mL | Protein Blocking Reagent: Purified casein plus proprietary combination of proteins in modified PBS with preservative and surfactant |
| 2 | 1 × 15 mL | Mouse Anti-Human Antibody Cocktail: Ready-to-use monoclonal antibody cocktail supplied in TRIS buffered solution with Tween 20, pH 7.4. Contains 0.39 mg/mL MCM2 mAb clone 27C5.6 (1:800 dilution), 0.918 mg/mL MCM2 mAb clone 26H6.19 (1:10,000 dilution), 100 μg/mL Topo2a mAb clone SWT3D1 (1:10,000 dilution), stabilizing proteins and anti-microbial agent. |
| 3a | 1 × 15 mL | Mouse Probe Reagent: Binds to mouse monoclonal antibodies |
| 3b | 1 × 15 mL | Polymer Reagent: Polymer conjugated with horseradish peroxidase that binds to Mouse Probe Reagent |
| 4a | 1 × 18 mL | DAB Substrate Buffer: Substrate buffer used in the preparation of the DAB Chromogen |
| 4b | 1 × 1 mL | DAB Chromogen: 3,3'-diaminobenzidine chromogen solution |
| 5 | 1 × 18 mL | Hematoxylin Counterstain: aqueous based Mayers Hematoxylin |
| 6 | 1 × 18 mL | Bluing Agent: Tris buffered saline, pH 7.4 with Tween 20 and 0.09% NaN$_3$ |

The following materials and reagents were required to perform the Immunocytochemistry methods but were not supplied in the kit:

Absorbent Wipes
SiHa Cell Line (TriPath Imaging, Inc.)
Deionized or Distilled Water
Ethanol (95% and 100)
Glass Coverslips
Gloves
Humid Chamber
Light Microscope (10×, 20×, 40× objectives)
Mounting Media
Pipettes and Pipette Tips (capable of delivering 20 μl, 200 μl and 1000 μl volumes)
SureSlide Preparation Buffer (TriPath Imaging, Inc.)—Pretreatment Buffer (0.5% sodium laureth-13-carboxylate (Sandopan LS) in deionized H$_2$0)
Staining Jars or Baths
Timer (capable of 1-60 minute intervals)
Tris Buffered Saline (TBS)
Tween 20
Universal Mouse IgG Negative Control
Vortexer
Xylene or Xylene Substitutes
Steamer/waterbath III. Instructions for Use Specimen Preparation The following steps were followed for the preparation of cervical samples:

Consult the Operator's Manual for the SurePath PrepStain System™ for the preparation of slides from residual specimens.

Add 8 mL of SurePath™ preservative fluid to the residual sample in the SurePath™ vial (approx. 2 mLs). The diluted sample is processed on the PrepMate™ using the standard technique and on the PrepStain™ using the GYN version 1.1, Slide Preparation.

Prepared slides are immediately placed into the pretreatment buffer for a minimum of 1 hour with a maximum of 72 hours prior to immunostaining.

Epitope retrieval must be used for optimal kit performance. This procedure involves soaking prepared slides in the pretreatment buffer for a minimum of 1 hour at room temperature followed by heating slides in the pretreatment buffer to 95° C. Slides are held at 95° C. for 15 minutes and allowed to cool down at room temperature for 20 minutes. The use of a calibrated waterbath or vegetable steamer capable of maintaining the required temperature is recommended. Laboratories located at higher elevations should determine the best method of maintaining the required temperature. The staining procedure is initiated immediately following epitope retrieval and cool down. Deviations from the described procedure may affect results.

Reagent Preparation

The following reagents were prepared prior to staining:

Tris Buffered Saline with 0.05% Tween 20 (TBST)

Prepare TBS according to manufacturer's specifications.
Add Tween 20 to a final concentration of 0.05%.
Store at room temperature if used within one week.
Unused solution may be stored at 2-8° C. for 3 months.
Solution is clear and colorless. Discard diluted solution if cloudy in appearance.

Substrate-Chromogen Solution (DAB) (Volume Sufficient for 5 Slides)

Transfer 1 mL of DAB Buffered Substrate to a test tube.
Add one drop (20-30 uL) of DAB+ Chromogen. Mix thoroughly and apply to slides with a pipette.
Prepare Substrate-Chromogen solution fresh daily.
Any precipitate developing in the solution does not affect staining quality.

IV. Staining Protocol (Performed at Room Temperature, 20-25° C.)

The following steps were performed for immunostaining of the cervical cytology samples:

Staining Procedural Notes

The user should read these instructions carefully and become familiar with all components prior to use.
All reagents are equilibrated to room temperature (20-25° C.) prior to immunostaining. All incubations are performed at room temperature.
Do not allow slides to dry out during the staining procedure. Dried cellular preparations may display increased non-specific staining. Cover slides exposed to drafts. Slides should be placed in a humid chamber for prolonged incubations.

Epitope Retrieval
    Place the prepared slides in the pretreatment buffer for a minimum of 1 hour to a maximum of 72 hours.
    Incubate for 15 minutes at 95° C.
    Remove the entire coplin jar with slides from the waterbath or steamer and allow slides to cool in the buffer for 20 minutes.
    Rinse the slides with diH2O and transfer to a TBST bath.

Peroxidase Blocking
    Tap off excess buffer.
    Load slides into prepared humidity chamber (filled with water moistened paper towels or gauze).
    Apply 200 µL Peroxidase Block reagent to cover the cell deposition area.
    Incubate 5 minutes (±1 minute).
    Rinse slides in TBST, 3 changes, 2 minutes each.

Protein Block
    Tap off excess buffer.
    Load the slides into the prepared humidity chamber (filled with water moistened paper towels or gauze).
    Apply 200 µL of Protein Block to completely cover cell deposition area.
    Incubate 5 minutes (±1 minute).
    Do not rinse slides.

Primary Antibody Cocktail
    Tap off excess Protein Block.
    Load the slides into the prepared humidity chamber (filled with water moistened paper towels or gauze).
    Apply 200 µL primary antibody cocktail (to completely cover cell deposition area.
    Incubate 30 minutes at room temperature.
    Rinse each slide individually with TBST using a wash bottle (do not focus the flow directly on the cell deposition area). Load slides into a slide rack.
    Rinse slides in TBST, 3 changes, 2 minutes each.

Detection Chemistry
    Tap off excess buffer.
    Load slides into prepared humidity chamber (filled with water moistened paper towels or gauze).
    Apply 200 µL Mouse Probe to completely cover cell deposition area.
    Incubate 20 minutes (±1 minute).
    Rinse slides in TBST, 3 changes, 2 minutes each.
    Tap off excess buffer.
    Load slides into prepared humidity chamber (filled with water moistened paper towels or gauze).
    Apply 200 µL of Polymer to cover cell deposition area.
    Incubate for 20 minutes (±1 minute).
    Rinse slides in TBST bath, 3 changes, 2 minutes each.
    Tap off excess buffer.
    Load the slides into the prepared humidity chamber (filled with water moistened paper towels or gauze).
    Apply 200 µL of DAB working solution to completely cover cell deposition area.
    Incubate for 5 minutes (±1 minute).
    Rinse slides for 5 minutes in diH2O for 5 minutes.

Counterstain
    Rinse slides in TBST, 1 change for 2 minutes.
    Load slides into prepared humidity chamber (filled with water moistened paper towels or gauze).
    Apply 200 µL of hematoxylin to completely cover cell deposition area.
    Incubate for 1 minute (±10 seconds).
    Rinse slides for 3 minutes in running H2O.
    Load slides into prepared humidity chamber (filled with water moistened paper towels or gauze).
    Blue slides by applying 200 µL Bluing Agent for 1 minute (±10 seconds).
    Repeat running water rinse for 1 minute.

Mounting
    Immerse slides in 95% ethanol, 1 minute or 25 dips.
    Immerse slides in absolute alcohol, 4 changes, 1 minute each or 25 dips.
    Clear with xylene, 3 changes, 1 minute each or 25 dips.
    Coverslip slides with non-aqueous, permanent mounting media using glass coverslips.

V. Quality Control

The following quality control issues were considered when using the immunocytochemistry kit described in this example:

Variability in results is often derived from differences in specimen handling and changes in test procedures. Consult the proposed quality control guidelines of the NCCLS Quality Assurance for Immunocytochemistry for additional information.

Control Cell Line is available from TriPath Imaging, Inc. Each vial contains a cervical cancer cell line, which is processed in a similar manner as the clinical specimens. Two slides should be stained in each staining procedure. The evaluation of the control slide cell line indicates the validity of the staining run.

VI. Interpretation of Staining

Control Slides:

The control slide stained with the immunocytochemical test kit were examined first to ascertain that all reagents functioned properly. The presence of a brown (3,3'-diaminobenzidine tetrahydrochloride, DAB) reaction product in the nuclei of the cells were indicative of positive reactivity.

Patient Specimens:

Slide evaluation was performed by a cytotechnologist or pathologist using a light microscope. Cells were reviewed manually or electronically stored in an image gallery derived from a light microscope.

Approximately 1610 cervical samples representing various diagnoses were collected. The following table indicates the number of samples analyzed using the immunocytochemistry kit within each diagnosis group, as determined by conventional Pap staining or biopsy.

TABLE 41

Patient Specimens within Each Diagnosis Group (Pap Staining)

| Cytology Results | Number | % |
| --- | --- | --- |
| NIL | 671 | 41.7% |
| LSIL | 395 | 24.53% |
| ASCUS | 349 | 21.68% |
| HSIL | 150 | 9.32% |
| ASC-H | 38 | 2.36% |
| AGUS | 6 | 0.37% |
| SCC | 1 | 0.06% |
| Total | 1610 | |

TABLE 42

Patient Specimens within Each Diagnosis Group (Biopsy)

| Biopsy Results | Number | % |
|---|---|---|
| NIL | 968 | 60.20% |
| CIN1 | 369 | 22.95% |
| CIN2 | 140 | 8.71% |
| CIN3 | 131 | 8.15% |
| Missing | 2 | |
| Total | 1610 | |

Slide Scoring Guide

The following procedure was followed for the scoring of all slides analyzed by the immunocytochemistry methods described in this example:

Step 1: Is it an Adequate Specimen?

The Bethesda System for Reporting Cervical Cytology (second edition) states, "An adequate liquid-based preparation should have an estimated minimum of at least 5000 well-visualized/well-preserved squamous cells." These same criteria were applied when evaluating all of the slides. However, as with a routine Pap preparation, any specimen with abnormal cells, which are exhibiting a positive molecular reaction, was, by definition, satisfactory for evaluation. If the answer to this step was "yes", the cytotechnologist proceeded to the next step; if the answer was "no," the result was Unsatisfactory for Evaluation.

Step 2: Is there Moderate to Intense Brown Nuclear Staining in Epithelial Cells?

The detection chemicals used in the immunocytochemistry kit of this example (e.g., SureDetect Detection Chemistry Kit) stains dysplastic nuclei associated with ≧CIN 2 with a brown chromagen, DAB. To answer "yes" to this step, samples were analyzed for brown staining that was easily visualized. If just a faint amount, or "blush," of brown was seen, this was not enough to warrant a rendering of positive. If no brown nuclear stain was seen, this was deemed a negative test result. If there was adequate brown stain, the analysis proceeded to the next step.

Step 3: Is this a Squamous (or Glandular) Cell with Brown Nuclear Staining and is the Cell≧ASC (AGC)?

Using the same morphological criteria outlined in The Bethesda System for Reporting Cervical Cytology (2nd Ed.) ("TBS"), it was determined if the squamous cell containing the brown nucleus was ≧ASC (atypical squamous cells). This would include ASC-US, ASC-H, LSIL, HSIL, and cancer. If the cell was glandular in appearance, the TBS criteria for determining if a cell is ≧AGC (atypical glandular cells) applied. This would include endocervical AGC, endometrial AGC, AIS, and adenocarcinoma. If the cell was considered to be ≧ASC (or ≧AGC) than this would result in a positive test result. If the cells in question were consistent with NILM (negative for intraepithelial lesion or malignancy) this would be a negative test result.

VII. Results 27 cases that were originally classified as NIL by conventional Pap staining methods stained positive in the immunocytochemistry test. Of these 27 cases, 7 were classified as HSIL, 10 as ASC-H, 3 as ASC-US, and 3 as indeterminate upon review by aboard certified pathologist. The 7 HSIL cases are considered high-grade cervical disease. These 27 cases were identified by positive immunostaining in the immocytochemistry assay, thereby indicating the value of the methods disclosed herein for identifying patients misclassified as NIL by Pap staining.

Biopsy results were not obtained for all NIL specimens. Estimates of sensitivity and positive predictive value (PPV) for the immunocytochemistry method described in this example were calculated based on comparison with the "gold standard" biopsy results. Single biopsy has limitations as a gold standard. PPV for the ICC assay will improve by serial monitoring of the patient or utilizing a more aggressive surgical endpoint such as loop electrosurgical excision procedure or cone biopsy. Single biopsy is known to have a false negative result for disease of at least 31%. See Elit et al. (2004) *J. Lower Genital Tract Disease* 8(3):181-187.

TABLE 43

Estimated sensitivity and positive predictive value of ICC test based on the biopsy results

| | ASC-H | ASCUS | LSIL | HSIL | ≧ASCUS |
|---|---|---|---|---|---|
| Sensitivity | 76.5% | 92.6% | 97.7% | 98.5% | 96.2% |
| | (52.7%, | (76.6%, | (92.1%, | (94.6%, | (93.1%, |
| | 90.4%)* | 97.9%) | 99.4%) | 99.6%) | 97.9%) |
| PPV | 59.1% | 26.0% | 31.0% | 90.1% | 46.9% |
| | (38.7%, | (18.3%, | (25.9%, | (84.1%, | (42.8%, |
| | 76.7%) | 35.6%) | 36.7%) | 94.0%) | 51.2%) |

*(95% confidence interval)

The sensitivity and PPV of the immunocytochemistry method was also compared to those obtained with conventional Pap staining. Two clinical endpoints for Pap staining (i.e., ≧LSIL and ≧HSIL) were used. Again, the standard for all calculations was the biopsy result.

TABLE 44

Comparison of Pap Test and Immunocytochemistry Method

| | ≧LSIL (with Pap test) | ≧HSIL (with Pap test) | ≧ASCUS (with ICC) |
|---|---|---|---|
| Sensitivity | 76.5% | 92.6% | 97.7% |
| | (52.7%, 90.4%)* | (76.6%, 97.9%) | (92.1%, 99.4%) |
| PPV | 59.1% | 26.0% | 31.0% |
| | (38.7%, 76.7%) | (18.3%, 35.6%) | (25.9%, 36.7%) |

*(95% confidence interval)

The results presented in Table 42 indicate that the immunocytochemistry method detected more high-grade cervical disease samples, while maintaining a high PPV.

There were 14 false negatives in this study using the immunocytochemistry kit. HPV testing was conducted on 13 of the 14 patient samples. No remaining sample was available for one of the false negative patients.

Genomic DNA was isolated from the cervical cytology samples using the NucleoSpin® Tissue DNA Kit (BD Clontech, Cat#635967). For quality control purposes, PCR analysis of beta-globin, a housekeeping gene, was performed.

HPV L1 gene amplification was performed as described in the art by both conventional L1 PCR with MY09/11 primer set and by nested PCR with MY09/11 and GP5+/6+ primer sets to improve detection sensitivity. DNA sequencing of the L1 amplicon was further performed to identify the type(s) of HPV(s) present.

Good quality genomic DNA was isolated from 10 out of the 13 clinical cytology samples. 3 samples had poor quality genomic DNA as indicated by beta-globin PCR analysis. HPV DNA was either undetectable or negative in 10 of the 13 samples using both conventional L1 PCR (with MY09/11 primers) and nested L1 PCR (with MY09/11 and GP5+/6+ primers). This data indicates that a sampling error occurred for a majority of the false negative samples, given that HPV is positive for high-grade cervical disease (sensitivity of >92%).

Example 9

MCM6 Antibody Selection

Polydoma Screening

Polydomas provided in multi-well tissue culture plates were screened to identify MCM 6 biomarker-specific antibodies that possess the desired traits of sensitivity and specificity. A tissue microarray comprising multiple normal (i.e., no CIN), CINIII, squamous cell carcinoma, and adenocarcinoma samples on a single slide was generated. Undiluted supernatants from each well containing a polydoma were assayed for positive staining of the tissue microarray. Background, i.e. non-specific binding, was essentially ignored at this stage. Eleven of the 35 polydomas tested produced positive staining results and were selected for further analysis.

In order to determine the specificity of the selected polydomas, the staining patterns obtained with the polydoma supernatants were compared with those obtained with a commercially available MCM 6 antibody (BD Transduction Laboratories). The staining patterns obtained with the polydoma supernatants appeared to be more specific than those observed with the commercial MCM 6 antibody (FIG. 17).

The 11 selected polydomas were then subjected to a limiting dilution process. Thirty limiting dilutions, resulting from the supernatants of the selected polydomas, were assayed for positive staining of a tissue microarray comprising multiple normal (i.e., no CIN), CINIII, squamous cell carcinoma, and adenocarcinoma samples. Two limiting dilution clones, 9D4.3 and 9D4.4, were selected as the best supernatants based on positive staining of abnormal and cancerous cervical tissue samples. Varying dilutions of these clones were then tested for their reactivity to NIL, LSIL, HSIL tissue and pooled liquid based cytology samples. Clone 9D4.3 at a 1:100 dilution produced the maximal signal to noise ratio and was selected for further characterization.

Characterization of MCM 6, Clone 9D4.3

In order to further characterize clone 9D4.3, the clone was assayed for positive staining of 40 liquid based cytology samples selected from the following diagnostic categories: NIL (7), LSIL (10), HSIL (18), and cervical carcinoma (5). Slides were prepared using the PrepStain™ slide processor (TriPath Imaging, Inc.) for each of the 40 samples. Two slides per sample were each stained with an MCM 2 antibody (Dako) and clone 9D4.3. The remaining slides were used for PAP staining or as a negative control.

To prepare slides, each sample was centrifuged for 2 minutes at 200× g to form a pellet, and the supernatant was decanted. 2 mL of deionized water was added to each sample, and the samples were vortexed and then centrifuged for 5 minutes at 600× g. After decanting the supernatant, an additional 700 μL of tris buffered water was added. Finally the samples were loaded onto the PrepStain™ slide processor (Tripath Imaging, Inc.), version 1.1, and the Transfer Only program was run.

All slides were held in 95% ETOH for at least 24 hours and no more than 3 days after preparation. Antigen retrieval for MCM2 was achieved by placing the slides in a 1× Target Retrieval Solution pH 6.0 (DAKO S1699)/dH20 bath, preheated to 95° C., for 25 minutes in a steamer. For MCM6, antigen accessibility was achieved by placing the slides in a 1× Tris pH 9.5 buffer (Biocare)/dH20 bath, preheated to 95° C., for 25 minutes in a steamer. After steaming, all slides were allowed to cool at room temperature for 20 minutes.

Slides were stained by immunocytochemistry using the DAKO Universal Autostainer as described in Example 1, "Automated Immunocytochemistry." The slides were screened and evaluated by an experienced cytotechnologist for a morphological determination of diagnostic category. The samples were assessed for marker staining intensity (0-3), percentage of positive-staining cells, and the location of the marker staining (nuclear, cytoplasmic, membrane, or a combination). Intensity of cell staining was given a score of 0-3. Cells scoring ≧1.5 were counted. Mature normal-appearing squamous cells and normal-appearing glandular cells were not counted as positive when staining brown. However, squamous metaplastic cells were counted as positive along with abnormal cells. The immunocytochemistry slides were then given a designation of TN (true negative), FN (false negative), TP (true positive), or FP (false positive).

TABLE 45

| | Clone 9D4.3 (MCM6) | | | | | |
|---|---|---|---|---|---|---|
| | TP | FP | FN | TN | Indet. | Total |
| NIL | 0 | 0 | 0 | 1 | 0 | 1 |
| LSIL | 0 | 1 | 0 | 9 | 0 | 10 |
| HSIL | 23 | 0 | 1 | 0 | 0 | 24 |
| Cancer | 5 | 0 | 0 | 0 | 0 | 5 |
| | 28 | 1 | 1 | 10 | 0 | 40 |

Sensitivity 0.9655
Specificity 0.9091
PPP 0.9655
NPP 0.9091

TABLE 46

| | MCM2 | | | | | |
|---|---|---|---|---|---|---|
| | TP | FP | FN | TN | Indet. | Total |
| NIL | 0 | 0 | 0 | 1 | 0 | 1 |
| LSIL | 0 | 1 | 0 | 9 | 0 | 10 |
| HSIL | 23 | 0 | 1 | 0 | 0 | 24 |
| Cancer | 4 | 0 | 1 | 0 | 0 | 5 |
| | 27 | 1 | 2 | 10 | 0 | 40 |

Sensitivity 0.9310
Specificity 0.9091
PPP 0.9643
NPP 0.8333
Calculations Used
Sensitivity = TP/(TP + FN)
Specificity = TN/(FP + TN)
Positive Predictive Power (PPP) = TP/(TP + FP)
Negative Predictive Power (NPP) = TN/(FN + TN)

The sensitivity and specificity for clone 9D4.3 was comparable to that obtained with the commercially available MCM2 antibody. One NIL case was negative for both antibodies. 9 of 10 LSIL cases were negative with clone 9D4.3 and the commercial MCM2 antibody. 23 of 24 HSIL cases were positive with clone 9D4.3 and the commercial MCM2 antibody. With the cervical cancer samples, 5 of 5 were positive with clone 9D4.3, and 4 of 5 were positive with the MCM 2 antibody.

Purification of MCM 6, Clone 9D4.3

Because of its sensitivity, specificity, and the presentation of a nuclear staining pattern, clone 9D4.3 was purified for further analysis. Purified antibody was obtained using Streamline rProteinA (Amersham Biosciences) affinity adsorption chromatography, in accordance with standard methods. The resulting antibody solution was then tested for reactivity against HSIL liquid-based cervical cytology pools at various dilutions between 1:500 and 1:6000. Signal was evident out to a titer of 1:6000.

Example 10

Real-Time PCR Detection of Biomarkers in Clinical Tissue Samples

TaqMan® real-time PCR was performed with the ABI Prism 7700 Sequence Detection System (Applied Biosystems). The primers and probes were designed with the aid of the Primer Express™ program, version 1.5 (Applied Biosystems), for specific amplification of the targeted cervical biomarkers (i.e., MCM7, $p21^{waf1}$, $p14^{ARF}$/p16, cyclin E1, and cyclin E2) in this study. The sequence information for primers and probes is shown below:

```
MCM7:
Primer Name: MCM7_T1T3-F
                                            (SEQ ID NO:25)
Sequence: CTCTGAGCCCGCCAAGC
Primer Name: MCM7_T1T3-R
                                            (SEQ ID NO:26)
Sequence: TGTAAGAACTTCTTAACCTTTTCCTTCTCTA
Probe Name: MCM7_T1T3-Probe
                                            (SEQ ID NO:27)
Sequence: CCCTCGGCAGCGATGGCACT
Primer Name: MCM7_T2T4-F
                                            (SEQ ID NO:28)
Sequence: GAGGAATCCCGAGCTGTGAA
Primer Name: MCM7_T2T4-R
                                            (SEQ ID NO:29)
Sequence: CCCGCTCCCGCCAT
Probe Name: MCM7_T2T4-Probe
                                            (SEQ ID NO:30)
Sequence: CCCATGTGCTTCTTTGTTTACTAAGAGCGGAA
Primer Name: MCM7_T2-F
                                            (SEQ ID NO:31)
Sequence: GTCCGAAGCCCCCAGAA
Primer Name: MCM7_T2-R
                                            (SEQ ID NO:32)
Sequence: CCCGACAGAGACCACTCACA
Probe Name: MCM7_T2-Probe
                                            (SEQ ID NO:33)
Sequence: CAGTACCCTGCTGAACTCATGCGCA
Primer Name: MCM7_T3T4-F
                                            (SEQ ID NO:34)
Sequence: CGCTACGCGAAGCTCTTTG
Primer Name: MCM7_T3T4-R
                                            (SEQ ID NO:35)
Sequence: CCTTTGTTTGCCATTGTTCTCTAA
Probe Name: MCM7_T3T4-Probe
                                            (SEQ ID NO:36)
Sequence: TGCCGTACAAGAGCTGCTGCCTCA p21^waf1:
Primer Name: p21T1T2-F
                                            (SEQ ID NO:37)
Sequence: CAAACGCCGGCTGATCTT
Primer Name: p21T1T2-R
                                            (SEQ ID NO:38)
Sequence: CCAGGACTGCAGGCTTCCT
Probe Name: p21T1T2-Probe
                                            (SEQ ID NO:39)
Sequence: CAAGAGGAAGCCCTAATCCGCCCA
Primer Name: p21T2-F
                                            (SEQ ID NO:40)
Sequence: GAGCGGCGGCAGACAA
Primer Name: p21T2-R
                                            (SEQ ID NO:41)
Sequence: CCGCGAACACGCATCCT
Probe Name: p21T2-Probe
                                            (SEQ ID NO:42)
Sequence: CCCAGAGCCGAGCCAAGCGTG
Primer Name: p21T3-F
                                            (SEQ ID NO:43)
Sequence: TGGAGACTCTCAGGGTCGAAA
Primer Name: p21T3-R
                                            (SEQ ID NO:44)
Sequence: TCCAGTCTGGCCAACAGAGTT
Probe Name: p21T3-Probe
                                            (SEQ ID NO:45)
Sequence: CGGCGGCAGACCAGCATGAC p14^ARF/p16:
Primer Name: p16T4-F
                                            (SEQ ID NO:46)
Sequence: GCC CTC GTG CTG ATG CTA CT
Primer Name: p16T4-R
                                            (SEQ ID NO:47)
Sequence: TCA TCA TGA CCT GGT CTT CTA GGA
Probe Name: p16T4-Probe
                                            (SEQ ID NO:48)
Sequence: AGC GTC TAG GGC AGC AGC CGC
Primer Name: p16T1-F
                                            (SEQ ID NO:49)
Sequence: TGCCCAACGCACCGA
Primer Name: p16T1-R
                                            (SEQ ID NO:50)
Sequence: GGGCGCTGCCCATCA
Probe Name: p16T1-Probe
                                            (SEQ ID NO:51)
Sequence: TCGGAGGCCGATCCAGGTCATG
Primer Name: p16T2-F
                                            (SEQ ID NO:52)
Sequence: AAGCTTCCTTTCCGTCATGC
Primer Name: p16T2-R
                                            (SEQ ID NO:53)
Sequence: CATGACCTGCCAGAGAGAACAG
Probe Name: p16T2-Probe
                                            (SEQ ID NO:54)
Sequence: CCCCCACCCTGGCTCTGACCA
Primer Name: p16T3-F
                                            (SEQ ID NO:55)
Sequence: GGAAACCAAGGAAGAGGAATGAG
Primer Name: p16T3-R
                                            (SEQ ID NO:56)
Sequence: TGTTCCCCCCTTCAGATCTTCT
```

-continued

Probe Name: p16T3-Probe (SEQ ID NO:57)
Sequence: ACGCGCGTACAGATCTCTCGAATGCT

Primer Name: p16Universal-F (SEQ ID NO:58)
Sequence: CACGCCCTAAGCGCACAT

Primer Name: p16 Universal-R (SEQ ID NO:59)
Sequence: CCTAGTTCACAAAATGCTTGTCATG

Probe Name: p16 Universal-Probe (SEQ ID NO:60)
Sequence: TTTCTTGCGAGCCTCGCAGCCTC Cyclin E1:
Primer Name: CCNE1T1T2-F (SEQ ID NO:61)
Sequence: AAAGAAGATGATGACCGGGTTTAC Primer Name: CCNE1T1T2-R (SEQ ID NO:62)
Sequence: GAGCCTCTGGATGGTGCAA Probe Name: CCNE1T1T2-P (SEQ ID NO:63)
Sequence: CAAACTCAACGTGCAAGCCTCGGA Primer Name: CCNE1T1-F (SEQ ID NO:64)
Sequence: TCCGCCGCGGACAA Primer Name: CCNE1T1-R (SEQ ID NO:65)
Sequence: CATGGTGTCCCGCTCCTT Probe Name: CCNE1T1-Probe (SEQ ID NO:66)
Sequence: ACCCTGGCCTCAGGCCGGAG Cyclin E2
Primer Name: CCNE2T1T2-F (SEQ ID NO:67)
Sequence: GGAATTGTTGGCCACCTGTATT Primer Name: CCNE2T1T2-R (SEQ ID NO:68)
Sequence: CTGGAGAAATCACTTGTTCCTATTTCT TaqMan Probe Name: CCNE2TLT2-P (SEQ ID NO:69)
Sequence: CAGTCCTTGCATTATCATTGAAACACCTCACA Primer Name: CCNE2T1T3-F (SEQ ID NO:70)
Sequence: TCAACTCATTGGAATTACCTCATTATTC Primer Name: CCNE2T1T3-R (SEQ ID NO:71)
Sequence: ACCATCAGTGACGTAAGCAAACTC TaqMan Probe Name: CCNE2T1T3-P (SEQ ID NO:72)
Sequence: CCAAACTTGAGGAAATCTATGCTCCTAAACTCCA Primer Name: CCNE2T2-F (SEQ ID NO:73)
Sequence: TTTTGAAGTTCTGCATTCTGACTTG Primer Name: CCNE2T2-R (SEQ ID NO:74)
Sequence: ACCATCAGTGACGTAAGCAAGATAA TaqMan Probe Name: CCNE2T2-P (SEQ ID NO:75)
Sequence: AACCACAGATGAGGTCCATACTTCTAGACTGGCT The probes were labeled with a fluorescent dye FAM (6-carboxyfluorescein) on the 5' base, and a quenching dye TAMRA (6-carboxytetramethylrhodamine) on the 3' base. The sizes of the amplicons were around 100 bp. 18S Ribosomal RNA was utilized as an endogenous control. An 18S rRNA probe was labeled with a fluorescent dye VIC™. Pre-developed 18S rRNA primer/probe mixture was purchased from Applied Biosystems. 5 μg of total RNA extracted from normal (N) or cancerous (T) cervical tissues was quantitatively converted to the single-stranded cDNA form with random hexamers by using the High-Capacity cDNA Archive Kit (Applied Biosystems). The following reaction reagents were prepared:

| 20X Master Mix of Primers/Probe (in 200 μl) | |
|---|---|
| 180 μM Forward primer | 20 μl |
| 180 μM Reverse primer | 20 μl |
| 100 μM TaqMan probe | 10 μl |
| H$_2$O | 150 μl |

| Final Reaction Mix (25 μl/well) | |
|---|---|
| 20X master mix of primers/probe | 1.25 μl |
| 2X TaqMan Universal PCR master mix (P/N: 4304437) | 12.5 μl |
| cDNA template | 5.0 μl |
| H$_2$O | 6.25 μl |

20× TaqMan Universal PCR Master Mix was purchased from Applied Biosystems. The final primer and probe concentrations, in a total volume of 25 μl, were 0.9 μM and 0.25 μM, respectively. 10 ng of total RNA was applied to each well. The amplification conditions were 2 minutes at 50° C., 10 minutes at 95° C., and a two-step cycle of 95° C. for 15 seconds and 60° C. for 60 seconds for a total of 40 cycles. At least three no-template control reaction mixtures were included in each run. All experiments were performed in triplicate.

At the end of each reaction, the recorded fluorescence intensity is used for the following calculations: $Rn^+$ is the Rn value of a reaction containing all components. $Rn^-$ is the Rn value of an unreacted sample (baseline value or the value detected in NTC). $\Delta Rn$ is the difference between $Rn^+$ and $Rn^-$ and is an indicator of the magnitude of the signal generated by the PCR. The comparative CT method, which assumes no known amount of standard but compares the relative amount of the target sequence to any reference value chosen (e.g., 18S rRNA), was used in this study. The TaqMan® Human Endogenous Control Plate protocol was used to convert raw data for real-time PCR data analysis.

Results

The results obtained with each biomarker and with the specific primers are listed below in tabular form. Results obtained with normal cervical tissue samples (i.e., NIL) are designated N; those obtained with cervical cancer tissues are labeled T.

TABLE 47

| | MCM7 TaqMan ® Results | | | | |
|---|---|---|---|---|---|
| Sample | T2 | T5 | T1T3 | T2T4 | T3T4 |
| CV01-T | 4 | 0.04 | 29.9 | 4.5 | 1.4 |
| CV03-T | 5.7 | 0.02 | 36.8 | 6.1 | 2.6 |
| CV05-T | 4.13 | 0.08 | 17.3 | 1.35 | 3.68 |

TABLE 47-continued

MCM7 TaqMan ® Results

| Sample | T2 | T5 | T1T3 | T2T4 | T3T4 |
|---|---|---|---|---|---|
| CV07-T | 2.6 | 0.06 | 18.77 | 0.88 | 3.27 |
| CV09-T | 4.96 | 0.08 | 15.01 | 3.69 | 3.22 |
| CV11-T | 5.9 | 0.01 | 7.37 | 3.08 | 1.75 |
| CV13-T | 6.74 | 0.04 | 19.74 | 4.55 | 4.11 |
| CV15-T | 3.04 | 0.05 | 3.65 | 3.43 | 1.25 |
| CV17-T | 5.21 | 0.02 | 20.07 | 2.74 | 1.56 |
| CV19-T | 3.34 | 0.09 | 21.17 | 2.88 | 6 |
| CV21-T | 6.7 | 0.08 | 10.64 | 4.75 | 4.59 |
| CV23-T | 7.08 | 0.33 | 32.17 | 5.6 | 4.25 |
| CV25-T | 4.87 | 0.03 | 18.11 | 4.58 | 4.51 |
| CV27-T | 4.24 | 0.03 | 36.25 | 4.6 | 2.82 |
| MEAN | 4.89 | 0.07 | 20.50 | 3.77 | 3.22 |
| MEDIAN | 4.89 | 0.05 | 19.74 | 3.77 | 3.22 |
| STD | 1.32 | 0.07 | 9.46 | 1.39 | 1.32 |
| CV02-N | 2.5 | 0.02 | 10.6 | 2.6 | 1.1 |
| CV04-N | 4.6 | 0.02 | 7.1 | 4.8 | 2.4 |
| CV06-N | 1.75 | 0.01 | 2.14 | 1.36 | 2.63 |
| CV08-N | 1.35 | 0.01 | 4.8 | 1.71 | 1.54 |
| CV10-N | 5.6 | 0.03 | 5.07 | 5.12 | 1.85 |
| CV12-N | 5.68 | 0.02 | 7.34 | 3.19 | 2.29 |
| CV16-N | 4.35 | 0.08 | 3.72 | 2.75 | 1.78 |
| CV18-N | 3.98 | 0.01 | 4.74 | 3.63 | 1.7 |
| CV20-N | 2.03 | 0.03 | 5.42 | 1.4 | 2.78 |
| CV22-N | 2.66 | 0.02 | 4.33 | 2.26 | 2.42 |
| CV24-N | 4.88 | 0.09 | 9.03 | 1.53 | 2.77 |
| CV28-N | 2.71 | 0.01 | 10.38 | 1.36 | 1.7 |
| MEAN | 3.51 | 0.03 | 6.22 | 2.64 | 2.08 |
| MEDIAN | 3.51 | 0.02 | 5.42 | 2.60 | 2.08 |
| STD | 1.40 | 0.03 | 2.48 | 1.21 | 0.50 |

TABLE 48 p21$^{wafl}$ TaqMan ® Results

| Patients | T1T2 | T2 | T3 |
|---|---|---|---|
| Pt01-T | 23.33 | 0.06 | 0.00 |
| Pt02-T | 14.66 | 0.01 | 0.00 |
| Pt03-T | 11.86 | 0.00 | 0.00 |
| Pt04-T | 27.04 | 0.01 | 0.00 |
| Pt05-T | 14.72 | 0.00 | 0.00 |
| Pt06-T | 22.84 | 0.01 | 0.00 |
| Pt07-T | 14.04 | 0.00 | 0.00 |
| Pt08-T | 31.93 | 0.01 | 0.01 |
| Pt09-T | 35.02 | 0.00 | 0.00 |

TABLE 48-continued p21$^{wafl}$ TaqMan ® Results

| Patients | T1T2 | T2 | T3 |
|---|---|---|---|
| Pt10-T | 13.2 | 0.00 | 0.00 |
| Pt11-T | 24.87 | 0.01 | 0.00 |
| Pt12-T | 10.85 | 0.00 | 0.00 |
| Pt13-T | 36.51 | 0.02 | 0.01 |
| Pt14-T | 12.72 | 0.00 | 0.00 |
| Pt15-T | 10.64 | 0.00 | 0.00 |
| Pt16-T | 22.58 | 0.04 | 0.00 |
| Pt17-T | 39.64 | 0.14 | 0.04 |
| Pt01-N | 4.57 | 0.03 | 0.00 |
| Pt02-N | 5.57 | 0.00 | 0.00 |
| Pt03-N | 3.54 | 0.00 | 0.00 |
| Pt04-N | 8.18 | 0.00 | 0.00 |
| Pt05-N | 5.4 | 0.10 | 0.00 |
| Pt06-N | 11.01 | 0.00 | 0.00 |
| Pt08-N | 10.39 | 0.00 | 0.00 |
| Pt09-N | 9.11 | 0.00 | 0.00 |
| Pt10-N | 4.41 | 0.00 | 0.00 |
| Pt11-N | 8.64 | 0.00 | 0.00 |
| Pt12-N | 3.03 | 0.00 | 0.00 |
| Pt14-N | 3.55 | 0.00 | 0.00 |
| Pt15-N | 2.42 | 0.01 | 0.00 |
| Pt17-N | 11.46 | 0.05 | 0.01 |
| T-mean | 21.5559 | | |
| N-mean | 6.52 | | |
| St. T-test = | 7.3E−06 | | |

TABLE 49 p14$^{ARF/p16}$ TaqMan ® Results

| Patient | T1 | T2 | T3 | T4 | UNIVERSAL |
|---|---|---|---|---|---|
| Pt01-T | 0.2 | 0.1 | 0.2 | 0.2 | 0.2 |
| P102-T | 16.3 | 11.2 | 5.1 | 21.7 | 36.5 |
| Pt03-T | 16.5 | 6.2 | 3.1 | 15.1 | 29.6 |
| Pt04-T | 10.1 | 2.8 | 2.6 | 13.2 | 27.7 |
| Pt05-T | 12.7 | 3.6 | 2.1 | 11.3 | 23.1 |
| Pt01-N | 0.1 | 0.1 | 0.1 | 0.1 | 0.1 |
| P102-N | 2.5 | 2.6 | 1.6 | 2.7 | 6.8 |
| Pt04-N | 2.6 | 0.6 | 0.8 | 2.4 | 5.8 |
| Pt05-N | 2.1 | 0.8 | 0.7 | 4.1 | 4.6 |
| T-Mean | 11.2 | 4.8 | 2.6 | 12.3 | 23.4 |
| N-Mean | 1.8 | 1.0 | 0.8 | 2.3 | 4.3 |

TABLE 50

Cyclin E1 TaqMan ® Results

| Patient | T1T2 Cancer M. | Cancer SD | T1T2 Normal M. | Normal SD | T1 Cancer M. | Cancer SD | T1 Normal M. | Normal SD |
|---|---|---|---|---|---|---|---|---|
| Pt 01 | 12.19 | 0.12 | 4.11 | 0.13 | 1.34 | 0.04 | 0.5 | 0.03 |
| Pt 02 | 16.72 | 0.21 | 4.44 | 0.34 | 1.35 | 0.02 | 0.47 | 0.05 |
| Pt 03 | 11.45 | 0.41 | 2.81 | 0.13 | 1.17 | 0.01 | 0.06 | 0.02 |
| Pt 04 | 21.33 | 0.45 | 5.33 | 0.09 | 0.76 | 0.1 | 0.23 | 0.01 |
| Pt 05 | 11.17 | 0.25 | 3.68 | 0.15 | 0.95 | 0.05 | 0.15 | 0.03 |
| Pt 06 | 21.65 | 0.24 | 3.11 | 0.22 | 0.89 | 0.03 | 0.13 | 0.02 |
| Pt 07 | 23.26 | 0.54 | 0 | 0 | 0.75 | 0.06 | 0 | 0.01 |
| Pt 08 | 8.37 | 0.24 | 3.1 | 0.01 | 0.12 | 0.01 | 0.13 | 0.02 |
| Pt 09 | 17.74 | 0.43 | 2.17 | 0.08 | 0.73 | 0.02 | 0.09 | 0.01 |
| Pt 10 | 18.51 | 0.29 | 4.56 | 0.17 | 1.37 | 0.03 | 0.41 | 0.04 |
| Pt 11 | 10.58 | 0.52 | 3.92 | 0.12 | 0.57 | 0.01 | 0.23 | 0.03 |
| Pt 12 | 33.67 | 0.58 | 7.87 | 0.1 | 0.78 | 0.01 | 0.28 | 0.05 |
| Pt 13 | 36.9 | 0.41 | 0 | 0 | 1.05 | 0.04 | 0 | 0 |
| Pt 14 | 31.01 | 0.29 | 6.01 | 0.26 | 1.68 | 0.05 | 0.24 | 0.03 |
| Pt 15 | 7.35 | 0.23 | 1.24 | 0.09 | 0.34 | 0.08 | 0.08 | 0.02 |
| Pt 16 | 12.71 | 0.61 | 3.72 | 0 | 1.1 | 0.06 | 0.07 | 0.01 |
| Pt 17 | 12.13 | 0.21 | 11.46 | 0.15 | 0.34 | 0.07 | 0.05 | 0.01 |
| Pt 18 | 14.22 | 0.14 | 5.94 | 0.06 | 0.73 | 0.08 | 0.26 | 0.04 |

TABLE 50-continued

Cyclin E1 TaqMan® Results

| Patient | T1T2 Cancer M. | Cancer SD | T1T2 Normal M. | Normal SD | T1 Cancer M. | Cancer SD | T1 Normal M. | Normal SD |
|---|---|---|---|---|---|---|---|---|
| Pt 19 | 12.69 | 0.81 | 3.52 | 0.02 | 0.41 | 0.04 | 0.24 | 0.02 |
| Pt 20 | 16.56 | 0.16 | 6.1 | 0.12 | 0.17 | 0.02 | 0.06 | 0 |
| Pt 21 | 11.63 | 0.23 | 3.01 | 0.06 | 0.54 | 0.04 | 0.23 | 0.01 |
| Pt 22 | 17.39 | 0.34 | 2.36 | 0.02 | 0.47 | 0.02 | 0.24 | 0.05 |
| Pt 23 | 16.56 | 0.16 | 2.1 | 0.02 | 0.18 | 0.03 | 0.09 | 0.01 |
| Pt 24 | 22.23 | 0.33 | 4.06 | 0.28 | 1.9 | 0.17 | 0.52 | 0.01 |
| Pt 25 | 13.98 | 0.48 | 3.72 | 0.05 | 0.54 | 0.04 | 0.23 | 0.01 |
| Pt 26 | 22.71 | 0.76 | 4.48 | 0.07 | 0.47 | 0.02 | 0.24 | 0.05 |
| Pt 27 | 16.17 | 0.4 | 5.64 | 0.3 | 0.18 | 0 | 0.12 | 0.01 |
| Pt 28 | 12.6 | 0.56 | 3.8 | 0.06 | 0.29 | 0.03 | 0.05 | 0 |
| Pt 29 | 13.69 | 0.34 | 3.1 | 0.18 | 0.29 | 0.03 | 0.11 | 0 |
| Pt 30 | 17.69 | 0.61 | 4.3 | 0.11 | 0.36 | 0.01 | 0.03 | 0 |
| Pt 31 | 20.46 | 0.3 | 3.91 | 0.21 | 0.47 | 0.03 | 0.08 | 0 |
| Pt 32 | 18.38 | 0.18 | 3.16 | 0.06 | 0.42 | 0.02 | 0.17 | 0.01 |
| Pt 33 | 21.1 | 0.62 | 4.52 | 0.33 | 1.07 | 0.05 | 0.24 | 0.01 |
| Pt 34 | 21.5 | 1.37 | 4.56 | 0.13 | 0.24 | 0.01 | 0.11 | 0.01 |
| Average | 17.54 | | 4.26 | | 0.68 | | 0.20 | |
| T/N | 4.1 | | | | | | | |
| t-test P= | 7.80E-14 | | | | | | | |

TABLE 51

Cyclin E2 TaqMan® Results

| Patients | T1T2 | T1T2 Std. Dev. | T1T3 | T1T3 Std. Dev. | T2 | T2 Std. Dev. |
|---|---|---|---|---|---|---|
| Pt01-T | 13.17 | 1.02 | 16.11 | 0.39 | 0.01 | 0.00 |
| Pt02-T | 13.42 | 0.3 | 18.12 | 2.21 | 0.15 | 0.02 |
| Pt03-T | 13.64 | 0.50 | 17.40 | 2.16 | 0.05 | 0.01 |
| Pt04-T | 19.37 | 1.41 | 24.26 | 1.01 | 0.01 | 0.00 |
| Pt05-T | 10.59 | 1.1 | 14.71 | 1.58 | 0.17 | 0.02 |
| Pt06-T | 7.96 | 0.91 | 9.32 | 0.51 | 0.06 | 0.01 |
| Pt07-T | 14.1 | 1.73 | 16.92 | 0.84 | 0.54 | 0.06 |
| Pt08-T | 8.11 | 0.67 | 9.50 | 0.66 | 0.34 | 0.07 |
| Pt09-T | 13.04 | 0.72 | 18.27 | 0.99 | 0.02 | 0.00 |
| Pt10-T | 19.56 | 2.29 | 23.42 | 0.00 | 0.02 | 0.01 |
| Pt11-T | 16.8 | 1.57 | 18.71 | 2.15 | 0.08 | 0.01 |
| Pt12-T | 16.05 | 0.85 | 18.81 | 0.74 | 0.91 | 0.01 |
| Pt13-T | 14.91 | 0.87 | 18.51 | 1.59 | 0.61 | 0.16 |
| Pt14-T | 14.89 | 0.32 | 20.49 | 0.86 | 0.42 | 0.03 |
| Pt15-T | 12.44 | 0.47 | 15.26 | 1.00 | 0.68 | 0.18 |
| Pt16-T | 11.54 | 1.58 | 13.13 | 0.75 | 1.02 | 0.14 |
| Pt17-T | 6.78 | 0.47 | 7.91 | 0.45 | 0.85 | 0.10 |
| Pt01-N | 4.89 | 0.21 | 5.94 | 0.53 | 0.00 | 0.00 |
| Pt02-N | 6.32 | 0.47 | 8.91 | 0.61 | 0.13 | 0.00 |
| Pt03-N | 4.8 | 0.31 | 5.89 | 0.30 | 0.04 | 0.00 |
| Pt04-N | 13.28 | 0.74 | 15.28 | 1.37 | 0.01 | 0.00 |
| Pt05-N | 6.51 | 1.2 | 9.04 | 0.82 | 0.16 | 0.02 |
| Pt06-N | 4.96 | 0.83 | 6.41 | 0.84 | 0.05 | 0.01 |
| Pt08-N | 6.48 | 0.73 | 6.82 | 0.60 | 0.07 | 0.02 |
| Pt09-N | 3.74 | 0.48 | 4.63 | 0.66 | 0.03 | 0.01 |
| Pt10-N | 10.32 | 0.93 | 11.31 | 0.89 | 0.02 | 0.00 |
| Pt11-N | 10.34 | 0.26 | 13.90 | 0.53 | 0.04 | 0.04 |
| Pt12-N | 13.81 | 1.69 | 16.60 | 1.45 | 0.24 | 0.07 |
| Pt14-N | 6.92 | 0.63 | 9.07 | 0.95 | 0.14 | 0.03 |
| Pt15-N | 4.8 | 0.73 | 8.55 | 1.40 | 0.10 | 0.03 |
| Pt17-N | 5.33 | 0.2 | 5.78 | 0.27 | 0.23 | 0.07 |
| T-mean | 13.32 | | 16.52 | | 0.35 | |
| N-mean | 7.32 | | 9.15 | | 0.09 | |
| St. T-test | 4.16E-05 | | 3.31742E-05 | | 0.008813 | |

Example 11

Real-Time PCR Detection of Biomarkers in Clinical Tissue Samples

TaqMan® real-time PCR was performed as described in Example 9 using cervical cancer tissue samples (e.g., adenocarcinoma, squamous cell carcinoma) and normal cervical tissue samples. The primers and probes were designed with the aid of the Primer Express™ program, version 1.5 (Applied Biosystems), for specific amplification of the targeted cervical biomarkers (i.e., MCM2, MCM6, MCM7, and Topo2A) in this study. The sequence information for primers and probes is shown below:

```
TaqMan Primers
MCM2:
Primer Name: MCM2-F
                                           (SEQ ID NO:80)
Sequence: 5'-GGAGGTGGTACTGGCCATGTA-3'

Primer Name: MCM2-R
                                           (SEQ ID NO:81)
Sequence: 5'-GGGAGATGCGGACATGGAT-3'

TaqMan Probe Name: MCM2-P
                                           (SEQ ID NO:82)
Sequence: 5'-CCAAGTACGACCGCATCACCAACCA-3'

MCM6:
Primer Name: MCM6-F
                                           (SEQ ID NO:83)
Sequence: 5'-CATTCCAAGACCTGCCTACCA-3'

Primer Name: MCM6-R
                                           (SEQ ID NO:84)
Sequence: 5'-ATGCGAGTGAGCAAACCAATT-3'

TaqMan Probe Name: MCM6-P
                                           (SEQ ID NO:85)
Sequence: 5'-ACACAAGATTCGAGAGCTCACCTCATCCA-3'

MCM7:
Primer Name: MCM7_T1T3-F
                                           (SEQ ID NO:25)
Sequence: CTCTGAGCCCGCCAAGC Primer Name: MCM7_T1T3-R
```

```
                                              -continued
                                              (SEQ ID NO:26)
Sequence: TGTAAGAACTTCTTAACCTTTTCCTTCTCTA Probe Name: MCM7_T1T3-Probe
                                              (SEQ ID NO:27)
Sequence: CCCTCGGCAGCGATGGCACT Primer Name: MCM7_T2T4-F
                                              (SEQ ID NO:28)
Sequence: GAGGAATCCCGAGCTGTGAA Primer Name: MCM7_T2T4-R
                                              (SEQ ID NO:29)
Sequence: CCCGCTCCCGCCAT Probe Name: MCM7_T2T4-Probe
                                              (SEQ ID NO:30)
Sequence: CCCATGTGCTTCTTTGTTTACTAAGAGCGGAA Primer Name: MCM7_T2-F
                                              (SEQ ID NO:31)
Sequence: GTCCGAAGCCCCCAGAA Primer Name: MCM7_T2-R
                                              (SEQ ID NO:32)
Sequence: CCCGACAGAGACCACTCACA Probe Name: MCM7_T2-Probe
                                              (SEQ ID NO:33)
Sequence: CAGTACCCTGCTGAACTCATGCGCA
```

```
                                              -continued
Primer Name: MCM7_T3T4-F
                                              (SEQ ID NO:34)
Sequence: CGCTACGCGAAGCTCTTTG Primer Name: MCM7_T3T4-R
                                              (SEQ ID NO:35)
Sequence: CCTTTGTTTGCCATTGTTCTCTAA Probe Name: MCM7_T3T4-Probe
                                              (SEQ ID NO:36)
Sequence: TGCCGTACAAGAGCTGCTGCCTCA TOPO2A:
Primer Name: TOP2A_F
                                              (SEQ ID NO:86)
Sequence: 5'-GGCTACATGGTGGCAAGGA-3'

Primer Name: TOP2A_R
                                              (SEQ ID NO:87)
Sequence: 5'-TGGAAATAACAATCGAGCCAAAG-3'

TaqMan Probe Name: TOP2A_P
                                              (SEQ ID NO:88)
Sequence: 5'-TGCTAGTCCACGATACATCTTTACAATGCTCAGC-3'
```

Results

The results obtained for each biomarker are listed below in tabular form. The data is also summarized below.

TABLE 52

| | | | | | MCM6 | MCM7 | TOP2A |
|---|---|---|---|---|---|---|---|
| Patient | TPO ID | Path. Diag | HPV Type | MCM2 TaqM | TaqMan | TaqM | TaqM |
| Pt 01 | CV-001 | Sq. Cell CA | HPV16 | 8.93 | 11.31 | 29.9 | 23.76 |
| Pt 02 | CV-003 | Adeno CA | HPV18 | 10.94 | 14.29 | 36.8 | 25.28 |
| Pt 03 | CV-005 | Adeno CA | HPV18 | 17.67 | 13.84 | 17.3 | 23.18 |
| Pt 04 | CV-007 | Sq. Cell CA | HPV16 | 23.61 | 13.3 | 18.77 | 23.26 |
| Pt 05 | CV-009 | Sq. Cell CA | HPV16 | 9.3 | 11.26 | 15.01 | 20.33 |
| Pt 06 | CV-011 | Sq. Cell CA | HPV16 | 13.86 | 11.58 | 7.37 | 8.37 |
| Pt 07 | CV-013 | Adeno CA | HPV18 | 27.03 | 16.32 | 19.74 | 34.29 |
| Pt 08 | CV-015 | Sq.Cell CA | HPV16, HPV18, + | 8.28 | 8.16 | 3.65 | 8.57 |
| Pt 09 | CV-017 | Sq. Cell CA | HPV18 | 12.61 | 13.56 | 20.07 | 11.31 |
| Pt 10 | CV-019 | Sq Cell CA | HPV18 | 31.88 | 23.38 | 21.17 | 27.48 |
| Pt 11 | CV-021 | Sq. Cell CA | HPV16 | 11.27 | 14.76 | 10.64 | 12.73 |
| Pt 12 | CV-023 | Sq. Cell CA | HPV16 | 11.39 | 11.29 | 32.17 | 21.11 |
| Pt 13 | CV-025 | Sq. Cell CA | HPV16 | 23.88 | 18.98 | 18.11 | 27.96 |
| Pt 14 | CV-027 | Sq. Cell CA | HPV18, HPV16, + | 12.26 | 15.53 | 36.25 | 26.63 |
| Pt 15 | CV-029 | Sq Cell Carcinoma | HPV16 | 6.56 | 7.92 | 9.64 | 7.81 |
| Pt 16 | CV-031 | Sq Cell Carcinoma | HPV73 | 28.12 | 12.21 | 27.3 | 21.4 |
| Pt 17 | CV-033 | Sq Cell Carcinoma | HPV16 | 8.76 | 7.59 | 14.37 | 12.42 |
| Pt 18 | CV-035 | Sq Cell Carcinoma | HPV16 | 21.4 | 12.65 | 23.63 | 27.57 |
| Pt 19 | CV-037 | Sq Cell Carcinoma | HPV18 | 12.59 | 13.06 | 14.37 | 9.24 |

TABLE 52-continued

Snap-frozen Cervical Cancer Tissue Samples

| Patient | TPO ID | Path. Diag | HPV Type | MCM2 TaqM | MCM6 TaqMan | MCM7 TaqM | TOP2A TaqM |
|---|---|---|---|---|---|---|---|
| Pt 20 | CV-039 | Adenosqu. Cell CA | HPV16, HPV18, + | 7.24 | 8.17 | 16.97 | 15.13 |
| Pt 21 | CV-041 | Sq Cell CA | HPV16 | 9.61 | 11.84 | 13.88 | 11.92 |
| Pt 22 | CV-043 | Sq Cell CA | HPV16 | 21.57 | 13.21 | 18.31 | 24.19 |
| Pt 23 | CV-045 | Sq Cell CA | HPV16 | 21.19 | 13.18 | 18.76 | 19.97 |
| Pt 24 | CV-047 | Sq Cell CA | HPV18 | 24.61 | 19.09 | 20.19 | 28.14 |
| Pt 25 | CV-049 | Sq Cell CA | HPV18 | 11.43 | 10.2 | 13.70 | 10.55 |
| Pt 26 | CV-051 | Sq Cell CA | HPV16 | 24.25 | 20.54 | 23.26 | 33.26 |
| Pt 27 | CV-053 | Sq Cell CA | HPV45 | 26.74 | 21.34 | 20.96 | 20.34 |
| Pt 28 | CV-055 | Sq Cell CA | HPV16, HPV18, + | 12.65 | 12 | 14.42 | 12.17 |
| Pt 29 | CV-057 | Sq Cell CA | HPV16 | 16 | 14.72 | 25.46 | 22.16 |
| Pt 30 | CV-059 | Sq Cell CA | HPV16, HPV18, + | 22.55 | 17.87 | 15.30 | 25.54 |
| Pt 31 | CV-061 | Sq Cell CA | HPV16 | 24.08 | 21.88 | 23.11 | 25.28 |
| Pt 32 | CV-063 | Sq Cell CA | HPV18, HPV16, + | 24.16 | 12.55 | 21.63 | 22.39 |
| Pt 33 | CV-065 | Sq Cell CA | HPV16 | 26.63 | 16.05 | 27.56 | 28.84 |
| Pt 34 | CV-067 | Sq Cell CA | HPV16 | 19.61 | 23.28 | 19.03 | 25.57 |

TABLE 53

Adjacent Normal Tissue Samples

| Patient | TPO ID | HPV Type | MCM2 TaqM | MCM6 TaqMan | MCM7 TaqM | TOP2A TaqM |
|---|---|---|---|---|---|---|
| Pt 01 | CV-002 | Negative | 3.04 | 4.4 | 10.6 | 10.52 |
| Pt 02 | CV-004 | Negative | 6.26 | 6.28 | 7.1 | 9.06 |
| Pt 03 | CV-006 | HPV18 | 2.06 | 2.53 | 2.14 | 3.86 |
| Pt 04 | CV-008 | Negative | 3.14 | 4.15 | 4.8 | 8.03 |
| Pt 05 | CV-010 | Negative | 2.2 | 3.45 | 5.07 | 6.91 |
| Pt 06 | CV-012 | Negative | 2.06 | 2.29 | 7.34 | 6.82 |
| Pt 07 | CV-014 | Negative | N/A | N/A | N/A | N/A |
| Pt 08 | CV-016 | Negative | 2.55 | 3.13 | 3.72 | 2.02 |
| Pt 09 | CV-018 | Negative | 2.09 | 3.09 | 4.74 | 1.24 |
| Pt 10 | CV-020 | Negative | 8.15 | 6.76 | 5.42 | 10.41 |
| Pt 11 | CV-022 | Negative | 4.53 | 5.34 | 4.33 | 6.64 |
| Pt 12 | CV-024 | Negative | 1.94 | 2.45 | 9.03 | 6.13 |
| Pt 13 | CV-026 | Negative | N/A | N/A | N/A | N/A |
| Pt 14 | CV-028 | Negative | 2.62 | 2.95 | 10.38 | 5.3 |
| Pt 15 | CV-030 | Negative | 1.14 | 1.28 | 2.06 | 1.54 |
| Pt 16 | CV-032 | Negative | N/A | N/A | N/A | N/A |
| Pt 17 | CV-034 | Negative | 1.24 | 1.91 | 1.32 | 0.42 |
| Pt 18 | CV-036 | Negative | 3.4 | 1.89 | 4.01 | 4.32 |
| Pt 19 | CV-038 | Negative | 3.48 | 4.98 | 5.60 | 7.92 |
| Pt 20 | CV-040 | Negative | 1.84 | 3.28 | 3.73 | 1.38 |
| Pt 21 | CV-042 | Negative | 1.53 | 3.3 | 4.77 | 1.01 |
| Pt 22 | CV-044 | Negative | 2.65 | 4.03 | 2.74 | 2.59 |
| Pt 23 | CV-046 | Negative | 3.09 | 3.53 | 5.90 | 3.42 |
| Pt 24 | CV-048 | HPV18 | 2.57 | 5.19 | 3.82 | 5.32 |
| Pt 25 | CV-050 | Negative | 5.84 | 4.64 | 7.78 | 9.14 |
| Pt 26 | CV-052 | Negative | 5.11 | 5.22 | 5.37 | 5.13 |
| Pt 27 | CV-054 | Negative | 2.91 | 3.29 | 5.10 | 0.76 |
| Pt 28 | CV-056 | Negative | 4.14 | 3.74 | 5.54 | 4.15 |
| Pt 29 | CV-058 | HPV16 | 2.83 | 4.98 | 10.13 | 7.57 |
| Pt 30 | CV-060 | Negative | 6.41 | 5 | 5.39 | 10.05 |
| Pt 31 | CV-062 | Negative | 5.72 | 4.93 | 9.29 | 9.95 |
| Pt 32 | CV-064 | Negative | 8.06 | 5.41 | 7.64 | 9 |

TABLE 53-continued

Adjacent Normal Tissue Samples

| Patient | TPO ID | HPV Type | MCM2 TaqM | MCM6 TaqMan | MCM7 TaqM | TOP2A TaqM |
|---|---|---|---|---|---|---|
| Pt 33 | CV-066 | Negative | 9.93 | 7.94 | 10.78 | 9.95 |
| Pt 34 | CV-068 | Negative | 2.36 | 6.39 | 5.73 | 1.81 |

Summary of Results

TABLE 54

Tumor vs adjacent normal

| Marker | Tumor (M ± SD) | Normal (M ± SD) | R | P |
|---|---|---|---|---|
| MCM2 | 17.43 ± 7.34 | 3.71 ± 2.21 | 4.70 | <0.0001 |
| MCM6 | 14.32 ± 4.32 | 4.12 ± 1.56 | 3.48 | <0.0001 |
| MCM7 | 19.38 ± 6.94 | 5.85 ± 2.59 | 3.31 | <0.0001 |
| TOP2A | 20.53 ± 7.54 | 5.56 ± 3.33 | 3.69 | <0.0001 |

M: Mean;
SD: Standard Deviation;
R: Ratio of the means of tumor versus normal;
P: P value of t-test.

TABLE 55

HPV-16 vs HPV-18

| Marker | Tumor HPV type | Cases | Tumor (M ± SD) | Normal (M ± SD) |
|---|---|---|---|---|
| MCM2 | 16 | 18 | 16.77 ± 6.78 | 3.29 ± 2.13 |
|  | 18 | 8 | 17.23 ± 8.16 | 3.99 ± 2.40 |
|  | 16 + 18 | 6 | 14.52 ± 7.18 | 4.27 ± 2.47 |
| MCM6 | 16 | 18 | 14.19 ± 4.44 | 3.97 ± 1.75 |
|  | 18 | 8 | 14.24 ± 4.10 | 4.35 ± 1.54 |
|  | 16 + 18 | 6 | 12.38 ± 3.89 | 3.92 ± 1.04 |
| MCM7 | 16 | 18 | 19.39 ± 6.94 | 6.07 ± 2.98 |
|  | 18 | 8 | 17.23 ± 4.16 | 5.07 ± 1.91 |
|  | 16 + 18 | 6 | 18.04 ± 7.71 | 6.07 ± 2.56 |
| TOP2A | 16 | 18 | 20.92 ± 7.38 | 5.46 ± 3.26 |
|  | 18 | 8 | 19.78 ± 9.52 | 6.19 ± 3.33 |
|  | 16 + 18 | 6 | 18.41 ± 7.49 | 5.32 ± 3.57 |

TABLE 56

Squamous Cell Carcinoma vs Adenocarcinoma

| Marker | Histopathology | Cases | Tumor (M ± SD) | Normal (M ± SD) |
|---|---|---|---|---|
| MCM2 | SCC | 30 | 17.66 ± 7.28 | 3.74 ± 2.23 |
|  | AC | 4 | 15.72 ± 8.69 | 3.39 ± 2.49 |
| MCM6 | SCC | 30 | 14.48 ± 4.44 | 4.13 ± 1.55 |
|  | AC | 4 | 13.16 ± 3.49 | 4.03 ± 1.98 |
| MCM7 | SCC | 30 | 19.27 ± 7.25 | 6.01 ± 2.58 |
|  | AC | 4 | 20.20 ± 4.57 | 4.32 ± 2.53 |
| TOP2A | SCC | 30 | 20.01 ± 7.47 | 5.65 ± 3.34 |
|  | AC | 4 | 21.47 ± 7.87 | 4.77 ± 3.92 |

SCC: Squamous Cell Carcinoma;
AC: Adenocarcinoma.

Example 12

Real-Time PCR Detection of Biomarkers in Cervical and Breast Cancer Cell Lines

TaqMan® real-time PCR was performed to detect MCM2, MCM6 and MCM7 expression levels in cervical and breast cancer cell lines.

Experimental Design and Protocols

Three human cervical cancer cell lines of SiHa, Caski and HeLa and three human breast cancer cell lines of MCF-7, SK-BR3 and CAMA were purchased from ATCC and used in this experiment. Total cellular RNA was extracted from freshly cultured cells by RNeasy® Protect Mini kit (Qiagen, Valencia, Calif.) and converted into the single stranded cDNA form with random hexamers using the High-Capacity cDNA Archive Kit (Applied Biosystems, P/N: 4322171). Real-time PCR was performed on the ABI Prism® 7700 Sequence Detection System using TaqMan® Universal PCR Master Mix (Applied Biosystems, Inc., Foster City, Calif.).

The primers and probes for specific amplification of MCM2, MCM6 and MCM7 were designed with ABI Primer Express™ program, v1.5. MCM7 contains four transcriptional variants: transcript variant 1 (T1, refseq NM_005916) and transcript variant 2 (T2, refseq NM_182776) were identified in NCBI Entrez nucleotide database. Variant T3 and T4 have alternate exons near the 5'-end as analyzed by EST assembly through NCBI's Model Maker. Primers and probes were designed as T1T3, T2T4, T2 and T3T4 specifically for detecting variants T1 and T3, T2 and T4, T2, and T3 and T4, respectively. The sequences of primers and probes are shown above in Example 10 and 11.

The probes were labeled with a fluorescent dye FAM (6-carboxyfluorescein) on the 5' base, and a quenching dye TAMRA (6-carboxytetramethylrhodamine) on the 3' base. 18S ribosomal RNA was utilized as endogenous control. 18S rRNA probe was labeled with a fluorescent dye VIC. Pre-developed 18S rRNA primer/probe mixture was purchased from Applied Biosystems. 10 ng of cDNA were applied to the reaction mixture containing 0.9 μM and 0.25 μM of the primers and probes, respectively, in a total volume of 25 μl. The amplification conditions were: 2 minutes at 50° C., 10 minutes at 95° C., and a two-steps cycle of 95° C. for 15 seconds and 60° C. for 60 seconds, for a total of 40 cycles. At least three no-template control reaction mixtures were included in each run. All experiments were performed in duplicate. The relative quantification method was employed to calculate the expression levels of target genes relative to the 18S endogenous control, based on their CT values following the ABI's user manual (P/N 4303859).

Results

The results obtained for each biomarker are listed below in tabular form.

TABLE 57

Biomarker Expression Cervical and Breast Cancer Cell Lines

|  | SiHa | Caski | HeLa | MCF7 | SK-BR3 | CAMA |
|---|---|---|---|---|---|---|
| MCM2 | 21.4 | 5.01 | 8.79 | 18.84 | 7.65 | 17.32 |
| MCM6 | 12.34 | 5.77 | 6.46 | 12.6 | 5.44 | 13.14 |
| MCM7 | 20.53 | 17.27 | 8.31 | 26.91 | 30.38 | 25.36 |

Conclusions

The cervical HeLa cell line was shown to have low-expression levels of MCM2, MCM6 and MCM7 biomarkers. The cervical SiHa, breast MCM7, and CAMA cell lines all showed overexpression of MCM2, MCM6 and MCM7 biomarkers. Cervical Caski and breast SK-BR3 cell lines showed overexpression of MCM7, but low-expression for MCM2 and MCM6.

Example 13

Induction of Cervical Biomarker Expression in 293 Cells by Transient HPV16 E6/E7 Gene Transfection TaqMan® real-time PCR assay was used to investigate the linkage of cervical biomarker expression with high-risk HPV oncogene transcription in an HEK 293 cell line system.

Experimental Design and Protocols

A tetracycline regulated expression system (T-Rex system, Invitrogen, Inc) was adapted in this experiment. T-Rex vectors expressing HPV16 E2, E6 or E7 protein were constructed. Vectors containing mutant E2, E6 or E7 genes were utilized as negative controls. T-Rex 293 cells were then transfected with the HPV plasmids, and expression of HPV genes were activated by tetracycline for 4 hours, 24 hours and 72 hours. Total cellular RNA was extracted from the transfected cells by RNeasy® Protect Mini kit (Qiagen, Valencia, Calif.) and converted into the single stranded cDNA form with random hexamers using the High-Capacity cDNA Archive Kit (Applied Biosystems, P/N: 4322171). Real-time PCR was performed on the ABI Prism® 7700 Sequence Detection System using TaqMan® Universal PCR Master Mix (Applied Biosystems, Inc., Foster City, Calif.).

The primers and probes for specific amplification of MCM2, MCM6, MCM7, TOP2A, Cyclin E1, p21, p14, HPV16E2, E6 and E7 were designed with ABI Primer Express™ program, v1.5. MCM7 contains four transcriptional variants: transcript variant 1 (T1, refseq NM_005916) and transcript variant 2 (T2, refseq NM_182776) were identified in NCBI Entrez nucleotide database. Variant T3 and T4 have alternate exons near the 5'-end as analyzed by EST assembly through NCBI's Model Maker. Primers and probes were designed as T1T3, T2T4, T2 and T3T4 specifically for detecting variants T1 and T3, T2 and T4, T2, and T3 and T4, respectively. The sequences of primers and probes are shown as shown in Examples 10 and 11.

The probes were labeled with a fluorescent dye FAM (6-carboxyfluorescein) on the 5' base, and a quenching dye TAMRA (6-carboxytetramethylrhodamine) on the 3' base. 18S ribosomal RNA was utilized as endogenous control. 18S rRNA probe was labeled with a fluorescent dye VIC. Pre-developed 18S rRNA primer/probe mixture was purchased from Applied Biosystems. 10 ng of cDNA were applied to the reaction mixture containing 0.9 µM and 0.25 µM of the primers and probes, respectively, in a total volume of 25 µl. The amplification conditions were: 2 minutes at 50° C., 10 minutes at 95° C., and a two-steps cycle of 95° C. for 15 seconds and 60° C. for 60 seconds, for a total of 40 cycles. At least three no-template control reaction mixtures were included in each run. All experiments were performed in duplicate. The relative quantification method was employed to calculate the expression levels of target genes relative to the 18S endogenous control, based on their CT values following the ABI's user manual (P/N 4303859).

Results

Expression of HPV16 E2, E6 and E7 genes in T-Rex 293 cells was observed to increase through the time-course of transfection. mRNA expression of Topo2A, MCM2, MCM6, MCM7 and cyclin E in T-Rex 293 cells was significantly induced by HPV16 E6 or E7 genes, post-transfection from 4 hours up to 72 hours. However, there were no elevated expression levels detected for p21 and p14 post HPV gene transfection. Expression of E6 or E7 did not appear to be repressed by co-transfection of E2 gene. This is because the expression of E6 or E7 was purely driven by the external CMV promoter instead of the natural HPV promoters. The latter are not present in this model system.

TABLE 58

Topo2A

| Transfection | 0 h | 0 h SD | 4 h | 4 h SD | 24 h | 24 h SD | 72 h | 72 h SD |
|---|---|---|---|---|---|---|---|---|
| 293-H16E2 | 6.91 | 0.07 | 5.22 | 0.13 | 5.68 | 0.14 | 6.61 | 0.36 |
| 293-H16E6 | 6.91 | 0.07 | 11.31 | 0.22 | 18.13 | 0.89 | 17.39 | 0.85 |
| 293-H16E7 | 6.91 | 0.07 | 20.33 | 0.9 | 28.94 | 0.71 | 35.02 | 1.03 |
| 293-H16dE7 | 6.91 | 0.07 | 6.43 | 0.35 | 8.18 | 0.64 | 7.39 | 0.18 |
| 293-LacZ | 6.91 | 0.07 | 7.4 | 0.07 | 7.36 | 0.22 | 7.25 | 0.67 |

TABLE 59

MCM2

| Transfection | 0 h | 0 h SD | 4 h | 4 h SD | 24 h | 24 h SD | 72 h | 72 h SD |
|---|---|---|---|---|---|---|---|---|
| 293-H16E2 | 4.79 | 0.23 | 5.25 | 0.36 | 5.24 | 0.31 | 4.44 | 0.3 |
| 293-H16E6 | 4.79 | 0.23 | 6.04 | 0.21 | 9.38 | 0.37 | 12.08 | 0.18 |
| 293-H16E7 | 4.79 | 0.23 | 10.81 | 0.16 | 12.29 | 0.36 | 16.34 | 0.8 |
| 293-H16dE7 | 4.79 | 0.23 | 5.72 | 0.36 | 4.98 | 0.27 | 5.03 | 0.39 |
| 293-LacZ | 4.79 | 0.23 | 5.67 | 0.61 | 5.68 | 0.47 | 5.98 | 0.79 |

TABLE 60

MCM6

| Transfection | 0 h | 0 h SD | 4 h | 4 h SD | 24 h | 24 h SD | 72 h | 72 h SD |
|---|---|---|---|---|---|---|---|---|
| 293-H16E2 | 3.62 | 0.2 | 3.5 | 0.22 | 4.72 | 0 | 4.44 | 0.26 |
| 293-H16E6 | 3.62 | 0.2 | 4.74 | 0.07 | 9.03 | 0.04 | 9.68 | 0.43 |
| 293-H16E7 | 3.62 | 0.2 | 7.7 | 0.04 | 13.5 | 0.33 | 14.03 | 0.41 |
| 293-H16dE7 | 3.62 | 0.2 | 5.23 | 0.28 | 4.6 | 0.32 | 4.73 | 0.37 |
| 293-LacZ | 3.62 | 0.2 | 4.77 | 0.12 | 4.66 | 0.14 | 5.34 | 0.39 |

TABLE 61

MCM7

| Transfection | 0 h | 0 h SD | 4 h | 4 h SD | 24 h | 24 h SD | 72 h | 72 h SD |
|---|---|---|---|---|---|---|---|---|
| 293-H16E2 | 4.2 | 0.04 | 6.3 | 0.28 | 5.3 | 0.18 | 5.8 | 0.31 |
| 293-H16E6 | 4.2 | 0.04 | 4.99 | 0.05 | 9.55 | 0.23 | 15.24 | 0.3 |
| 293-H16E7 | 4.2 | 0.04 | 10.11 | 0.84 | 14.23 | 0.84 | 21.18 | 0.31 |
| 293-H16dE7 | 4.2 | 0.04 | 3.65 | 0.3 | 6.06 | 0.3 | 4.64 | 0.07 |
| 293-LacZ | 4.2 | 0.04 | 5.74 | 0.45 | 5.31 | 0.55 | 5.66 | 0.17 |

TABLE 62

Cyclin E1

| Transfection | 0 h | 0 h SD | 4 h | 4 h SD | 24 h | 24 h SD | 72 h | 72 h SD |
|---|---|---|---|---|---|---|---|---|
| 293-H16E2 | 6.02 | 0.00 | 5.06 | 0.10 | 5.03 | 0.35 | 5.72 | 0.31 |
| 293-H16E6 | 6.02 | 0.00 | 9.19 | 0.18 | 8.95 | 0.79 | 9.38 | 0.18 |
| 293-H16E7 | 6.02 | 0.00 | 12.91 | 0.38 | 17.63 | 0.17 | 17.32 | 0.25 |
| 293-H16dE7 | 6.02 | 0.00 | 5.45 | 0.24 | 6.87 | 0.20 | 5.11 | 0.08 |
| 293-LacZ | 6.02 | 0.00 | 5.72 | 0.31 | 6.28 | 0.37 | 5.65 | 0.64 |

TABLE 63 p21

| Transfection | 0 h | 0 h SD | 4 h | 4 h SD | 24 h | 24 h SD | 72 h | 72 h SD |
|---|---|---|---|---|---|---|---|---|
| 293-H16E2 | 4.76 | 0.19 | 4.05 | 0.30 | 5.19 | 0.61 | 4.92 | 0.60 |
| 293-H16E6 | 4.76 | 0.19 | 5.56 | 0.19 | 5.60 | 0.08 | 7.21 | 0.07 |
| 293-H16E7 | 4.76 | 0.19 | 7.52 | 0.29 | 5.22 | 0.13 | 6.45 | 0.13 |
| 293-H16dE7 | 4.76 | 0.19 | 4.38 | 0.26 | 5.60 | 0.66 | 5.10 | 0.05 |
| 293-LacZ | 4.76 | 0.19 | 3.86 | 0.00 | 4.53 | 0.27 | 5.37 | 0.29 |

TABLE 64 p14

| Transfection | 0 h | 0 h SD | 4 h | 4 h SD | 24 h | 24 h SD | 72 h | 72 h SD |
|---|---|---|---|---|---|---|---|---|
| 293-H16E2 | 4.78 | 0.30 | 4.44 | 0.09 | 5.04 | 0.44 | 5.04 | 0.07 |
| 293-H16E6 | 4.78 | 0.30 | 4.77 | 0.12 | 5.48 | 0.13 | 4.52 | 0.11 |
| 293-H16E7 | 4.78 | 0.30 | 6.38 | 0.62 | 5.60 | 0.25 | 6.43 | 0.35 |
| 293-H16dE7 | 4.78 | 0.30 | 5.08 | 0.12 | 5.53 | 0.35 | 5.10 | 0.15 |
| 293-LacZ | 4.78 | 0.30 | 4.54 | 0.40 | 4.68 | 0.16 | 5.76 | 0.25 |

TABLE 65

HPV16 E2

| | E2 | E6 | E7 | dE2 | dE6 | dE7 | E2 + E6 | E2 + E7 | dE2 + E6 | dE2 + E7 | LacZ | Mock |
|---|---|---|---|---|---|---|---|---|---|---|---|---|
| 4 h | 130.22 | 0 | 0 | 110.7 | 0 | 0 | 95.34 | 36.6 | 3.94 | 12.86 | 0 | 0 |
| 24 h | 162.12 | 0 | 0 | 111.41 | 0 | 0 | 118.17 | 90.19 | 19.77 | 7.7 | 0 | 0 |
| 72 h | 251.55 | 0 | 0 | 141.57 | 0 | 0 | 162.54 | 128.41 | 32.94 | 9.89 | 0 | 0 |

TABLE 66

HPV16 E6

| | E2 | E6 | E7 | dE2 | dE6 | dE7 | E2 + E6 | E2 + E7 | dE2 + E6 | dE2 + E7 | LacZ | Mock |
|---|---|---|---|---|---|---|---|---|---|---|---|---|
| 4 h | 0 | 205 | 0 | 0 | 219.87 | 0 | 128.41 | 0 | 199.65 | 0 | 0 | 0 |
| 24 h | 0 | 329.67 | 0 | 0 | 225.96 | 0 | 158.31 | 0 | 188.03 | 0 | 0 | 0 |
| 72 h | 0 | 757.26 | 0 | 0 | 315.22 | 0 | 392 | 0 | 271.55 | 0 | 0 | 0 |

TABLE 67

HPV16 E7

| | E2 | E6 | E7 | dE2 | dE6 | dE7 | E2 + E6 | E2 + E7 | dE2 + E6 | dE2 + E7 | LacZ | Mock |
|---|---|---|---|---|---|---|---|---|---|---|---|---|
| 4 h | 0 | 0 | 330.76 | 0 | 0 | 165.48 | 0 | 120.65 | 0 | 201.19 | 0 | 0 |
| 24 h | 0 | 0 | 1514.6 | 0 | 0 | 239.63 | 0 | 857.89 | 0 | 600.57 | 0 | 0 |
| 72 h | 0 | 0 | 2806.8 | 0 | 0 | 355.9 | 0 | 1444.25 | 0 | 809.11 | 0 | 0 |

Example 14

Increasing Antigen Accessibility in Immunocytochemistry and Immunohistochemistry Methods Using a Slide Pretreatment Buffer Specimen Selection and Reagent Description Paired cytology and histology specimens, from the same patient, were subjected to immunoassays to detect biomarker overexpression. Paraffin block tissue samples and SurePath® cytology specimens from patients categorized as ASCUS (3), LSIL (6), and HSIL (5) were analyzed. The reagents used were the Antibody Cocktail (for cytology), the Modified Antibody Cocktail (for histology), Detection Reagents, Counterstains, and SureSlide® Preparation Buffer 10× (pretreatment buffer).

Cytology Slide Preparation and Automated Immunocytochemistry

For immunocytochemistry, slide preparation and pretreatment was conducted as indicated in Example 5. Automated immunocytochemistry was then performed on each cytology specimen as described in Example 5 with one exception. The primary antibody cocktail (MCM2 Clone 26H6.19 1:10,000, MCM2 Clone 27C5.6 1:800, TOPOIIA Clone SWT3D1 1:1000) incubation was reduced to 30 minutes for this experiment.

Histology Slide Preparation and Automated Immunohistochemistry

For each case, 4 micron sections were cut and dried overnight or for 20 minutes in a 70° C. forced air oven. Sections were deparaffinized in 3 changes of xylene for 5 minutes each. Slides were then cleared in absolute alcohol for 5 minutes each. Slides were brought down to water and rinsed thoroughly. Slides were transferred to a preheated solution of 1× SureSlide Preparation Buffer and incubated in the steamer for 25 minutes. The slides were removed from the steamer and allowed to cool at room temperature for 20 minutes. Slides were slowly rinsed in water until the buffer was completely exchanged. A TBST rinse was applied for 2 changes at 2 minutes each.

Automated immunohistochemistry was conducted as described in Example 5 for immunocytochemistry, with two exceptions. The primary antibody cocktail incubation was reduced to 30 minutes for this experiment. Additionally, the primary antibody cocktail was modified with the following dilutions (MCM2 Clone 26H6.19 1:4,000, MCM2 Clone 27C5.6 1:200, TOPOIIA Clone SWT3D1 1:400).

Results

The anticipated staining patterns were observed on both the histology and cytology specimens with the use of the RUO reagents. Specifically, the ability to immunostain both histology and cytology specimens with the SureSlide® Preparation Buffer, Detection Reagents and the Counterstain Reagents was successfully demonstrated.

TABLE 68

Biomarker Nucleotide and Amino Acid Sequence Information

| Biomarker Name | Nucleotide Sequence | | Amino Acid Sequence | |
| --- | --- | --- | --- | --- |
| | Accession No. | Sequence Identifier | Accession No. | Sequence Identifier |
| Cyclin E1 (Isoform 1) | NM_001238 | SEQ ID NO: 1 | NP_001229 | SEQ ID NO: 2 |
| Cyclin E1 (Isoform 2) | NM_057182 | SEQ ID NO: 3 | NP_476530 | SEQ ID NO: 4 |
| Cyclin E2 (Isoform1) | NM_057749) | SEQ ID NO: 5 | NP_477097 | SEQ ID NO: 6 |
| Cyclin E2 (Isoform 2) | NM_057735 | SEQ ID NO: 7 | NP_477083 | SEQ ID NO: 8 |
| Cyclin E2 (Isoform 3) | NM_004702 | SEQ ID NO: 9 | NP_004693 | SEQ ID NO: 10 |
| MCM2 | NM_004526 | SEQ ID NO: 11 | NP_0045417 | SEQ ID NO: 12 |
| MCM6 | NM_005915 | SEQ ID NO: 89 | NP_005906 | SEQ ID NO: 90 |
| MCM7 (Isoform 1) | NM_005916 | SEQ ID NO: 13 | NP_005907 | SEQ ID NO: 14 |
| MCM7 (Isoform 2) | NM_182776 | SEQ ID NO: 15 | NP_877577 | SEQ ID NO: 16 |
| p21/waf1 (Variant 1) | NM_000389 | SEQ ID NO: 17 | NP_000380 | SEQ ID NO: 18 |
| p21/waf1 (Variant 2) | NM_078467 | SEQ ID NO: 19 | NP_510867 | SEQ ID NO: 20 |
| p14ARF | NM_058195 | SEQ ID NO: 21 | NP_478102 | SEQ ID NO: 22 |
| Topo2a | NM_001067 | SEQ ID NO: 23 | NP_0010568 | SEQ ID NO: 24 |

In light of the above description and examples, one skilled in the art will appreciate that the methods of the invention permit superior detection of high-grade cervical disease, independent of age, in comparison to conventional practice. The methods of the invention may find particular use as described below:

For women over the age of thirty, the test may be a reflex from either an HPV positive result or as a reflex from an ASCUS+ cytology result.

For women under the age of 30, the test may be used in combination with cytology for the detection of high-grade cervical disease.

For women over the age of 30, the test may be used in combination with cytology for the detection of high-grade cervical disease.

For women under the age of 30, the test may be used as a primary screen to detect high-grade cervical disease.

For women over the age of 30, the test may be used as a primary screen to detect high-grade cervical disease.

The test may be a replacement for the Pap smear in women under the age of thirty.

Ultimately, the test may be a replacement for the Pap smear, independent of age.

Other potential advantages stemming from the practice of the present invention include:

Detection of histologic high-grade abnormality in women 30 years old and above with NIL/HPV positive results.

Superior specificity for the detection of high-grade cervical disease in women over the age of 30 who are positive to the DNA+Pap test.

Superior detection for high-grade cervical disease in women within the ASC-US, ASC-H, and LSIL categories, independent of age.

Superior specificity for the detection of high-grade cervical within HSIL category.

Detection of high-grade cervical disease in conjunction with cytology-based diagnosis in women under the age of 30.

Detection of high-grade cervical disease in conjunction with cytology-based diagnosis, independent of age.

Improved specificity for the detection of high-grade cervical disease as a primary screen in women under the age of 30.

Improved specificity for the detection of high-grade cervical disease as a primary screen, independent of age.

Identification of cervical disease and differentiation of HPV infection and high-grade cervical disease.

Acceptable assay performance can be established using manual interpretation or assisted interpretation via automated microscopy.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

That which is claimed:

1. A method for diagnosing high-grade cervical disease in a patient independent of the patient's HPV infection status comprising detecting overexpression of at least one nucleic acid molecule that encodes a nuclear biomarker that is selectively overexpressed in high-grade cervical disease, wherein the nuclear biomarker is selected from the group consisting of p14ARF, $p21^{waf1}$, Topo2A, and Cyclin E, the method comprising:

(a) obtaining a body sample from the patient;
(b) isolating nucleic acid material from the sample;
(c) mixing said nucleic acid material with at least one pair of oligonucleotide primers specific for the nuclear biomarker and a thermostable DNA polymerase under conditions that are suitable for amplification by polymerase chain reaction (PCR);
d) performing PCR; and,
e) detecting PCR amplification products.

2. The method of claim 1, wherein performing PCR comprises performing RT-PCR.

3. The method of claim 1, wherein the method is performed in conjunction with morphological analysis.

4. The method of claim 1, wherein the sample comprises cervical cells in suspension in a liquid-based preparation.

5. The method of claim 1, wherein the sample comprises a cervical tissue sample.

6. The method of claim 1, wherein the method is performed in response to the patient having an abnormal Pap smear result.

7. The method of claim 1, wherein the method is performed as a primary screen for high-grade cervical disease in a general patient population.

8. The method of claim 1, wherein the method if performed in conjunction with Papanicolaou (Pap) staining of a cervical sample from the patient.

* * * * *

UNITED STATES PATENT AND TRADEMARK OFFICE
CERTIFICATE OF CORRECTION

PATENT NO.         : 7,455,973 B2
APPLICATION NO.    : 11/506012
DATED              : November 25, 2008
INVENTOR(S)        : Fischer et al.

It is certified that error appears in the above-identified patent and that said Letters Patent is hereby corrected as shown below:

Column 1,

Line 38, after the words "cancer has been" insert all of page 2 of the original specification as follows -- widely accepted for years. The precursor to cervical cancer is dysplasia, also known in the art as CIN or squamous intraepithelial lesions (SIL). Squamous intraepithelial abnormalities may be classified by using the three-tiered (CIN) or two-tiered (Bethesda) system. Under the Bethesda system, low-grade squamous intraepithelial lesions (LSIL), corresponding to CINI and HPV infection, generally represent productive HPV infections with a relatively low risk of progression to invasive disease. High-grade squamous intraepithelial lesions (HSIL), corresponding to CINII and CINIII in the three-tiered system, show a higher risk of progression to cervical cancer than do LSIL, although both LSIL and HSIL are viewed as potential precursors of malignancy. Patient samples may also be classified as ASCUS (atypical squamous cells of unknown significance) or AGUS (atypical glandular cells of unknown significance) under this system.

A strong association of cervical cancer and infection by high-risk types of human papilloma virus (HPV), such as types 16, 18, and 31, has been established. In fact, a large body of epidemiological and molecular biological evidence has established HPV infection as a causative factor in cervical cancer.

UNITED STATES PATENT AND TRADEMARK OFFICE
CERTIFICATE OF CORRECTION

| | |
|---|---|
| PATENT NO. | : 7,455,973 B2 |
| APPLICATION NO. | : 11/506012 |
| DATED | : November 25, 2008 |
| INVENTOR(S) | : Fischer et al. |

It is certified that error appears in the above-identified patent and that said Letters Patent is hereby corrected as shown below:

Moreover, HPV is found in 85% or more of the cases of high-grade cervical disease. However, HPV infection is very common, possibly occurring in 5-15% of women over the age of 30, but few HPV-positive women will ever develop high-grade cervical disease or cancer. The presence of HPV alone is indicative only of infection, not of high-grade cervical disease, and, therefore, testing for HPV infection alone results in many false positives. See, for example, Wright *et al.* (2004) *Obstet. Gynecol.* 103:304-309.

Current literature suggests that HPV infects the basal stem cells within the underlying tissue of the uterine-cervix. Differentiation of the stem cells into mature keratinocytes, with resulting migration of the cells to the stratified cervical epithelium, is associated with HPV viral replication and re-infection of cells. During this viral replication process, a number of cellular changes occur that include cell-cycle de-regulation, active proliferation, DNA replication, transcriptional activation and genomic instability (Crum (2000) *Modern Pathology* 13:243-251; Middleton *et al.* (2003) *J. Virol.* 77:10186-10201; Pert *et al.* (2004) *Cancer Res.* 64:1359-1368).

Most HPV infections are transient in nature, with the viral infection resolving itself within a 12-month period. For those individuals who develop persistent infections--.

UNITED STATES PATENT AND TRADEMARK OFFICE
CERTIFICATE OF CORRECTION

PATENT NO. : 7,455,973 B2
APPLICATION NO. : 11/506012
DATED : November 25, 2008
INVENTOR(S) : Fischer et al.

It is certified that error appears in the above-identified patent and that said Letters Patent is hereby corrected as shown below:

Column 7,

Lines 62 - 67, cancel "widely accepted for years." through "lesions" on line 67.

Column 8,

Lines 1 - 40, cancel "(LSIL), corresponding" through "individuals who develop persistent infections" on line 40 (which is original page 2 of specification).

Column 10,

Line 45, "Al10" should read --A10--.

Column 45,

Lines 37, 46, 50, 53, and 56, "$\geqq$", all occurrences, should read --$\geq$--.

Column 46,

Line 33, "$\geqq$", both occurrences, should read --$\geq$--.

UNITED STATES PATENT AND TRADEMARK OFFICE
CERTIFICATE OF CORRECTION

PATENT NO.         : 7,455,973 B2
APPLICATION NO.    : 11/506012
DATED              : November 25, 2008
INVENTOR(S)        : Fischer et al.

It is certified that error appears in the above-identified patent and that said Letters Patent is hereby corrected as shown below:

<u>Column 47,</u>

Line 55, "200x g" should read --200xg--;

Line 58, "600x g" should read --600xg--.

<u>Column 48,</u>

Line 15, "$\geqq$" should read --$\geq$--.

Signed and Sealed this

Second Day of June, 2009

JOHN DOLL
*Acting Director of the United States Patent and Trademark Office*